US009162991B2

(12) United States Patent
Pardin et al.

(10) Patent No.: US 9,162,991 B2
(45) Date of Patent: Oct. 20, 2015

(54) CINNAMOYL INHIBITORS OF TRANSGLUTAMINASE

(71) Applicant: University of Ottawa, Ottawa, Ontario (CA)

(72) Inventors: Christophe Pardin, Strasbourg (FR); Jeffrey W. Keillor, Montreal (CA); William D. Lubell, Montreal (CA)

(73) Assignee: University of Ottawa, Ottawa, Ontario (CA)

( * ) Notice: Subject to any disclaimer, the term of this patent is extended or adjusted under 35 U.S.C. 154(b) by 0 days.

(21) Appl. No.: 14/015,047

(22) Filed: Aug. 30, 2013

(65) Prior Publication Data

US 2014/0024837 A1 Jan. 23, 2014

Related U.S. Application Data

(63) Continuation of application No. 12/602,425, filed as application No. PCT/CA2008/001049 on May 29, 2008, now Pat. No. 8,614,233.

(60) Provisional application No. 60/940,523, filed on May 29, 2007.

(51) Int. Cl.

| | |
|---|---|
| ***C07D 249/04*** | (2006.01) |
| ***C07C 205/43*** | (2006.01) |
| ***C07C 205/56*** | (2006.01) |
| ***C07D 209/08*** | (2006.01) |
| ***C07D 211/22*** | (2006.01) |
| ***C07D 213/50*** | (2006.01) |
| ***C07D 213/53*** | (2006.01) |
| ***C07D 221/04*** | (2006.01) |
| ***C07D 233/54*** | (2006.01) |
| ***C07D 233/60*** | (2006.01) |
| ***C07D 249/18*** | (2006.01) |
| ***C07D 265/06*** | (2006.01) |
| ***C07D 295/185*** | (2006.01) |
| ***C07D 311/12*** | (2006.01) |
| ***C07D 401/06*** | (2006.01) |
| ***C07D 471/04*** | (2006.01) |
| ***C12Q 1/48*** | (2006.01) |

(52) U.S. Cl.

CPC ............ *C07D 249/04* (2013.01); *C07C 205/43* (2013.01); *C07C 205/56* (2013.01); *C07D 209/08* (2013.01); *C07D 211/22* (2013.01); *C07D 213/50* (2013.01); *C07D 213/53* (2013.01); *C07D 221/04* (2013.01); *C07D 233/54* (2013.01); *C07D 233/60* (2013.01); *C07D 249/18* (2013.01); *C07D 265/06* (2013.01); *C07D 295/185* (2013.01); *C07D 311/12* (2013.01); *C07D 401/06* (2013.01); *C07D 471/04* (2013.01); *C12Q 1/48* (2013.01); *G01N 2333/91085* (2013.01); *G01N 2500/02* (2013.01)

(58) Field of Classification Search

None

See application file for complete search history.

(56) References Cited

U.S. PATENT DOCUMENTS

| | | | |
|---|---|---|---|
| 4,421,927 | A | 12/1983 | Picart |
| 6,906,105 | B2 | 6/2005 | Bowen et al. |
| 8,614,233 | B2 | 12/2013 | Pardin et al. |

FOREIGN PATENT DOCUMENTS

| | | |
|---|---|---|
| CA | 747429 | 11/1966 |
| CA | 1155121 | 10/1983 |
| CA | 1241016 | 8/1988 |
| CA | 2267320 | 4/1998 |
| CA | 2538960 | 3/2005 |
| CA | 2539165 | 3/2005 |
| CA | 2599794 | 9/2006 |
| CA | 2600287 | 9/2006 |
| EP | 0051514 | 5/1982 |
| EP | 0958815 | 11/1999 |
| JP | 45014790 | 6/1970 |
| WO | WO 2008/144933 | 5/2008 |

OTHER PUBLICATIONS

STN Registry entry for CAS RN 371925-28-9, entry date Nov. 27, 2001, accessed via STN Express on Dec. 15, 2013.*

STN Registry database entries for CAS RN 955589-37-4 & CAS RN 955554-28-6 (Published in STN Registry Nov. 22, 2007); Accessed Nov. 3, 2014.*

Latif et al., J. Org. Chem., vol. 34(11), 1968, p. 3653.*

Adisakwattana et al., "Structure-Activity Relationships of Trans-Cinnamic Acid Derivatives on Alpha-Glucosidase Inhibition", S. Bioorganic & Medicinal Chemistry Letters, Jun. 2004, 14(11), 2893-2896.

Aeschlimann et al., "Transglutaminases: Protein Cross-Linking Enzymes in Tissues and Body Fluids", Thrombosis and Haemostasis, Jan. 1994, 71(4), 402-415.

Alvarez et al., "A Practical Procedure for the Synthesis of Alkyl Azides at Ambient Temperature in Dimethyl Sulfoxide in High Purity and Yield", Synthesis: Journal of Synthetic Organic Chemistry, Apr. 1997, 4, 413-414.

(Continued)

*Primary Examiner* — Alicia L Otton

(74) *Attorney, Agent, or Firm* — Baker & Hostetler LLP

(57) ABSTRACT

A compound of Formula I or Formula II:

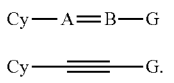

I

II

4 Claims, 5 Drawing Sheets

(56) References Cited

OTHER PUBLICATIONS

Amendola et al., "HIV-1 gp120-Dependent Induction of Apoptosis in Antigen-Specific Human T Cell Clones is Characterized by 'Tissue' Transglutaminase Expression and Prevented by Cyclosporine A", FEBS Letters, Feb. 1994, 339(3), 258-264.
Azari et al., "Transglutaminase Activity in Normal and Hereditary Cataractous Rat Lens and Its Partial Purification", Current Eye Research., Jan. 1981, 1(8), 463-469.
Bellamy, "Selective Reduction of Aromatic Nitro Compounds with Stannous Chloride in Non Acidic and Non Aqueous Medium", Tetrahedron Letters, 1984, 25(8), 839-842.
Benzinger et al., "Propagating Structure of Alzheimer's Beta-Amyloid(10-35) is Parallel Beta-Sheet with Residues in Exact Register", PNAS, Nov. 10, 1998, 95(23), 13407-13412.
Bernard et al., "Precocious Appearance of Involucrin and Epidermal Transglutaminase During Differentiation of Psoriatic Skin", British Journal of Dermatology., Mar. 1986, 114(3), 279-283.
Bishop et al., "Human recombinant Factor XIII from *Saccharomyces cerevisiae.* Crystallization and Preliminary X-ray Data", Journal of Biological Chemistry, Aug. 1990, 265(23),13888-13889.
Buckle et al., "Studies on V-Triazoles. Part 4. The 4-Methoxybenzyl Group, a Versatile N-Protecting Group for the Synthesis of N-Unsubstituted V-Triazoles", Journal of the Chemical Society, Perkin Transactions 1, Jan. 1982, 627-630.
Candi et al., "A Highly Conserved Lysine Residue on the Head Domain of Type Ii Keratins is Essential for the Attachment of Keratin Intermediate Filaments to the Cornified Cell Envelope Through Isopeptide Crosslinking by Transglutaminases", PNAS, Mar. 1998, 95(5), 2067-2072.
Cardoso et al., Journal of Natural Products 2006, 69, pp. 1046-1050.
Chica et al., "Tissue Transglutaminase Acylation: Proposed Role of Conserved Active Site TYR and TRP Residues Revealed by Molecular Modeling of Peptide Substrate Binding", Protein Science, Mar. 2004, 13(4), 979-991.
Dalziel et al., "Inflammation Due to Intra-Cutaneous Implantation of Stratum Corneum", Journal of Experimental Pathology, Feb. 1984, 65(1), 107-115.
Day et al., "A Continuous Spectrophotometric Linked Enzyme Assay for Transglutaminase Activity", Analytical Biochemistry, Oct. 1, 1999, 274(1), 141-144.
De Young et al., "Transglutaminase Activity in Human and Rabbit Ear Comedogenesis: A Histochemical Study", Journal of Investigative Dermatology, Mar. 1984, 82(3), 275-259.
Dedeoglu et al., "Therapeutic Effects of Cystamine in a Murine Model of Huntington's Disease", The Journal of Neuroscience, Oct. 2002, 22(20), 8942-8950.
Durinda et al., "Studies of Amphenone-Type Adrenal Cortex Inhibitors. III. Aminoazachalcones," Cesko-Slovenka Farmacie (1977), 26(5), 140-149.
Durinda et al., "Chemistry and Biological Properties and Azachalcones," Acta Facultatis Pharmaceuticae Bohemoslovenicae (1966), 12, 89-129.
Duval et al., "Structure-Activity Relationship Study of Novel Tissue Transglutaminase Inhibitors", Bioorganic & Medical. Chemistry Letters, Apr. 2005, 15(7), 1885-1889.
El Nahas et al., "Elevated $\epsilon(\gamma$-Glutamyl)lysine in Human Diabetic Nephropathy Results from Increased Expression and Cellular Release of Tissue Transglutaminase", Nephron Clinical Practice, Mar. 2004, 97, C108-C117.
Farmer et al., "Correlations Among Numbers of Neuritic Plaques, Neurofibrillary Tangles, and the Severity of Senile Dementia: 135", Journal of Neuropathology & Experimental Neurology, May-Jun. 1976, 35(3), 367 and American Association of Neuropathologists: Abstracts of the 52nd annual meeting, Jun. 11-13, 1976, Hyatt Regency Hotel San Francisco, California.
Fesus, "Transglutaminase Activation: Significance with Respect to Immunologic Phenomena", L. Surv. Immunol. Res., 1982, 1(4), 297-304.
Fox et al., "Identification of the Calcium Binding Site and a Novel Ytterbium Site in Blood Coagulation Factor XIII by X-Ray Crystallography", Journal of Biological Chemistry, Feb. 1999, 274(8), 4917-4923.
Gagnon et al., "Peptide Coupling of Unprotected Amino Acids Through in Situ P-Nitrophenyl Ester Formation", Tetrahedron Letters, Aug. 2002, 43, 7717-7719.
Gillet et al., "Expression and Rapid Purification of Highly Active Hexahistidine-Tagged Guinea Pig Liver Transglutaminase", Protein Expression and Purification, Feb. 2004, 33, 256-564.
Gobec et al., "Cinnamic Acid Esters as Potent Inhibitors of Fungal 17Beta-Hydroxysteroid Dehydrogenase—A Model Enzyme of the Short-Chain Dehydrogenase/Reductase Superfamily", Bioorganic & Medicinal Chemistry Letters, May 2004, 14, 3933-3936.
Hilgenfeld et al., "Crystallization of Blood Coagulation Factor XIII by an Automated Procedure", FEBS Lett., Jun. 1990, 265(12), 110-112.
International Patent Application No. PCT/CA2008/001049: International Search Report dated Sep. 9, 2008, 2 pages.
Irikura et al., "Antitumor Activity of 3-(Substituted Cinnamoyl)Pyridiine and 1-oxide", Chemical & Pharmaceutical Bulletin, Jul. 1970, 18(7), 1408-1413.
Keillor, "Tissue Transglutaminase Inhibition", Chemistry & Biology, Apr. 2005, 12, 410-412.
Kim et al., "Crystallization and Preliminary X-Ray Analysis of Human Transglutaminase 3 from Zymogen to Active Form", Journal of. Structural Biology, Jul. 2001, 135, 73-77.
Leblanc et al., "Kinetic Studies of Guinea Pig Liver Transglutaminase Reveal a General-Base-Catalyzed Deacylation Mechanism", Biochemistry, Jun. 2001, 40(28), 8335-8342.
Loren et al.,"The Banert Cascade: A Synthetic Sequence to Polyfunctional NH-1,2,3-Triazoles", Synthesis: Journal of Synthetic Organic Chemistry, Jun. 2005, 9, 1514-1520.
Mastroberardino et al., "Tissue Transglutaminase Ablation Reduces Neuronal Death and Prolongs Survival in a Mouse Model of Huntington's Disease", Cell Death Differentiation, Jun. 2002, 9, 873-880.
Miller et al., "The Synthesis of Electron Donor-Acceptor Substituted Pyrazoles", J. Heterocyclic Chem., May-Jun. 1993, 30, 755-763.
Nogushi et al., "Crystal Structure of Red Sea Bream Transglutaminase", The Journal of Biological Chemistry, Apr. 2001, 276(15), 12055-12059.
Norlund et al., "Elevated Transglutaminase-Induced Bonds in PHF Tau in Alzheimer's Disease", Brain Research, Sep. 1999, 851, 154-163.
Penning et al., "Synthesis of Cinnamic Acids and Related Isosteres as Potent and Selective Avβ3 Receptor Antagonists", Bioorganic & Medicinal Chemistry Letters, Jan. 2004, 14, 1471-1476.
Piper et al., "High Selectivity of Human Tissue Transglutaminase for Immunoactive Gliadin Peptides: Implications for Celiac Sprue", Biochemistry, 2002, 41(1), 386-393.
Reiter et al., J. Heterocyclic Chem., 24, 127 (1987).
Rostovtsev et al., "A Stepwise Huisgen Cycloaddition Process: Copper(I)-Catalyzed Regioselective "Ligation" of Azides and Terminal Alkynes", Angew. Chem. Int. Ed., 2002, 41(14), 2596-2599.
Schroeder et al., "Type I Keratinocyte Transglutaminase: Expression in Human Skin and Psoriasis", The Society for Investigative Dermatology, Inc., Jul. 1992, 99(1), 27-34.
Selkoe et al., "Alzheimer's Disease: Insolubility of Partially Purified Paired Helical Filaments in Sodium Dodecyl Sulfate and Urea", Science, Mar. 1982, 215(4537), 1243-1345.
Selkoe et al., "Brain transglutaminase: In Vitro Crosslinking of Human Neurofilament Proteins into Insoluble Polymers", Proc. Natl. Acad. Sci. U.S.A., Oct. 1982, 79, 6070-6074.
Sharpless et al., "Click Chemistry: Diverse Chemical Function from a Few Good Reactions", Angew. Chem. Int. Ed., Jun. 2001, 40, 2004-2021.
Siegel et al., "Transglutaminase 2 Inhibitors and Their Therapeutic Role in Disease States" Pharmacology & Therapeutics, Aug. 2007, 115(2), 232-245.
"Substance, 105833", Mar. 26, 2014, 213 pages.
"Substance, 094630", Mar. 28, 2014, 8 pages.

(56) References Cited

OTHER PUBLICATIONS

Weiss et al., "Dehydration Leads to a Phase Transition in Monoclinic Factor XIII Crystals", Acta Cryst. Section D, Aug. 1999, D55(11), 1858-1862.
Yee et al., "Three-dimensional structure of a transglutaminase: human blood coagulation factor XIII" Proc. Natl. Acad. Sci. USA, Jul. 1994, 91, 7296-7300.
Zou, Xuefei et al., "Highly Regioselective Friedel-Crafts Alkylation of Indoles With α, β-unsaturated N-acylbenzotriazoles," Tetrahedron Letters, 2006, 47(22), 3767-3771.
SciFinder®, "CAS Registry No. 647833-19-0", American Chemical Society (ACS), © 2015, 1 page.
SciFinder®, "CAS Registry No. 1349766-07-9", American Chemical Society (ACS), © 2015, 1 page.
SciFinder®, "CAS Registry No. 71322-74-2", American Chemical Society (ACS), © 2015, 1 page.
SciFinder®, "CAS Registry No. 21473-06-3", American Chemical Society (ACS), © 2015, 1 page.
SciFinder®, "CAS Registry No. 156969-36-7", American Chemical Society (ACS), © 2015, 1 page.
SciFinder®, "CAS Registry No. 955589-37-4", American Chemical Society (ACS), © 2015, 1 page.
SciFinder®, "CAS Registry No. 955554-28-6", American Chemical Society (ACS), © 2015, 1 page.
SciFinder®, "CAS Registry No. 757980-12-4", American Chemical Society (ACS), © 2015, 1 page.

* cited by examiner

50b

13b

CINNAMOYL INHIBITORS OF TRANSGLUTAMINASE

CROSS-REFERENCE TO RELATED APPLICATIONS

This application is a continuation of U.S. Ser. No. 12/602,425 (now U.S. Pat. No. 8,614,233, issued Dec. 24, 2013), which was filed on Apr. 15, 2010 as the United States national stage entry of PCT/CA2008/001049, which was filed on May 29, 2008 and claims priority to U.S. Provisional App. No. 60/940,523, filed on May 29, 2007. The entire contents of each of the above-cited applications are incorporated herein in their entireties.

FIELD OF INVENTION

The present invention concerns cinnamoyl inhibitors of transglutaminase.

BACKGROUND OF THE INVENTION

Transglutaminases (TGases, EC 2.3.2.13) are calcium-dependent enzymes that catalyze the intermolecular cross-linking of certain proteins through the formation of $\gamma$-glutamyl-$\epsilon$-lysine side chain bridges. In mammals, three types of TGases have been characterized to date and are found in tissue, plasma and epidermis. Tissue TGases are involved in diverse biological processes such as endocytosis, apoptosis and cell growth regulation. The plasma-soluble form of TGase, Factor XIIIa, stabilizes blood clots by catalyzing the cross-linking of fibrin during hemostasis. Epidermal TGase plays a key role in the synthesis of the cornified envelope of epidermal keratinocytes.

Unregulated, high TGase activities have been linked to physiological disorders involved in disease states such as acne, cataracts, immune system diseases, psoriasis, neuropathy, neurodegenerative disease such as, for example, Alzheimer's disease, Huntington's disease, Parkinson's disease, Celiac disease, cancer metastasis, inflammation, fibrosis, diabetes, autoimmune diseases, lamellar ichthyosis, psoriasis, supranuclear palsy, renal failure. Potent and selective TGase inhibitors offer means for elucidating the roles of TGases in various disease states and may serve as lead compounds for therapeutic development.

In recent years, TGase activity has been shown to be regulated by a number of potential TGase inactivators, including sulfonamides, iodoactetates [i.e. iodoacetamide], isocyanates [i.e. propylisocyanate], thioureas [e.g. 1-(5-aminopentyl)-3-phenylthiourea (3)], acivicin derivatives [e.g. benzyl 1-((3-bromo-4,5-dihydroisoxazol-5-yl)methylcarbamoyl)-2-phenylethylcarbamate], sulfonium methyl ketones, thioacetonyl heterocycles [e.g. 1,4,5-trimethyl-2-[(2-oxopropyl)thio]imidazole] and electrophilic glutamine analogues. Poor selectivity has, however, limited the therapeutic utility of these classes of inhibitors.

Improved affinity for TGase has been displayed by irreversible inhibitors, such as dipeptide-bound 1,2,4-thiadizoles [i.e. $N_\alpha$-carbobenzyloxy-2-amino-$N_\delta$-(3-methyl-5-[1,2,4]thiadiazolyl)-L-glutamine], $\alpha,\beta$-unsaturated amides and epoxides [i.e. $N_\alpha$-carbobenzyloxy-$N_\omega$-acryloyl-L-lysinylglycine and $N_\alpha$-carbobenzyloxy-$N_\omega$-oxiranecarbonylamino-L-lysinylglycine]. These inhibitors are generally selective for tissue TGase, compared to microbial TGase or GGT, a related transpeptidase.

Thieno[2,3-d]pyrimidin-4-one acylhydrazide derivatives have recently been reported (Duval, E. et al *Bioorg. Med. Chem. Lett.* 2005, 15, 1885) to be reversible and potent inhibitors of tissue transglutaminase (TG2). An initial structure-activity relationship study for this class of TG2 inhibitors revealed that the acylhydrazide thioether side-chain was important for affinity. Analogs bearing the thiophene ring such as thieno[2,3-d]pyrimidin-4-one acylhydrazide derivatives were among the most potent inhibitors and exhibited slow-binding inhibition.

It is desired to provide further compounds, which can inhibit tissue transglutaminase.

SUMMARY OF THE INVENTION

The inventors have discovered a series of novel trans-cinammoyl derivatives, which are potent inhibitors of guinea pig liver transglutaminase (TGase). The inhibitors can be sorted into two sub-classes: substituted cinnamoyl benzotriazolyl amides and the 3-(substituted cinnamoyl)pyridines, also known as azachalcones. Both of these subclasses displayed reversible inhibition of TGase and were competitive with acyl donor TGase substrates at $IC_{50}$ values less than 20 $\mu$M. Furthermore, the inventors have also developed the Huisgen [3+2] cycloaddition to form novel 4-cinnamoyl-triazole analogs of the present invention.

According to an aspect of the present invention there is provided a compound of Formula I or Formula II:

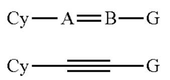

I

II wherein

Cy is a ring system chosen from 1) aryl, 2) heteroaryl, 3) heterocyclyl, or 4) heterobicyclyl, wherein the aryl, the heteroaryl, the heterocyclyl and the heterobicyclyl are optionally substituted with one or more $R^1$ substituents;

A and B are selected from $CR^2$ and N, and each of A and B can be the same or different;

G is chosen from

1)

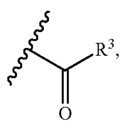

2)

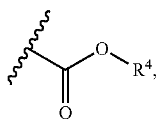

3)

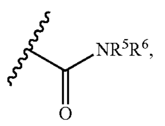

-continued

4)

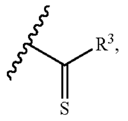

5)

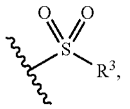

6)

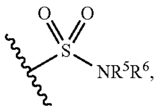

7) $C(=NR^5)NR^5R^6$, or

8) $P(=O)(NR^5R^6)_2$;

$R^1$ is chosen from
1) halogen,
2) $NO_2$,
3) CN,
4) $C_1$-$C_6$ alkyl,
5) $C_3$-$C_7$ cycloalkyl,
6) haloalkyl,
7) $OR^7$,
8) $NR^8R^9$,
9) $SR^7$,
10) $COR^7$,
11) $C(O)OR^7$,
12) $S(O)_2R^7$,
13) $(CONR^8R^9)_{1-3}$,
14) $S(O)_2NR^8R^9$,
15) aryl,
16) heteroaryl,
17) heterocyclyl, or
18) heterobicyclyl, wherein the alkyl and the cycloalkyl are optionally substituted with one or more $R^{11}$ substituents;

$R^2$ is chosen from
1) H,
2) $C_1$-$C_6$ alkyl,
3) $C_3$-$C_7$ cycloalkyl,
4) haloalkyl,
5) aryl,
6) heteroaryl,
7) heterocyclyl,
8) heterobicyclyl,
9) $OR^7$,
10) $SR^7$,
11) halogen,
12) amine,
13) thioether, or
14) $NR^8R^9$, wherein the aryl, the heteroaryl, the heterocyclyl and the heterobicyclyl are optionally substituted with one or more $R^1$ substituents;

$R^3$ is chosen from
1) $C_1$-$C_6$ alkyl,
2) $C_3$-$C_7$ cycloalkyl,
3) aryl,
4) heteroaryl,
5) heterocyclyl, or
6) heterobicyclyl, wherein the aryl, the heteroaryl, the heterocyclyl, and the heterobicylyl are optionally substituted with one or more $R^1$ substituents;

$R^4$ is chosen from
1) $C_1$-$C_6$ alkyl,
2) haloalkyl,
3) $C_3$-$C_7$ cycloalkyl,
4) aryl,
5) heteroaryl,
6) heterocyclyl, or
7) heterobicyclyl, wherein the alkyl and the cycloalkyl are substituted with one or more $R^3$ substituents; and wherein the aryl, the heteroaryl, the heterocyclyl, and the heterobicyclyl are optionally substituted with one or more $R^1$ substituents;

$R^5$ and $R^6$ are independently chosen from
1) H,
2) $C_1$-$C_6$ alkyl,
3) $C_3$-$C_7$ cycloalkyl,
4) haloalkyl,
5) aryl,
6) heteroaryl,
7) heterocyclyl,
8) heterobicyclyl,
9) $NR^8R^9$, or
10) $CONR^8R^9$, or $R^5$ and $R^6$ together with the nitrogen atom to which they are bonded form a five, six or seven membered heterocyclic ring optionally substituted with one or more $R^1$ substituents;

wherein the alkyl and the cycloalkyl are optionally substituted with one or more $R^3$ substituents; and wherein the aryl, the heteroaryl, the heterocyclyl, and the heterobicyclyl are optionally substituted with one or more $R^1$ substituents;

$R^7$ is chosen from
1) H,
2) $C_1$-$C_6$ alkyl,
3) aryl,
4) heteroaryl,
5) heterocyclyl, or
6) heterobicyclyl;

$R^8$ and $R^9$ are independently chosen from
1) H,
2) $C_1$-$C_6$ alkyl,
3) $COOR^{12}$,
4) Fmoc,
5) Boc,
6) $C(O)C_1$-$C_6$ alkyl,
7) carbonyl aryl,
8) carbonyl heteroaryl,
9) $SO_2$Aryl,
10) $SO_2$heteroaryl,
11) $PO_2$alkyl,
12) $PO_2$Aryl, or
13) $CONR^7R^8$, or $R^8$ and $R^9$ together with the nitrogen atom to which they are bonded form a five, six or seven membered heterocyclic ring;

wherein the alkyl is optionally substituted with one or more $R^{10}$ substituents;

$R^{10}$ is chosen from
1) OH,
2) $SR^7$,
3) $NH_2$,
4) C(O)OH,

5) $CONR^5R^6$,
6) phenyl optionally substituted with OH,
7) imidazole,
8) indole, or
9) $NHC(=NH)NH_2$;

$R^{11}$ is chosen from
1) halogen,
2) $NO_2$,
3) CN,
3) $C_1$-$C_6$ alkyl,
4) $C_3$-$C_7$ cycloalkyl,
5) haloalkyl,
6) $OR^7$,
7) $NR^8R^9$,
8) $SR^7$,
9) $CO^7$,
10) $C(O)OR^7$,
11) $S(O)_2R^7$,
12) $CONR^8R^9$, or
13) $S(O)_2NR^8R^9$;

$R^{12}$ is chosen from alkyl, heteroalkyl, cycloalkyl, aromatic and heteroaromatic esters;

or a salt thereof; or a probe thereof; or a prodrug thereof.

According to another aspect of the invention, there is provided a compound of formula:

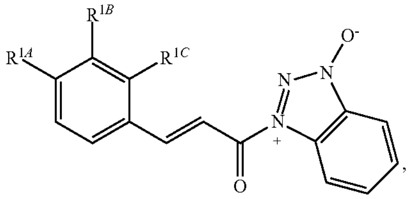

wherein $R^{1A}$ is $NO_2$ or H, $R^{1B}$ is H, $NO_2$, or Cl, and $R^{1C}$ is $NO_2$ or H. Preferably, $R^{1A}$ is $NO_2$, $R^{1B}$ is H and $R^{1C}$ is H.

From another aspect of the invention, there is provided a compound of formula:

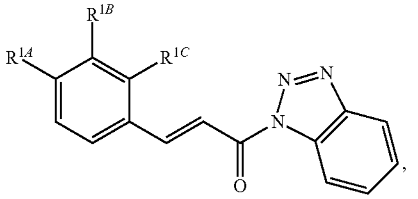

wherein $R^{1A}$ is $NO_2$, OMe, H, Me, Cl, NHBOC, NHFmoc, or MeOOC, $R^{1B}$ is H, OMe, Me or NHBOC, and $R^{1C}$ is OMe, H or Cl.

From yet another aspect of the invention, there is provided a compound of formula

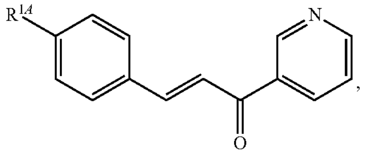

wherein $R^{1A}$ is $NO_2$, $NH_2$ or NHAc. Preferably, $R^{1A}$ is $NO_2$.

According to other aspects of the invention, also provided are compounds of formula:

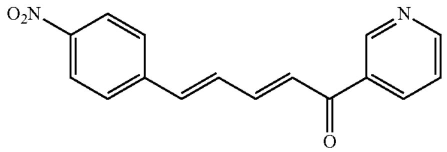

and

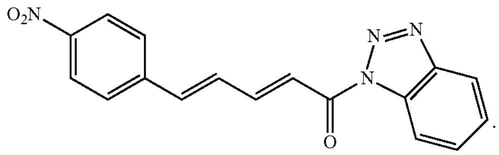

From a yet further aspect of the invention, there is provided a compound of the formula:

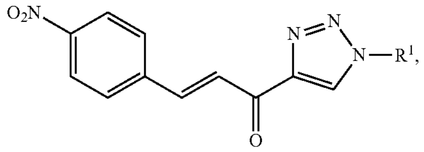

wherein $R^1$ is selected from a to o:

| | $R^1$ |
|---|---|
| a | 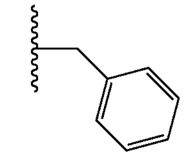 [SMILES: *Cc1ccccc1] |
| b | 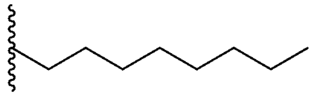 [SMILES: *CCCCCCCC] |
| c | 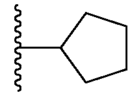 |
| d | 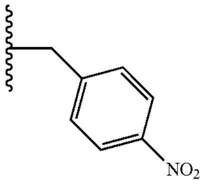 [SMILES: *Cc1ccc([N+](=O)[O-])cc1] |
| e | 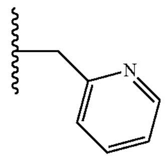 [SMILES: *Cc1ccccn1] |

-continued

| | $R^1$ |
|---|---|
| f | 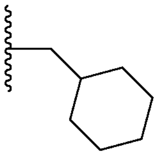 [SMILES: *CC1CCCCC1] |
| g | 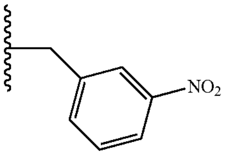 [SMILES: *Cc1cccc([N+](=O)[O-])c1] |
| h | 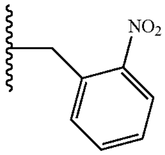 [SMILES: *Cc1ccccc1[N+](=O)[O-]] |
| i | 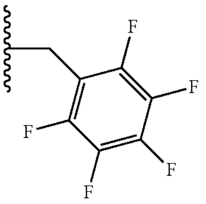 [SMILES: *Cc1c(F)c(F)c(F)c(F)c1F] |
| j | 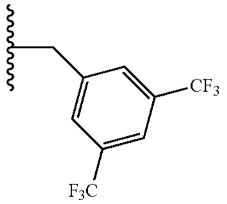 [SMILES: *Cc1cc(C(F)(F)F)cc(C(F)(F)F)c1] |
| k | 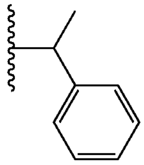 |
| l | 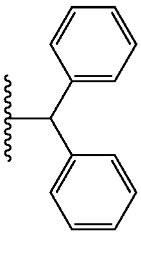 [SMILES: *C(c1ccccc1)c1ccccc1] |
| n | 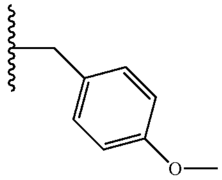 [SMILES: *Cc1ccc(OC)cc1] |
| o | H |

Preferably, $R^1$ is

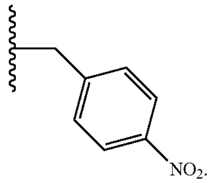 [SMILES: *Cc1ccc([N+](=O)[O-])cc1]

According to another aspect of the present invention there is provided an intermediate of Formula:

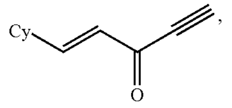

wherein Cy is as described above.

According to another aspect of the present invention there is provided a process for synthesizing a compound of Formula.

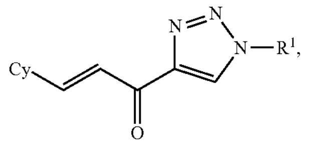

the process comprising: reacting the intermediate of Formula

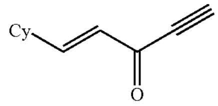

with $N_3$—$R^1$ in the presence of a copper (II) salt so as to produce a compound of Formula

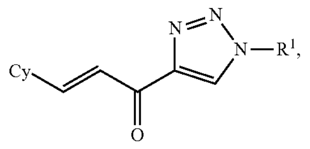

wherein Cy and $R^1$ are as defined above.

According to another aspect of the present invention, there is provided a pharmaceutical composition, the composition comprising a compound of Formula I or II or any other compounds described above, mixed with a pharmaceutically acceptable carrier, diluent or excipient.

In another aspect of the present invention, there is provided a method of preparing a pharmaceutical composition, the method comprising: mixing a compound of Formula I or II or any of the compounds described above, with a pharmaceutically acceptable carrier, diluent or excipient.

In another aspect of the present invention, there is provided a method of inhibiting transglutaminase activity in vitro or in vivo, the method comprising: contacting a cell with an amount of a compound of Formula I or II or any of the compounds described above, sufficient to inhibit the activity of the transglutaminase.

In another aspect of the present invention, there is provided a method of inhibiting transglutaminase activity, the method comprising: contacting a cell with an amount of a compound of Formula I or II or any of the compounds described above, as described above, sufficient to inhibit transglutaminase activity.

In another aspect of the present invention, there is provided a method of treating a disease state in which inhibition of transglutaminase is desired, the method comprising: administering to a subject in need thereof, a therapeutically effective amount of a pharmaceutical composition, as described above, so as to inhibit the activity of the transglutaminase, thereby treating the disease state.

In another aspect of the present invention, there is provided a method of identifying compounds that bind to a transglutaminase binding domain, the method comprising:

a) contacting a transglutaminase binding domain with a probe to form a probe: a transglutaminase binding domain complex, the probe being displaceable by a test compound;

b) measuring a signal from the probe so as to establish a reference level;

c) incubating the probe: transglutaminase binding domain complex with the test compound;

d) measuring the signal from the probe; and e) comparing the signal from step d) with the reference level, a modulation of the signal being an indication that the test compound binds to the transglutaminase binding domain, wherein the probe is a compound of Formula I or II or any of the compounds described above which is labeled with a detectable label or an affinity label.

In another aspect of the present invention, there is provided a method of identifying compounds that bind to a transglutaminase binding domain, the method comprising:

a) contacting a transglutaminase binding domain with a compound of Formula I or II or any of the compounds described above, or a probe to form either a probe or a compound: transglutaminase binding domain complex; and b) measuring the amount the probe or the compound bound to the transglutaminase binding domain.

In another aspect of the present invention, there is provided a method of measuring the binding of a transglutaminase binding domain to transglutaminase binding compound, the method comprising:

a) contacting a transglutaminase binding domain with a probe to form a probe: a transglutaminase binding domain complex;

b) washing non-bound transglutaminase; and c) extracting the bound transglutaminase from the probe either with a test compound or eluent, wherein the probe is a compound of Formula I or II or any of the compounds described above labeled with an affinity label.

Advantageously, by means of the compounds of the present invention, transglutaminase inhibition can be achieved. The use of cinnamoyl derivatives as transglutaminase inhibitors is novel. The inventors surprisingly discovered that cinnamoyl derivatives can serve as substrates, and that the aromatic amides embodied in the compositions of the present invention can inhibit transglutaminase strongly and selectively. In previous studies of structural elements required for TG2 substrate recognition, the distinctive ability of the Cbz protecting group to confer improved enzyme affinity was noted (Chica, R. A. et al *Protein Science* 2004, 13, 979). Investigation of the importance of the rigidity of the Cbz group led to the synthesis and biological evaluation of trans-cinnamoyl derivatives—that bound TG2 tightly. Although a number of cinnamoyl analogs have previously been found to exhibit inhibitory activity on various enzymes and proteins, including the fungal 17β-hydroxysteroid dehydrogenase (Gobec, S. et al *Bioorg. Med. Chem. Lett.* 2004, 14, 3933), the integrin αvβ3 receptors (Penning, T. D. et al *Bioorg. Med. Chem. Lett.* 2004, 14, 1471) and α-glucosidase (Adisakwattana, S. et al S. *Bioorg. Med. Chem. Lett.* 2004, 14, 1893), the cinnamoyl-based inhibitors of TGase of the present invention are new and some have been shown to be potent and selective TG2 inhibitors.

BRIEF DESCRIPTION OF THE DRAWINGS

These and other features of the invention will become more apparent from the following description in which reference is made to the appended drawings wherein:

FIG. 1 is a graph illustrating competitive inhibition by cinnamoyl amide 14a;

FIG. 6 is an illustration of an in vitro assay used to test compound 15a.

DETAILED DESCRIPTION

Definitions

Figure 1:
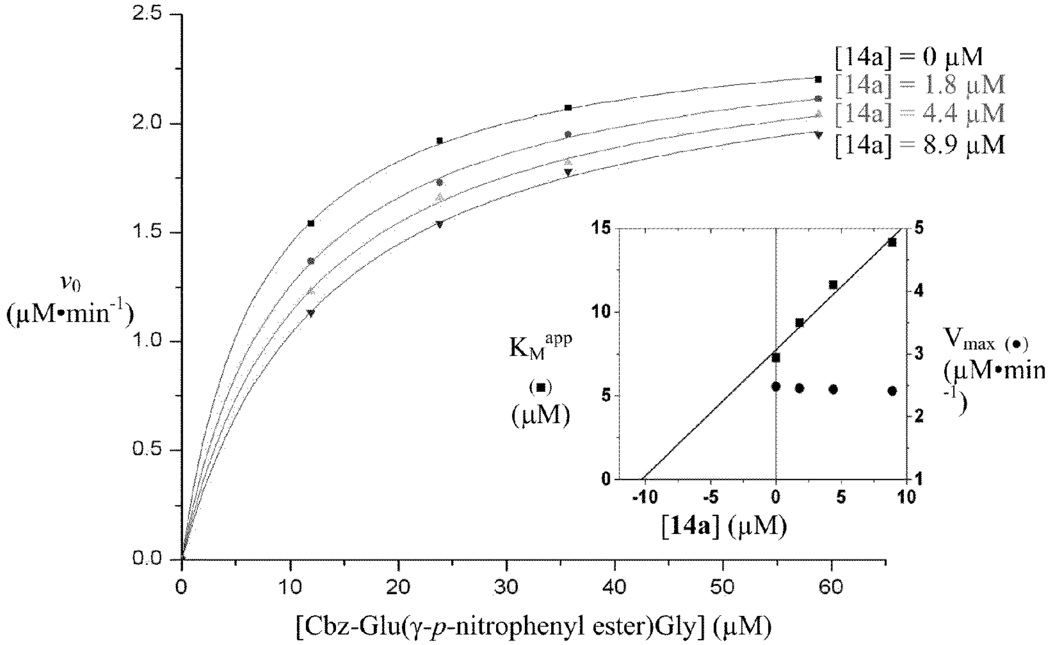

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_6$ as in $C_1$-$C_6$-alkyl is defined as including groups having 1, 2, 3, 4, 5 or 6 carbons in a linear or branched arrangement. Examples of alkyl as defined above include, but are not limited to, methyl, ethyl, n-propyl, i-propyl, n-butyl, t-butyl, i-butyl, pentyl and hexyl.

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6 or 7 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl.

As used herein, the term "halo" or "halogen" is intended to mean fluorine, chlorine, bromine and iodine.

As used herein, "amine" is intended to mean any group of organic compounds of nitrogen that may be considered as ammonia derivatives in which one or more hydrogen atoms have been replaced by a hydrocarbon radical. Examples of amines include, but are not limited to, ethylamine, allylamine, methylamine, phenylamine, propylamine, carbamide, ureas, arylamines, hetraryl amines, amine in context of heterocycle, benzylamine, and carbamate.

As used herein, the term “haloalkyl” is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term “aryl”, either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The fused aryls may be connected to another group either at a suitable position on the cycloalkyl ring or the aromatic ring. For example:

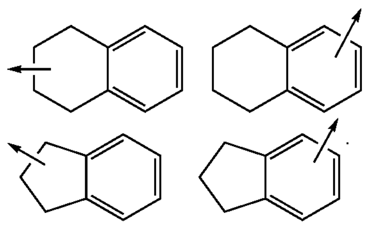

Arrowed lines drawn from the ring system indicate that the bond may be attached to any of the suitable ring atoms.

As used herein, the term “heteroaryl” is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, is oxazolyl, furazanyl, indolinyl, isoindolinyl, thiazolo[4,5-b]-pyridine, hydroxybenzotriazolyl, benzotriazoyl, triazoyl, and fluoroscein derivatives such as:

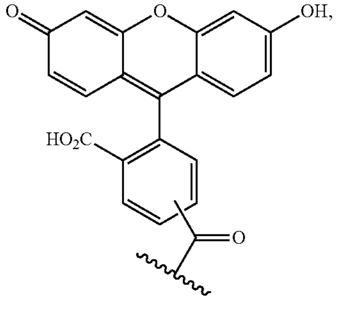

-continued

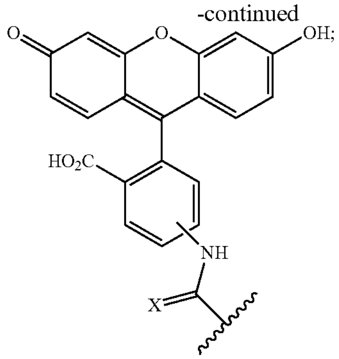

and rhodamine, dansyl and other fluorescent tags known to those skilled in the art.

As used herein, the term “heterocycle”, “heterocyclic” or “heterocyclyl” is intended to mean a 5, 6, or 7 membered non-aromatic ring system containing from 1 to 4 heteroatoms selected from the group consisting of O, N and S. Examples of aromatic heterocycles are described as heteroaromatic above. Examples of non-aromatic heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, pyrazolinyl, and biotinyl derivatives.

As used herein, the term “heterobicycle” either alone or in combination with another radical, is intended to mean a heterocycle as defined above fused to another cycle, be it a heterocycle, an aryl or any other cycle defined herein. Examples of such heterobicycles include, but are not limited to, coumarin, benzo[d][1,3]dioxole, 2,3-dihydrobenzo[b][1,4]dioxine and 3,4-dihydro-2H-benzo[b][1,4]dioepine.

As used herein, the term “detectable label” is intended to mean a group that may be linked to a compound of the present invention to produce a probe or to a transglutaminase binding domain, such that when the probe is associated with the transglutaminase binding domain, the label allows either direct or indirect recognition of the probe so that it may be detected, measured and quantified.

As used herein, the term “affinity tag” is intended to mean a ligand or group, which is linked to either a compound of the present invention or to a transglutaminase binding domain to allow another compound to be extracted from a solution to which the ligand or group is attached.

As used herein, the term “probe” is intended to mean a compound of Formula I or II which is labeled with either a detectable label or an affinity tag, and which is capable of binding, either covalently or non-covalently, to a transglutaminase binding domain. When, for example, the probe is non-covalently bound, it may be displaced by a test compound. When, for example, the probe is bound covalently, it may be used to form cross-linked adducts, which may be quantified and inhibited by a test compound.

As used herein, the term “optionally substituted with one or more substituents” or its equivalent term “optionally substituted with at least one substituent” is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Examples of protecting groups used throughout include, but are not limited to Alloc, Fmoc, Bn, Boc, CBz and $COCF_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

As used herein, the term "subject" is intended to mean humans and non-human mammals such as primates, cats, dogs, swine, cattle, sheep, goats, horses, rabbits, rats, mice and the like.

As used herein, the term "prodrug" is intended to mean a compound that may be converted under physiological conditions or by solvolysis to a biologically active compound of the present invention. Thus, the term "prodrug" refers to a precursor of a compound of the invention that is pharmaceutically acceptable. A prodrug may be inactive or display limited activity when administered to a subject in need thereof, but is converted in vivo to an active compound of the present invention. Typically, prodrugs are transformed in vivo to yield the compound of the invention, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers, which release the active compound of the invention in vivo when such prodrug is administered to a subject. Prodrugs of a compound of the present invention may be prepared by modifying functional groups present in the compound of the invention in such a way that the modifications are cleaved, either in routine manipulation or in vivo, to a parent compound of the invention.

As used herein, the term "pharmaceutically acceptable carrier, diluent or excipient" is intended to mean, without limitation, any adjuvant, carrier, excipient, glidant, sweetening agent, diluent, preservative, dye/colorant, aerosol spray, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethylene glycol matrix, which is acceptable for use in the subject, preferably humans.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

As used herein, the term "transglutaminase inhibition" is intended to mean the action of a compound of the present invention upon a transglutaminase-binding domain, resulting in a decrease in the activity of the enzyme, relative to its activity in the absence of the compound.

As used herein, the term "activity" is intended to mean the ability of the enzyme to catalyze physiologically relevant reactions, which include but are not limited to peptide or protein transamidation and cross-linking, protein- or peptide-bound glutamine to glutamate hydrolysis, GTP hydrolysis or NO fixation.

As used herein, the term "therapeutically effective amount" is intended to mean an amount of a compound of Formula I or II which, when administered to a subject is sufficient to effect treatment for a disease-state in which inhibition of transglutaminase is desired. The amount of the compound of Formula I or II will vary depending on the compound, the condition and its severity, and the age of the subject to be treated, but can be determined routinely by one of ordinary skill in the art having regard to his own knowledge and to this disclosure.

As used herein, the term "treating" or "treatment" is intended to mean treatment of a disease-state in which inhibition of transglutaminase is desired, as disclosed herein, in a subject, and includes, for example: (i) preventing a disease or condition, in which inhibition of transglutaminase is desired, from occurring in a subject, in particular, when such mammal is predisposed to the disease or condition but has not yet been diagnosed as having it; (ii) inhibiting a disease or condition associated with transglutaminase activity, i.e., arresting its development; or (iii) relieving a disease or condition associated with tranglutaminase activity, i.e., causing regression of the condition.

As used herein, the term "$IC_{50}$" is intended to mean an amount, concentration or dosage of a particular compound of the present invention that achieves a 50% inhibition of a maximal response measured under the same experimental conditions but in the absence of the compound.

As used herein, the term "$EC_{50}$" is intended to mean an amount, concentration or dosage of a particular compound of the present invention that achieves a 50% inhibition of cell survival measured under the same experimental conditions but in the absence of the compound.

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form.

Alternatively specific enantiomers may be synthesized by asymmetric synthesis using optically active reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

I: Compounds

The present invention concerns compounds of Formula I (Cy-A=B-G) or Formula II (Cy-=-G) and their use as transglutaminase inhibitors.

One subset of compounds of the present invention, comprises compounds according to the Formula:

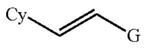

wherein

Cy is a ring system chosen from 1) aryl,
2) heteroaryl,
3) heterocyclyl, or
4) heterobicyclyl, wherein the aryl, the heteroaryl, the heterocyclyl and the heterobicyclyl are optionally substituted with one or more $R^1$ substituents;

G is chosen from

1)

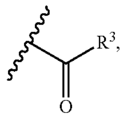

2)

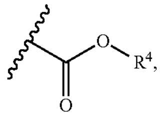

or

-continued

3)

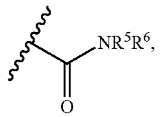

$R^1$ is chosen from 1) halogen,
2) $NO_2$,
3) CN,
4) $C_1$-$C_6$ alkyl,
5) $C_3$-$C_7$ cycloalkyl,
6) haloalkyl,
7) $OR^7$,
8) $NR^8R^9$,
9) $SR^7$,
10) $COR^7$,
11) $C(O)OR^7$,
12) $S(O)_2R^7$,
13) $(CONR^8R^9)_{1-3}$,
14) $S(O)_2NR^8R^9$,
15) aryl,
16) heteroaryl,
17) heterocyclyl, or
18) heterobicyclyl, wherein the alkyl and the cycloalkyl are optionally substituted with one or more $R^{11}$ substituents;

$R^2$ is chosen from

1) H,
2) $C_1$-$C_6$ alkyl,
3) $C_3$-$C_7$ cycloalkyl,
4) haloalkyl,
5) aryl,
6) heteroaryl,
7) heterocyclyl,
8) heterobicyclyl,
9) $OR^7$,
10) $SR^7$,
11) halogen,
12) amine,
13) thioether, or
14) $NR^8R^9$, wherein the aryl, the heteroaryl, the heterocyclyl and the heterobicyclyl are optionally substituted with one or more $R^1$ substituents;

$R^3$ is chosen from

1) $C_1$-$C_6$ alkyl,
2) $C_3$-$C_7$ cycloalkyl,
3) aryl,
4) heteroaryl,
5) heterocyclyl, or
6) heterobicyclyl, wherein the aryl, the heteroaryl, the heterocyclyl, and the heterobicylyl are optionally substituted with one or more $R^1$ substituents;

$R^4$ is chosen from

1) $C_1$-$C_6$ alkyl,
2) haloalkyl,
3) $C_3$-$C_7$ cycloalkyl,
4) aryl,
5) heteroaryl,
6) heterocyclyl, or
7) heterobicyclyl, wherein the alkyl and the cycloalkyl are substituted with one or more $R^3$ substituents; and wherein the aryl, the heteroaryl, the heterocyclyl, and the heterobicyclyl are optionally substituted with one or more $R^1$ substituents;

$R^5$ and $R^6$ are independently chosen from

1) H,
2) $C_1$-$C_6$ alkyl,
3) $C_3$-$C_7$ cycloalkyl,
4) haloalkyl,
5) aryl,
6) heteroaryl,
7) heterocyclyl,
8) heterobicyclyl,
9) $NR^8R^9$, or
10) $CONR^8R^9$, or $R^5$ and $R^6$ together with the nitrogen atom to which they are bonded form a five, six or seven membered heterocyclic ring optionally substituted with one or more $R^1$ substituents; wherein the alkyl and the cycloalkyl are optionally substituted with one or more $R^3$ substituents; and wherein the aryl, the heteroaryl, the heterocyclyl, and the heterobicyclyl are optionally substituted with one or more $R^1$ substituents;

$R^7$ is chosen from

1) H,
2) $C_1$-$C_6$ alkyl,
3) aryl,
4) heteroaryl,
5) heterocyclyl, or
6) heterobicyclyl;

$R^8$ and $R^9$ are independently chosen from

1) H,
2) $C_1$-$C_6$ alkyl,
3) $COOR^{12}$,
4) Fmoc,
5) Boc,
6) $C(O)C_1$-$C_6$ alkyl,
7) carbonyl aryl,
8) carbonyl heteroaryl,
9) $SO_2$Aryl,
10) $SO_2$heteroaryl,
11) $PO_2$alkyl,
12) $PO_2$Aryl, or
13) $CONR^7R^8$, or $R^8$ and $R^9$ together with the nitrogen atom to which they are bonded form a five, six or seven membered heterocyclic ring; wherein the alkyl is optionally substituted with one or more $R^{10}$ substituents;

$R^{10}$ is chosen from

1) OH,
2) $SR^7$,
3) $NH_2$,
4) C(O)OH,
5) $CONR^5R^6$,
6) phenyl optionally substituted with OH,
7) imidazole,
8) indole, or
9) $NHC({=}NH)NH_2$;

$R^{11}$ is chosen from 1) halogen,
2) $NO_2$,
3) CN,
3) $C_1$-$C_6$ alkyl,
4) $C_3$-$C_2$ cycloalkyl,
5) haloalkyl,
6) $OR^7$,
7) $NR^8R^9$,
8) $SR^7$,
9) $COR^7$,
10) $C(O)OR^7$,
11) $S(O)_2R^7$,
12) $CONR^8R^9$, or
13) $S(O)_2NR^8R^9$;

$R^{12}$ is chosen from alkyl, heteroalkyl, cycloalkyl, aromatic and heteroaromatic esters;

or a salt thereof; or a probe thereof; or a prodrug thereof.

Another subset of the aforesaid compounds, comprises compounds according to the Formula:

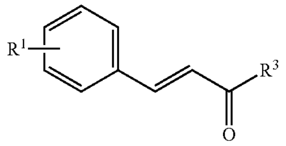

wherein $R^1$ is chosen from 1) halogen,
2) $NO_2$,
3) CN,
4) $C_1$-$C_6$ alkyl,
5) $C_3$-$C_7$ cycloalkyl,
6) haloalkyl,
7) $OR^7$,
8) $NR^8R^9$,
9) $SR^7$,
10) $COR^7$,
11) $C(O)OR^7$,
12) $S(O)_2R^7$,
13) $(CONR^8R^9)_{1-3}$,
14) $S(O)_2NR^8R^9$,
15) aryl,
16) heteroaryl,
17) heterocyclyl, or
18) heterobicyclyl, wherein the alkyl and the cycloalkyl are optionally substituted with one or more $R^{11}$ substituents;

$R^2$ is chosen from

1) H,
2) $C_1$-$C_6$ alkyl,
3) $C_3$-$C_7$ cycloalkyl,
4) haloalkyl,
5) aryl,
6) heteroaryl,
7) heterocyclyl,
8) heterobicyclyl,
9) $OR^7$,
10) $SR^7$,
11) halogen,
12) amine,
13) thioether, or
14) $NR^8R^9$, wherein the aryl, the heteroaryl, the heterocyclyl and the heterobicyclyl are optionally substituted with one or more $R^1$ substituents;

$R^3$ is chosen from

1) $C_1$-$C_6$ alkyl,
2) $C_3$-$C_7$ cycloalkyl,
3) aryl,
4) heteroaryl,
5) heterocyclyl, or
6) heterobicyclyl, wherein the aryl, the heteroaryl, the heterocyclyl, and the heterobicylyl are optionally substituted with one or more $R^1$ substituents;

$R^4$ is chosen from

1) $C_1$-$C_6$ alkyl,
2) haloalkyl,
3) $C_3$-$C_7$ cycloalkyl,
4) aryl,
5) heteroaryl,
6) heterocyclyl, or
7) heterobicyclyl, wherein the alkyl and the cycloalkyl are substituted with one or more $R^3$ substituents; and wherein the aryl, the heteroaryl, the heterocyclyl, and the heterobicyclyl are optionally substituted with one or more $R^1$ substituents;

$R^5$ and $R^6$ are independently chosen from

1) H,
2) $C_1$-$C_6$ alkyl,
3) $C_3$-$C_7$ cycloalkyl,
4) haloalkyl,
5) aryl,
6) heteroaryl,
7) heterocyclyl,
8) heterobicyclyl,
9) $NR^8R^9$, or
10) $CONR^8R^9$, or $R^5$ and $R^6$ together with the nitrogen atom to which they are bonded form a five, six or seven membered heterocyclic ring optionally substituted with one or more $R^1$ substituents; wherein the alkyl and the cycloalkyl are optionally substituted with one or more $R^3$ substituents; and wherein the aryl, the heteroaryl, the heterocyclyl, and the heterobicyclyl are optionally substituted with one or more $R^1$ substituents;

$R^7$ is chosen from

1) H,
2) $C_1$-$C_6$ alkyl,
3) aryl,
4) heteroaryl,
5) heterocyclyl, or
6) heterobicyclyl;

$R^8$ and $R^9$ are independently chosen from

1) H,
2) $C_1$-$C_6$ alkyl,
3) $COOR^{12}$,
4) Fmoc,
5) Boc,
6) $C(O)C_1$-$C_6$ alkyl,
7) carbonyl aryl,
8) carbonyl heteroaryl,
9) $SO_2$Aryl,
10) $SO_2$heteroaryl,
11) $PO_2$alkyl,
12) $PO_2$Aryl, or
13) $CONR^7R^8$, or $R^8$ and $R^9$ together with the nitrogen atom to which they are bonded form a five, six or seven membered heterocyclic ring; wherein the alkyl is optionally substituted with one or more $R^{10}$ substituents;

$R^{10}$ is chosen from

1) OH,
2) $SR^7$,
3) $NH_2$,
4) C(O)OH,
5) $CONR^5R^6$,
6) phenyl optionally substituted with OH,
7) imidazole,
8) indole, or
9) $NHC(=NH)NH_2$;

$R^{11}$ is chosen from 1) halogen,
2) $NO_2$,
3) CN,
3) $C_1$-$C_6$ alkyl,
4) $C_3$-$C_7$ cycloalkyl,
5) haloalkyl,
6) $OR^7$,
7) $NR^8R^9$,
8) $SR^7$,
9) $COR^7$,
10) $C(O)OR^7$,
11) $S(O)_2R^7$,
12) $CONR^8R^9$, or
13) $S(O)_2NR^8R^9$;

$R^{12}$ is chosen from alkyl, heteroalkyl, cycloalkyl, aromatic and heteroaromatic esters;

or a salt thereof; or a probe thereof; or a prodrug thereof.

II: Utilities

The compounds of the present invention are useful as transglutaminase inhibitor compounds and as such the compounds, compositions and method of the present invention include application to the cells or subjects afflicted with or having a predisposition towards developing a particular disease state, for which inhibition of transglutaminase is desired. Unregulated transglutaminase activity has been linked to at least the following pathological conditions: acne, cataracts, immune system diseases, psoriasis, neuropathy, neurodegenerative disease such as, for example, Alzheimer's disease, Huntington's disease, Parkinson's disease, Celiac disease, cancer metastasis, inflammation, fibrosis, diabetes, autoimmune diseases, lamellar ichthyosis, psoriasis, supranuclear palsy, renal failure (Siegel, M et al. *Pharmacology & Therapeutics* 2007 115, 232; De Young et al, *J. Invest. Dermatol.* 1984, 82, 275; Candi, E. et al, *Proc. Natl. Acad. Sci. U.S.A.* 1998, 95, 2067; Dalziel, K. et al, *J. Exp. Pathol.* 1984, 65, 107; Azari, P. et al. *Curr. Eye. Res.* 1981, 463; Fesus, L. *Surv. Immunol. Res.* 1982, 1, 297; Bernard, B. A. et al. *Brit. J. Dermatol.* 1986, 114, 279; Schroeder, W. T. et al, *J. Invest. Dermatol.* 1992, 99, 27; Selkoe, D. J. et al. *Science* 1982, 215, 1243; Selkoe, D. J. et al. *Proc. Natl. Acad. Sci. U.S.A.* 1982, 79, 6070; Schlaepfer, W. Biological Aspects of Alzheimer's Disease; Katzman, R., Ed.; Cold Spring Harbor Laboratory: Cold Spring Harbor, N.Y. 1983; pp 107; Farmer, P. M. et al *J. Neuropathol. Exp. Neurol.* 1976, 35, 367; Amendola, A. et al *FEBS Lett.* 1994, 339, 258; Benzinger, T. L. S. et al S. C. *Proc. Natl. Acad. Sci. U.S.A.* 1998, 95, 13407; Norlund, M. A. et al *Brain Res.* 1999, 851, 154; Dedeoglu, A. et al *J. Neurosci.* 2002, 22, 8942; Mastroberardino, P. G. et al *Cell Death Differ.* 2002, 9, 873; Mastroberardino, P. G. et al *Cell Death Differ.* 2002, 9, 873; Piper, J. L. et al *Biochemistry* 2002, 41, 386; El Nahas A M et al, *Clinical Practice* 2004, 97(3), 108).

Thus, the compounds, compositions and methods of the present invention can be used to treat at least these conditions, namely acne, cataracts, immune system diseases, psoriasis, neuropathy, neurodegenerative disease such as, for example, Alzheimer's disease, Huntington's disease, Parkinson's disease, Celiac disease, cancer metastasis, inflammation, fibrosis, diabetes, autoimmune diseases, lamellar ichthyosis, psoriasis, supranuclear palsy, renal failure, to name a few.

The treatment involves administration to a subject in need thereof a compound of the present invention or a pharmaceutically acceptable salt thereof, or a pharmaceutical composition comprising a pharmaceutical carrier and a therapeutically effective amount of a compound of the present invention, or a pharmaceutically acceptable salt thereof.

The compounds of the present invention, or their pharmaceutically acceptable salts or their prodrugs, may be administered in pure form or in an appropriate pharmaceutical composition, and can be carried out via any of the accepted modes of Galenic pharmaceutical practice.

The pharmaceutical compositions of the present invention can be prepared by mixing a compound of the present invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral (subcutaneous injections, intravenous, intramuscular, intrasternal injection or infusion techniques), sublingual, ocular, rectal, vaginal, and intranasal. Pharmaceutical compositions of the present invention are formulated so as to allow the active ingredients contained therein to be bioavailable upon administration of the composition to a subject. Compositions that will be administered to a subject or patient take the form of one or more dosage units, where for example, a tablet may be a single dosage unit, and a container of a compound of the present invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the present invention, or a pharmaceutically acceptable salt thereof, for treatment of a disease-state as described above.

A pharmaceutical composition of the present invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example inhalatory administration.

For oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil such as soybean or vegetable oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the present invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediamine tetraacetic acid; buffers such as acetates, citrates or phosphates and agents for the adjustment of tonicity such as sodium chloride or dextrose. Solubilization agents may include cyclodextrins such as hydroxypropyl-beta-cyclodextrin. The parenteral preparation can be enclosed in ampoules, disposable syringes or multiple dose vials made of glass or plastic. An injectable pharmaceutical composition is preferably sterile.

A liquid pharmaceutical composition of the present invention used for either parenteral or oral administration should contain an amount of a compound of the present invention such that a suitable dosage will be obtained. Typically, this amount is at least 0.01% of a compound of the present invention in the composition. When intended for oral administration, this amount may be varied to be between 0.1 and about 70% of the weight of the composition. For parenteral usage, compositions and preparations according to the present invention are prepared so that a parenteral dosage unit contains between 0.01 to 1% by weight of the compound of the present invention.

The pharmaceutical composition of the present invention may be used for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the present invention from about 0.1 to about 10% w/v (weight per unit volume).

The pharmaceutical composition of the present invention may be used for rectal administration in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the present invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present invention in solid or liquid form may include an agent that binds to the compound of the present invention and thereby assists in the delivery of the compound. Suitable agents that may act in this capacity include, but are not limited to, a monoclonal or polyclonal antibody, a protein or a liposome.

The pharmaceutical composition of the present invention may consist of dosage units that can be administered as an aerosol. The term aerosol is used to denote a variety of systems ranging from those of colloidal nature to systems comprising pressurized packages. Delivery may be by a liquefied or compressed gas or by a suitable pump system that dispenses the active ingredients. Aerosols of compounds of the present invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the present invention may be prepared by methodology well known in the pharmaceutical art. For example, a pharmaceutical composition intended to be administered by injection can be prepared by admixing a compound of the present invention with sterile, distilled water so as to form a solution. A surfactant may be added to facilitate the formation of a homogeneous solution or suspension. Surfactants are compounds that non-covalently interact with the compound of the present invention so as to facilitate dissolution or homogeneous suspension of the compound in the aqueous delivery system.

The compounds of the present invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose may be from about 0.1 mg to about 40 mg/kg of body weight per day or twice per day of a compound of the present invention, or a pharmaceutically acceptable salt thereof.

III: Screening Assays

The compounds of the present invention may also be used in a method to screen for other compounds that bind to a transglutaminase-binding domain. Generally speaking, to use the compounds of the invention in a method of identifying compounds that bind to a transglutaminase binding domain, the transglutaminase is bound to a support, and a compound of the invention is added to the assay. Alternatively, the compound of the invention may be bound to the support and the transglutaminase is added.

There are a number of ways in which to determine the binding of a compound of the present invention to the transglutaminase binding domain. In one way, the compound of the invention, may be fluorescently or radioactively labeled and binding determined directly. For example, this may be done by attaching the transglutaminase to a solid support, adding a detectably labeled compound of the invention, washing off excess reagent, and determining whether the amount of the detectable label is that present on the solid support. Numerous blocking and washing steps may be used, which are known to those skilled in the art.

In some cases, only one of the components is labeled. For example, specific residues in the transglutaminase binding domain may be labeled. Alternatively, more than one component may be labeled with different labels; for example, using $I^{125}$ for the transglutaminase binding domain, and a fluorescent label for the probe.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity. The compounds may be capable of directly or indirectly altering the transglutaminase biological activity.

Drug candidates can include various chemical classes, although typically they are small organic molecules having a molecular weight of more than 100 and less than about 2,500 Daltons. Candidate agents typically include functional groups necessary for structural interaction with proteins, for example, hydrogen bonding and lipophilic binding, and typically include at least an amine, carbonyl, hydroxyl, ether, or carboxyl group. The drug candidates often include cyclical carbon or heterocyclic structures and/or aromatic or polyaromatic structures substituted with one or more functional groups.

Drug candidates can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Competitive screening assays may be done by combining a transglutaminase binding domain and a probe to form a probe:transglutaminase binding domain complex in a first sample followed by adding a test compound from a second sample. The binding of the test is determined, and a change, or difference in binding between the two samples indicates the presence of a test compound capable of binding to the transglutaminase binding domain and potentially modulating the trans glutaminase's activity.

In one case, the binding of the test compound is determined through the use of competitive binding assays. In this embodiment, the probe is labeled with an affinity label such as biotin. Under certain circumstances, there may be competitive binding between the test compound and the probe, with the probe displacing the candidate agent.

In one case, the test compound may be labeled. Either the test compound, or a compound of the present invention, or both, is added first to the transglutaminase binding domain for a time sufficient to allow binding to form a complex.

Formation of the probe: transglutaminase binding domain complex typically require incubations of between 4° C. and 40° C. for between 10 minutes to about 1 hour to allow for high-throughput screening. Any excess of reagents are generally removed or washed away. The test compound is then added, and the presence or absence of the labeled component is followed, to indicate binding to the transglutaminase binding domain.

In one case, the probe is added first, followed by the test compound. Displacement of the probe is an indication the test compound is binding to the transglutaminase binding domain and thus is capable of binding to, and potentially modulating, the activity of the transglutaminase. Either component can be labeled. For example, the presence of probe in the wash solution indicates displacement by the test compound. Alternatively, if the test compound is labeled, the presence of the probe on the support indicates displacement.

In one case, the test compound may be added first, with incubation and washing, followed by the probe. The absence of binding by the probe may indicate the test compound is bound to the transglutaminase binding domain with a higher affinity. Thus, if the probe is detected on the support, coupled with a lack of test compound binding, may indicate the test compound is capable of binding to the transglutaminase binding domain.

Modulation is tested by screening for a test compound's ability to modulate the activity of transglutaminase and includes combining a test compound with a transglutaminase binding domain, as described above, and determining an alteration in the biological activity of the transglutaminase. Therefore in this case, the test compound should both bind to the transglutaminase binding domain (although this may not be necessary), and alter its biological activity as defined herein.

Positive controls and negative controls may be used in the assays. All control and test samples are performed multiple times to obtain statistically significant results. Following incubation, all samples are washed free of non-specifically bound material and the amount of bound probe determined. For example, where a radiolabel is employed, the samples may be counted in a scintillation counter to determine the amount of bound compound.

Typically, the signals that are detected in the assay may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; a chemiluminescent label such as luciferase; colorimetric labels; enzymatic markers; or radioisotopes such as tritium, $I^{125}$ and the like.

Affinity tags, which may be useful in performing the screening assays of the present invention include biotin, polyhistidine and the like.

EXAMPLES

Figure 2:
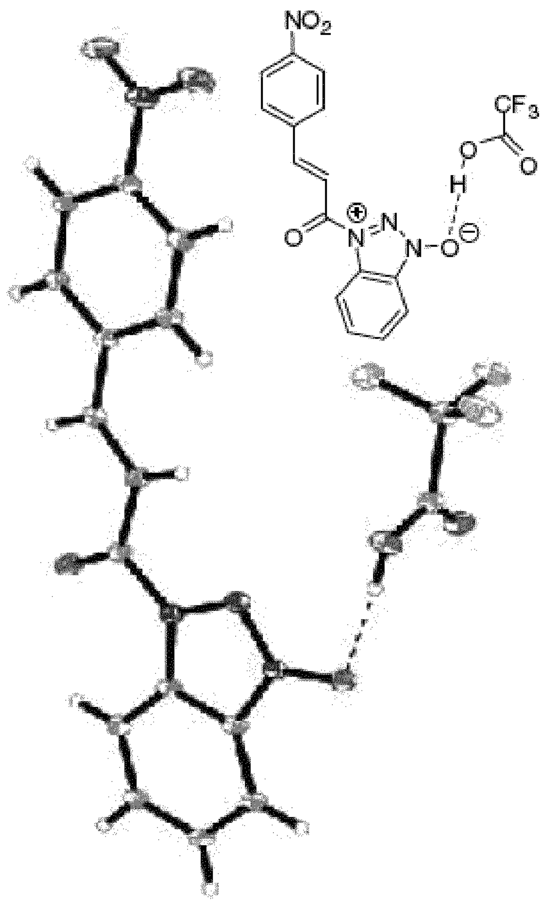
FIG. 2 is an X-ray structure of p-nitrocinnamoyl oxybenzotriazolyl amide with trifluoracetic acid.

Synthesis of Compounds 14a-c, 14l, 15a, 15d-k, 15m-q, 30a, 30r, 30t, 37a, 38a and Methodology Cinnamoyl benzotriazolyl amides 14a-c, 14l, 15a, 15d-k and 15m-q were initially studied as potential TG2 inhibitors. The coupling of various trans-cinnamic acid derivatives with benzotriazole and hydroxybenzotriazole was performed using diisopropylcarbodiimide (DIC) and dimethylaminopyridine (DMAP) in dimethylformamide (DMF) overnight at room temperature. Although the resulting product mixture could be purified by diluting in ethyl acetate (EtOAc) and washing successively with NaOH, HCl and brine, significant amounts of product were lost during the washing steps. For this reason, after removal of the EtOAc phase, the substituted cinnamoyl benzotriazolyl amides were isolated by trituration or by flash column chromatography, in 12-70% isolated yields (Scheme 1). The structure of amide 14a was confirmed by X-ray crystallographic analysis and showed that N-acylation of the hydroxybenzotriazole moiety had occurred, instead of formation of its ester counterpart (FIG. 2). trans-Cinnamic acids that were not commercially available were typically prepared in 37-74% yields by the Wittig olefination of the corresponding substituted benzaldehyde with (tert-butoxycarbonylmethyl)triphenylphosphonium bromide in tetrahydrofuran (THF) using potassium bis(trismethylsilyl) amide (KHMDS) as a base at room temperature. (Scheme 1).

Scheme 1. Synthesis of the substituted cinnamoyl benzotriazolyl amides and oxybenzotriazolyl amides

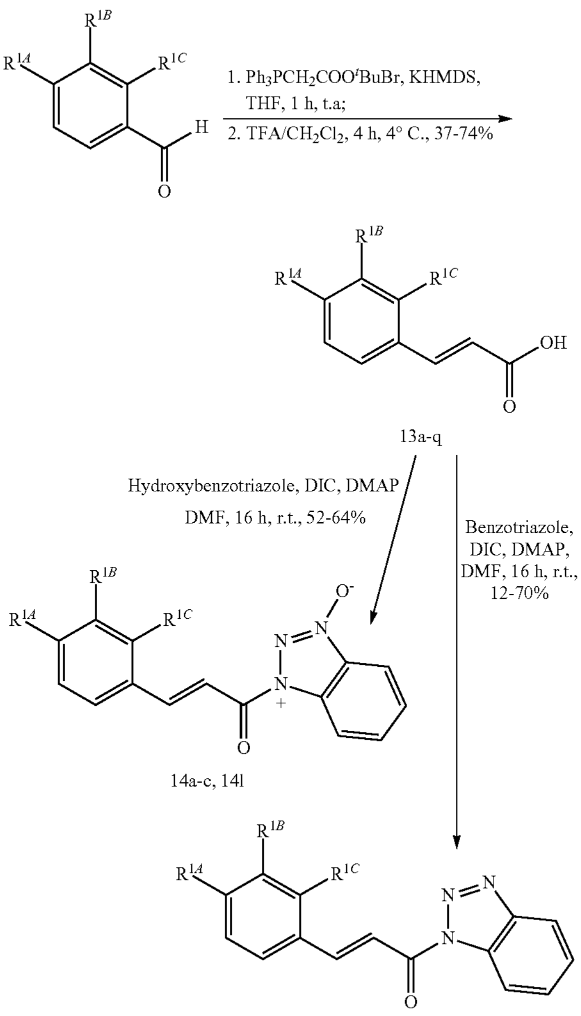

13a-q 14a-c, 14l 15a, 15d-k, 15m-q

| amide | $R^{1A}$ | $R^{1B}$ | $R^{1C}$ |
|---|---|---|---|
| 14a | $NO_2$ | H | H |
| 14b | H | $NO_2$ | H |
| 14c | H | H | $NO_2$ |
| 14l | H | Cl | H |
| 15a | $NO_2$ | H | H |
| 15d | OMe | H | H |
| 15e | H | OMe | H |
| 15f | H | H | OMe |
| 15g | Me | H | H |
| 15h | H | Me | H |
| 15i | H | H | Me |
| 15j | H | H | H |
| 15k | Cl | H | H |
| 15m | H | H | Cl |
| 15n | NHBOC | H | H |
| 15o | H | NHBOC | H |
| 15p | NHFmoc | H | H |
| 15q | COOMe | H | H |

Amino substituted cinnamoyl benzotriazole amides (15n-p) were synthesized by reduction of the corresponding nitro-cinnamoyl tert-butyl ester using tin (II) chloride ($SnCl_2$) in ethanol (Bellamy, F. D.; Ou, K., *Tetrahedron Lett.* 1984, 25, 839). The crude anilines 13r and 13s were acylated with FmocCl or $(BOC)_2O$ to provide N-protected aminocinnamic acids 13n-p. These N-protected aminocinnamic acids were used without further purification and treated with benzotriazole under the same coupling conditions as described above (Scheme 2).

Scheme 2. Synthesis of the amide-substituted cinnamoyl benzotriazolyl amides

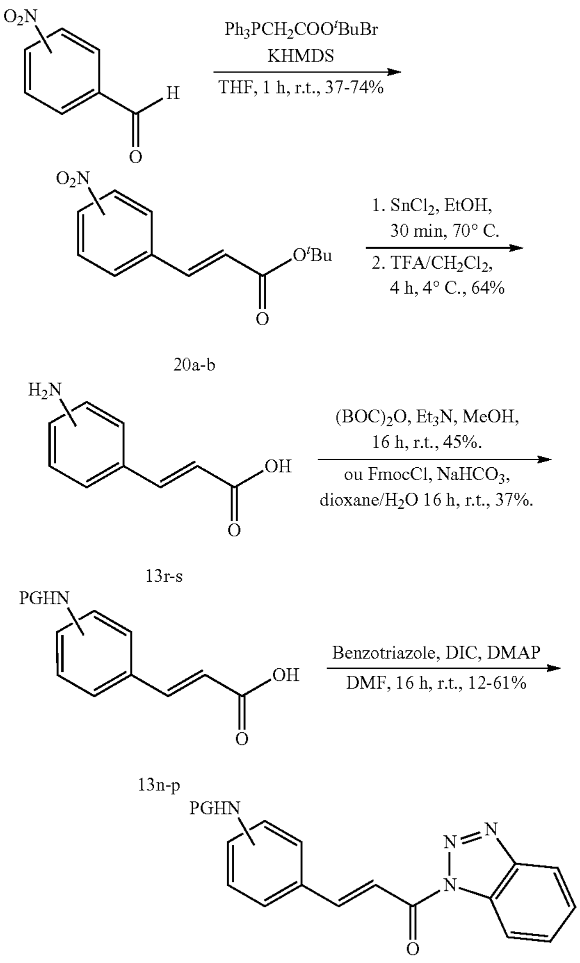

20a-b 13r-s 13n-p 15n-p

PGHN = 4-BOCNH n
3-BOCNH o
4-FmocNH p

Azachalcones 30a, 30r and 30t were synthesized as a second subclass of inhibitor candidates by aldol condensation of different substituted benzaldehydes with 3-acetylpyridine using potassium hydroxide in a 50/50 $MeOH/H_2O$ solution (Nelson, A. T.; Houlihan, W. J., The Aldol Condensation in Organic Reactions. John Wiley and Sons: New York, 1968; p 44). For example, p-nitro-azachalcone 30a precipitated from the reaction mixture and was obtained in pure form after simple filtration, in 73% yield. p-Nitro-azachalcone 30a was reduced with SnCl2 (Bellamy, F. D.; Ou, K., *Tetrahedron Lett.* 1984, 25, 839) to provide p-amino-azachalcone 30r which was then acetylated with a solution of 40% acetic anhydrous/pyridine at room temperature over 1 hour (Scheme 3).

Scheme 3. Synthesis of the substituted azachalcones

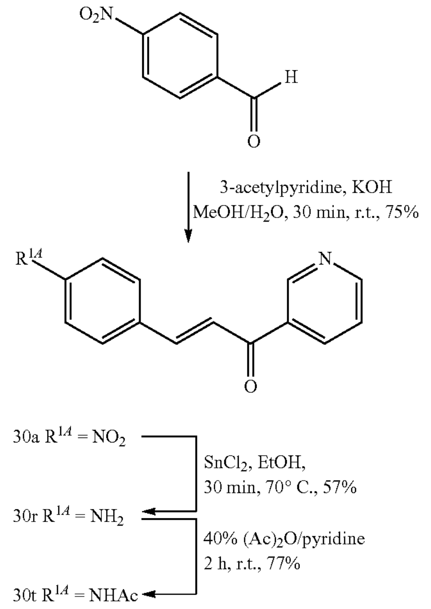

For comparison, cinnamate 19a and cinnamides 18a, 21a-27a were synthesized from p-nitrocinnamic acid by activation with p-nitrophenyl chloroformate, triethylamine and DMAP in acetonitrile to form ester 17a that precipitated (Gagnon, P. et al *Tetrahedron Lett.* 2002, 43, 7717). After filtration and washing with acetonitrile, p-nitrophenyl ester 17a was dissolved in dimethylformamide and reacted with the specified alcohol or amine in the presence of $Et_3N$ to provide the respective ester 19a and amides 18a, 21a-27a after purification by flash chromatography (Scheme 4). Carbamate 34a was synthesized from p-nitrophenyl chloroformate and benzotriazole using $Et_3N$ and DMAP in dichloromethane overnight at room temperature.

Scheme 4. Synthesis of different amides and esters of the p-nitrocinnamic acid

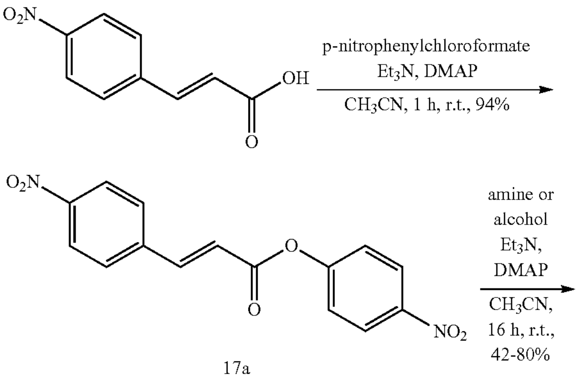

17a

-continued

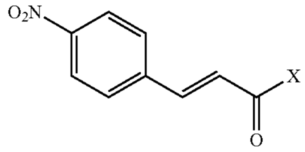

18a-27a, 29a

| | X |
| --- | --- |
| 18a | 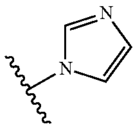 |
| 19a | 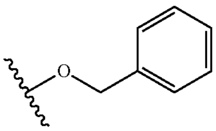 [SMILES: *OCc1ccccc1] |
| 20a | 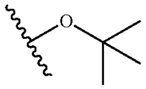 |
| 21a | 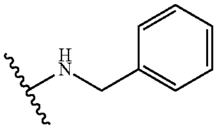 [SMILES: *NCc1ccccc1] |
| 22a | 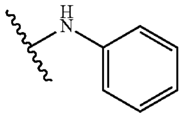 |
| 23a | 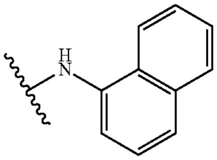 [SMILES: *Nc1cccc2ccccc12] |
| 24a | 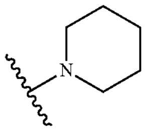 [SMILES: *N1CCCCC1] |
| 25a | 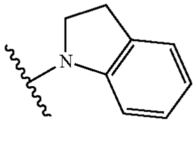 [SMILES: *N1CCc2ccccc21] |
| 26a | 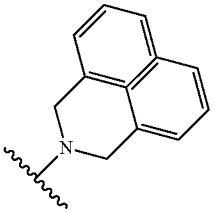 |

-continued

| | |
| --- | --- |
| 27a | 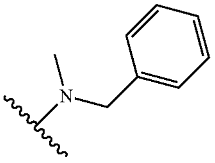 [SMILES: *N(C)Cc1ccccc1] |

The coumarin derivative 3-((E)-3-(4-nitrophenyl)acryloyl)-2H-chromen-2-one (28a) was synthesized from treatment of p-nitrobenzaldehyde with 3-(triphenylphosphinylacetenyl)coumarin (36) in toluene overnight at room temperature. Under these conditions, the product was found to precipitate and simple filtration provided the pure product as a yellow solid in 36% isolated yield. 3-(Triphenylphosphinylacetenyl)coumarin (36) was prepared from 3-(triphenylphosphimylacetyl)coumarin bromide (35) using potassium carbonate in 2:1 EtOH/$H_2O$ to give the product as a yellow crystalline solid after extraction, in 95% isolated yield. The required precursor 35 was prepared by nucleophilic displacement of 3-bromoacetylcoumarin with triphenylphosphine in dichloromethane which gave a yellow crystalline solid in quantitative yield (Scheme 5).

Scheme 5. Synthesis of 3-((E)-3-(4-nitrophenyl)acryloyl)-2H-chromen-2-one (28a)

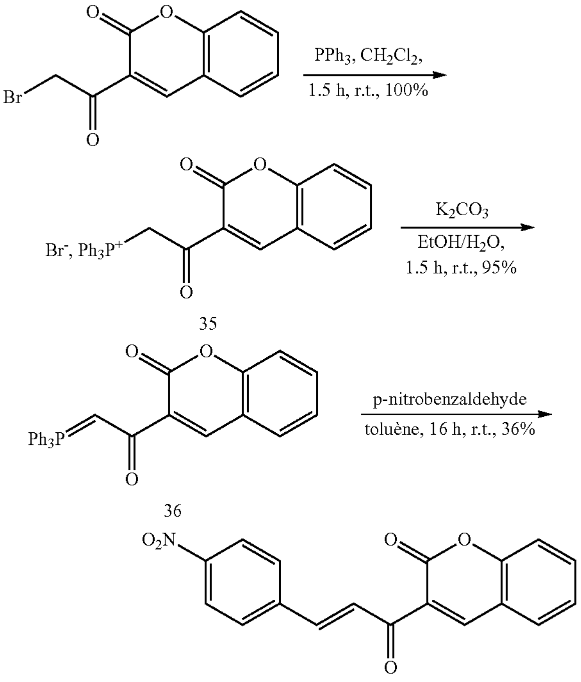

35

36

28a

Dienones 37a and 38a were synthesized from p-nitrocinnamaldehyde following similar protocols as described above for the synthesis of the azachalcone and the benzotriazole derivatives from benzaldehydes (Scheme 6). Amide 37a was thus obtained as a yellow solid in 48% yield and ketone 38a as a yellow-orange solid in 33% yield.

Scheme 6. Synthesis of (2E,4E)-5-(4-nitrophenyl)penta-2,4-dienoyl benzotriazolyl amide (37a) et (2E,4E)-5-(4-nitrophenyl)-1-(pyridin-3-yl)penta-2,4-dien-1-one (38a)

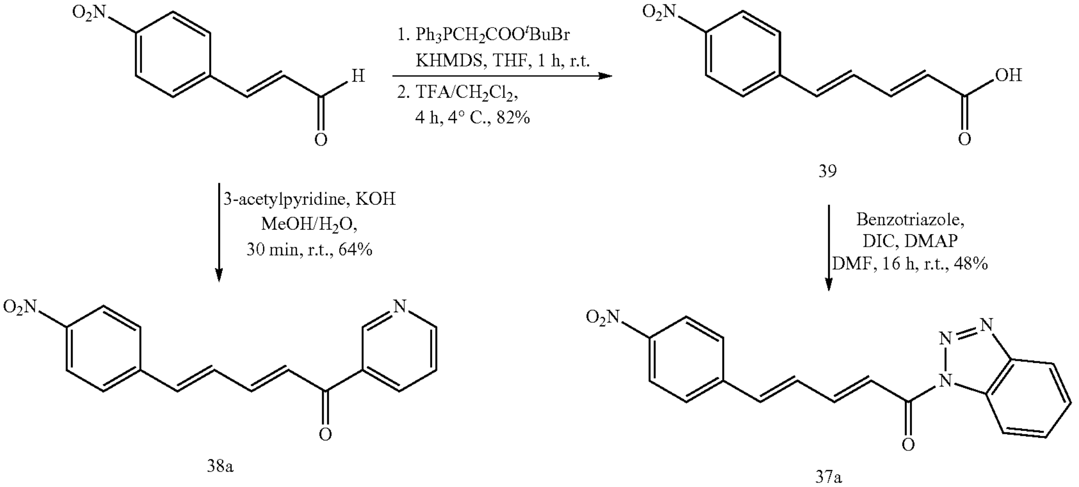

39

38a

37a

SYNTHESIS OF COMPOUNDS 4a-4o AND METHODOLOGY: All triazole derivatives (4a-o) were prepared using Huisgen [3+2] cycloaddition (Kolb, H. C. et al *Angew. Chem. Int. Ed.* 2001, 40, 2004) from 5-(4'-nitrophenyl)pent-4-(E)-en-1-yn-3-one as the ynone and a series of azides (Scheme 7). The ynone 3 was prepared following a published procedure (Miller, R. D.; Reiser, O., *J. Heterocyclic Chem.* 1993, 30, 755) to give a yellow solid in 27% isolated yield. Azides 2a-l were synthesized from the corresponding bromide derivatives 1a-l as described below (Alvarez, S. G.; Alvarez, M. T., *Synthesis* 1997, 413). The different yields obtained are illustrated in Table 5. The 4-methoxybenzylazide (2n) and the 4-azidomethyl-NH-triazole (2m), prepared following published procedures (Buckle, D. R.; Rockell, C. J. M., *J. Chem. Soc., Perkin Trans.* 1 1982, 627; Loren, J. C.; Sharpless, K. B., *Synthesis* 2005, 1514) completed the azides listing. Alkyl azides were typically made in yields of 66-99% by the nucleophilic substitution of alkyl bromide with 1.1 equivalents of sodium azide in dimethyl sulfoxide (DMSO). The low yield of azidocyclopentane 2c (66%) may be due its volatility.

Scheme 7. Synthesis of the inhibitors.

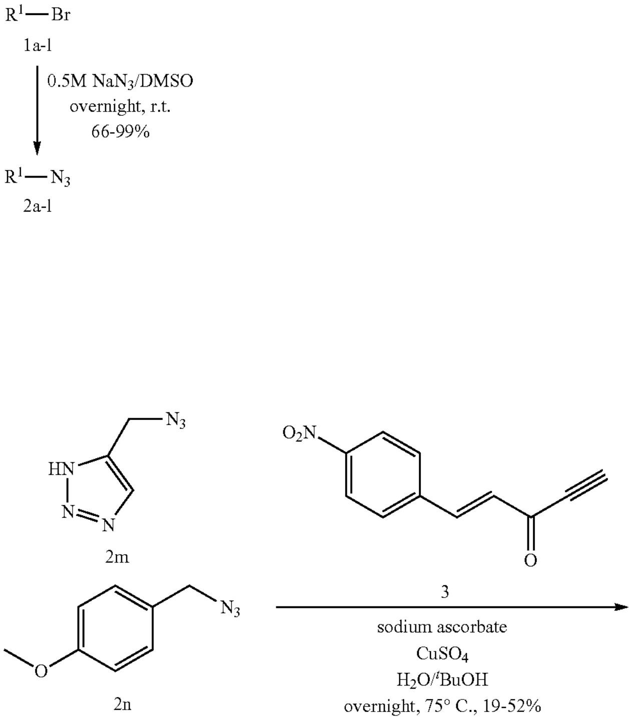

1a-l 2a-l

2m

2n

3

-continued
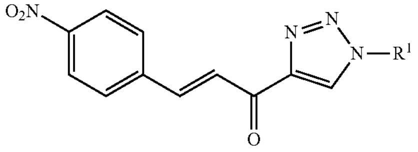
4a-n
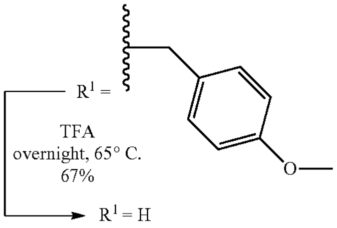
4n
4o
| | $R^1$ |
|---|---|
| a | 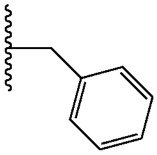 [SMILES: *Cc1ccccc1] |
| b | 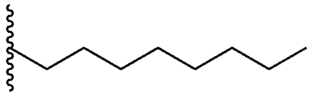 [SMILES: *CCCCCCCC] |
| c | 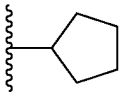 [SMILES: *C1CCCC1] |
| d | 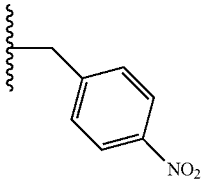 [SMILES: *Cc1ccc([N+](=O)[O-])cc1] |
| e | 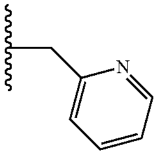 [SMILES: *Cc1ccccn1] |
| f | 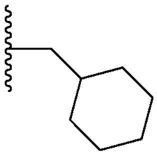 [SMILES: *CC1CCCCC1] |
| g | 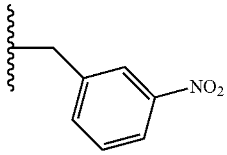 [SMILES: *Cc1cccc([N+](=O)[O-])c1] |

-continued

| | |
|---|---|
| h | 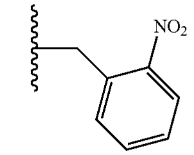 [SMILES: *Cc1ccccc1[N+](=O)[O-]] |
| i | 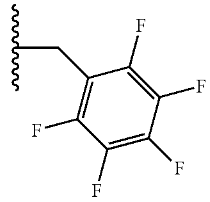 |
| j | 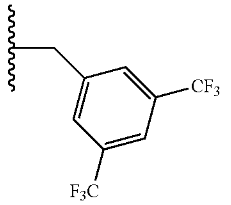 [SMILES: *Cc1cc(C(F)(F)F)cc(C(F)(F)F)c1] |
| k | 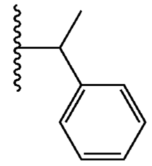 |
| l | 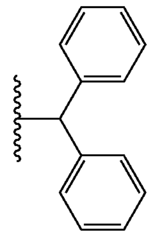 [SMILES: *C(c1ccccc1)c1ccccc1] |

Triazolyl derivatives 4a-n were prepared by a cycloaddition between the ynone 3 and the corresponding azide using a standard protocol in a $H_2O/^tBuOH$ 1:1 solution (v:v) employing sodium ascorbate and $CuSO_4$ overnight at 75° C. (Rostovtsev, V. V. et al *Angew. Chem. Int. Ed.* 2002, 41, 2596). After aqueous work-up and chromatography, product for biological examination was isolated in 19-52% isolated yield. The low cycloaddition isolated yields (19-52%) may likely be due to the reactivity of the ynone relative to the alkynes usually employed. Although triazole from alkynes have often been isolated by a simple filtration and washes, triazoles 4a-o from ynone 3 required a purification by chromatography.

ENZYME INHIBITION BY COMPOUNDS 14a-c, 14l, 15a, 15d-k, 15m-q, 30a, 30r, 30t, 37a and 38a: For enzymology studies of these compounds, recombinant guinea pig liver TGase was expressed in *Escherichia coli* and effectively purified (Gillet, S. M. F. G. et al J. N., Prot. Exp. & Purif. 2004, 33, 256). In addition to being easy to obtain in excellent yield and solubility, guinea pig liver TGase was chosen because it shows 80% homology with human tissue TGase (Aeschlimann, D.; Paulsson, M., *Throm. Haemost.* 1994, 71, 402) and may thus serve as a model for the evaluation of inhibitors of potential therapeutic utility.

The $IC_{50}$ values of synthetic analogues 14a-38a were determined from inhibition of the reaction of 54.4 mM of the chromogenic TGase substrate N-Cbz-Glu(γ-p-nitrophenyl ester)Gly with ~0.010 U of recombinant guinea pig liver TGase as previously reported (Leblanc, A.; Gravel, C.; Labelle, J.; Keillor, J. W. *Biochemistry* 2001, 40, 8335) and described in detail in the Materials section below. The mode of inhibition was determined for the representative lead compound 14a through non-linear regression of initial rate data to the Michaelis-Menten equation (FIG. 1). The apparent $K_m$ of the acyl-donor substrate increased with inhibitor concentration, while $V_{max}$ remained constant indicative that cinnamoyl amide 14a was a competitive inhibitor of the acyl-donor substrate used in the assay.

The structure-activity relationship study for TG2 inhibition by the cinnamoyl benzotriazolyl amides was initially focused on the effect of substituents on the cinnamoyl aromatic ring: p-$NO_2$, p-MeO, m-MeO, o-MeO, p-Me, m-Me, o-Me, p-Cl, o-Cl, p-BOCNH, m-BOCNH, p-FmocNH and p-$MeO_2C$ derivatives (15a, 15d, 15e, 15f, 15g, 15h, 15l, 15k, 15m, 15n, 15o, 15p and 15q) were synthesized and evaluated (Table 1). Among the analogues tested, the most potent TGase inhibitors ($IC_{50}$ values between 18 and 74 μM) possessed a substituent with a $sp^2$-hybridized oxygen: p-$NO_2$ (15a), p- and m-BOCNH (15n-15o), p-FmocNH (15p) and p-$MeO_2C$ (15q). Within this series, large substituents in the para position gave the best results. Analogues with other ring substituents (i.e. Me-, MeO- and Cl-) exhibited lower potency in the inhibition assay, which may in part be due to their limited solubility; moreover the position of these ring substituents did not influence inhibitor potency.

TABLE 1

Influence of the substituent on the cinnamoyl aromatic group

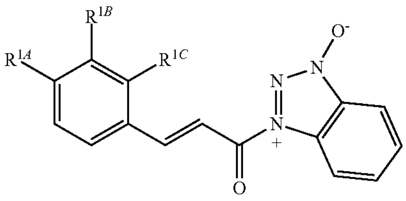

14a-c, 14l

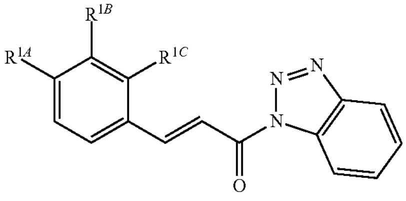

15a, 15d-k, 15m-q

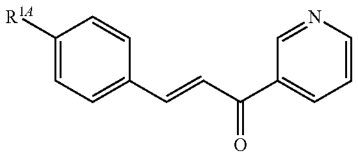

30a, 30r, 30t

| Compound | $R^{1A}$ | $R^{1B}$ | $R^{1C}$ | $IC_{50}$ (μM) |
|---|---|---|---|---|
| 14a | $NO_2$ | H | H | B (43 ± 2) |
| 14b | H | $NO_2$ | H | B (24 ± 5) |
| 14c | H | H | $NO_2$ | C (>100) |
| 14l | H | Cl | H | B (41 ± 9) |
| 15a | $NO_2$ | H | H | C (74 ± 15) |
| 15d | MeO | H | H | C (>100) |
| 15e | H | MeO | H | C (>100) |
| 15f | H | H | MeO | C (>100) |
| 15g | Me | H | H | C (>100) |
| 15h | H | Me | H | C (>100) |
| 15i | H | H | Me | C (>100) |
| 15j | H | H | H | C (>100) |
| 15k | Cl | H | H | C (>100) |
| 15m | H | H | Cl | C (>100) |
| 15n | BOCNH | H | H | A (18 ± 1) |
| 15o | H | BOCNH | H | B (39 ± 2) |
| 15p | FmocNH | H | H | B (25 ± 5) |
| 15q | MeOOC | H | H | B (27 ± 4) |
| 30a | $NO_2$ | H | H | B (21 ± 4) |
| 30r | $NH_2$ | H | H | C (148 ± 27) |
| 30t | AcNH | H | H | B (28 ± 4) |

Legend: $IC_{50}$ A = <20 μM; B = >20 μM < 50 μM; and C >50 μM.

A particularly potent group of inhibitors were the cinnamoyl oxybenzotriazolyl amides (14a-14c, 14l). Comparison of the inhibitory activity of the p-, m- and o-$NO_2$ cinnamoyl oxybenzotriazolyl amides 14a, 14b and 14c (Table 1) demonstrated that substitution at the ortho position resulted in decreased activity. In marked difference to the chlorinated benzotriazolyl derivatives 15k and 15m, m-chloro cinnamoyl oxybenzotriazolyl amide 14l exhibited an $IC_{50}$ value of 41 μM despite not having a $sp^2$-hybridized oxygen. (Table 1).

Figure 3:
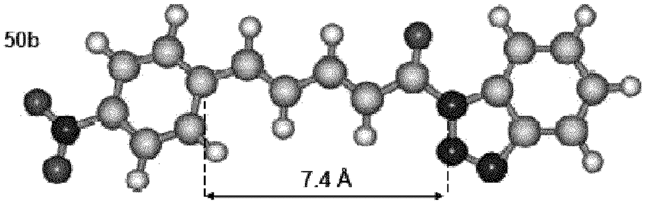
FIG. 3 is an illustration of three-dimensional rendering of inhibitors 13b and 50b.
Figure 3:
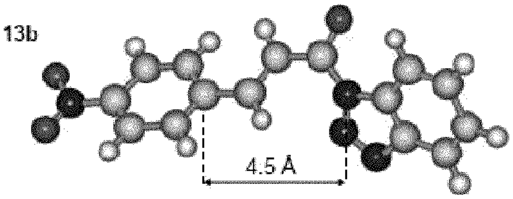

The importance of the cinnamate double bond for activity (Table 2) was demonstrated by the significant loss of activity of analogues 32a and 33a, wherein the phenylvinyl group of 15a is reduced to a phenylethyl group or replaced by a benzyloxy group, respectively. On complete removal of the double bond, p-nitrobenzoyl benzotriazolyl amide 34a was found to react in a time-dependent fashion as an irreversible inhibitor, likely due to acylation of a nucleophilic amino acid moiety with loss of the benzotriazole leaving group. Taken together, these results suggested that the extended conjugation and conformational rigidity of the amide were important for reversible inhibitory activity. Finally, the importance of the distance between the two aromatic moieties of these inhibitors was evaluated. Namely, benzotriazole derivative 37a and azachalcone 38a were synthesized and tested as inhibitors bearing an additional double bond. Neither of these two extended conjugated compounds showed significant inhibition (Table 2). Apparently, the 7.4 Å distance between the phenyl group and the benzotriazole nitrogen of compound 37a (determined by semi-empirical (AM1) minimization) is detrimental to affinity for TG2, compared to the 4.5 Å distance in the corresponding 15a (FIG. 3).

TABLE 2

Influence of the cinnamoyl double bond

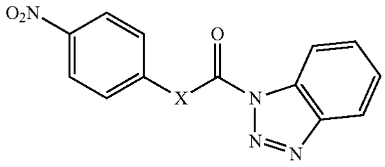

| Compd | X | $IC_{50}$ (μM) |
|---|---|---|
| 15a | CH═CH | C (74 ± 15) |
| 32a | $CH_2$—O | C (>200) |
| 33a | $CH_2$—$CH_2$ | C (>200) |
| 34a | — | irreversible |
| 37a | CH═CH—CH═CH | C (>200) |

Legend: $IC_{50}$ A = <20 μM; B = >20 μM < 50 μM; and C >50 μM.

Considering that the benzotriazolyl amides were potentially labile to nucleophilic attack and solvolysis, a series of more stable cinnamoyl amides and esters were evaluated (Table 2). Esters 19a and 20a showed little inhibitory activity, demonstrating at least that the amide moiety of this class of inhibitors is important for affinity. Secondary amides 21a-23a also showed markedly less activity than the tertiary benzotriazole amides, suggesting initially that tertiary amides may show greater affinity than secondary amides. The lack of activity of piperidine and pyrrolidine amides 24a and 25a indicated, however, that recognition required more than just a tertiary amide group. Amides 24a and 25a differed from the benzotriazole series by their lack of an aromatic ring and additional nitrogen atoms in the ring. Inhibitory activity was observed when the benzotriazole was replaced by other heterocycles containing multiple hydrogen bond acceptors such as in benzotriazolides 14a, 15a, 16a and imidazolide 18a. In addition tertiary dibenzyl amide 26a exhibited an $IC_{50}$ value of 57 μM indicating that other factors may contribute to enzyme affinity.

Considering that the triazole nitrogens may serve as hydrogen bond acceptors in the enzyme bound structure, a second subclass of cinnamoyl derivatives was designed, in which this moiety was replaced by a 3-pyridine group. Azachalcones 30a, 30r and 30t proved to be as effective as the benzotriazolyl amide inhibitors (Table 1) and relatively more soluble in the 5% DMF/$H_2O$ solvent mixture used for the enzymatic assay. Furthermore, the presence of the nitrogen in the azachalcones was demonstrated to be important for TG2 inhibition, by the lack of activity of the parent chalcone, (E)-3-(4-nitrophenyl)-1-phenylprop-2-en-1-one. In this series the importance of the p-nitro group on the cinnamyl ring was also investigated. Reduction to the (E)-3-(4-aminophenyl)-1-phenylprop-2-en-1-one 30r resulted in a 5-fold loss of potency, which was recovered by acylation of the pendant amino group in acetamide 30t (Table 1). This observation reinforces the notion that an $sp^2$ hybridized oxygen extending from the para position may pick up favourable interactions with the enzyme, increasing binding affinity.

To further test the hypothesis that the triazole nitrogens increased affinity by serving as hydrogen bond acceptors, coumarin derivative 28a was synthesized and evaluated. Coumarin 28a, which contains two oxygens capable of serving as hydrogen bond acceptors, exhibited an $IC_{50}$ value of 48 μM (Table 3). Considering that a potential hydrogen bond acceptor (N or O) was important for the affinity of the acylated moiety, the influence of aromaticity was probed. Amide 29a, possessing a 1,3-oxazinan-3-yl moiety, was synthesized and exhibited little inhibitory potency, suggesting that aromaticity (or at least planarity) of the acylated ring was critical.

TABLE 3

Influence of the acylated moiety

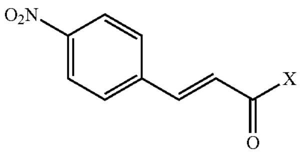

| Compd | X | $IC_{50}$ (μM) |
|---|---|---|
| 15a | 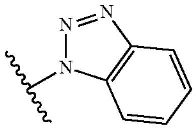 [SMILES: *n1nnc2ccccc21] | C |
| 14a | 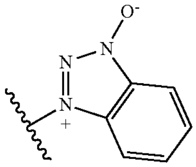 | B |
| 16a | 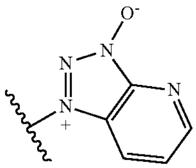 | B |
| 18a | 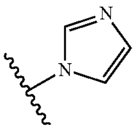 [SMILES: *n1ccnc1] | B |

TABLE 3-continued

Influence of the acylated moiety

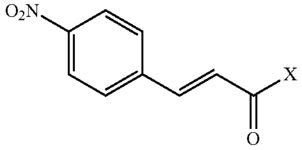

| Compd | X | $IC_{50}$ (μM) |
|---|---|---|
| 19a | 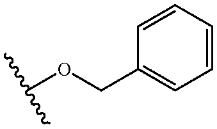 [SMILES: *OCc1ccccc1] | C |
| 20a | 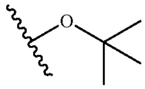 [SMILES: *OC(C)(C)C] | C |
| 21a | 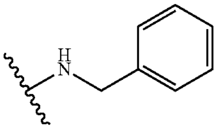 [SMILES: *NCc1ccccc1] | C |
| 22a | 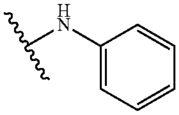 [SMILES: *Nc1ccccc1] | C (>200) |
| 23a | 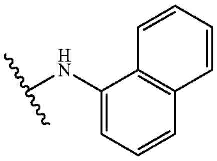 [SMILES: *Nc1cccc2ccccc12] | C (>200) |
| 24a | 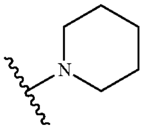 [SMILES: *N1CCCCC1] | C (>200) |
| 25a | 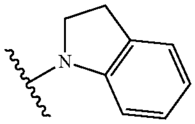 [SMILES: *N1CCc2ccccc21] | C (>200) |
| 26a | 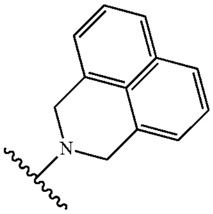 | B (57 ± 7) |
| 27a | 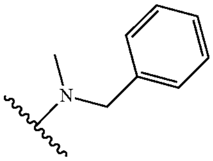 [SMILES: *N(C)Cc1ccccc1] | C (>200) |

TABLE 3-continued

Influence of the acylated moiety

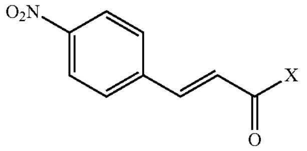

| Compd | X | $IC_{50}$ (μM) |
|---|---|---|
| 28a | 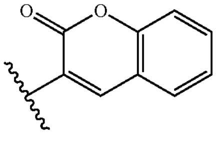 [SMILES: *c1cc2ccccc2oc1=O] | B (48 ± 6) |
| 29a | 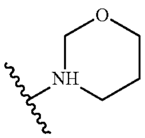 [SMILES: *N1CCCOC1] | C (>200) |

Legend: $IC_{50}$ A = <20 μM; B = >20 μM < 50 μM; and C >50 μM.

Figure 4:
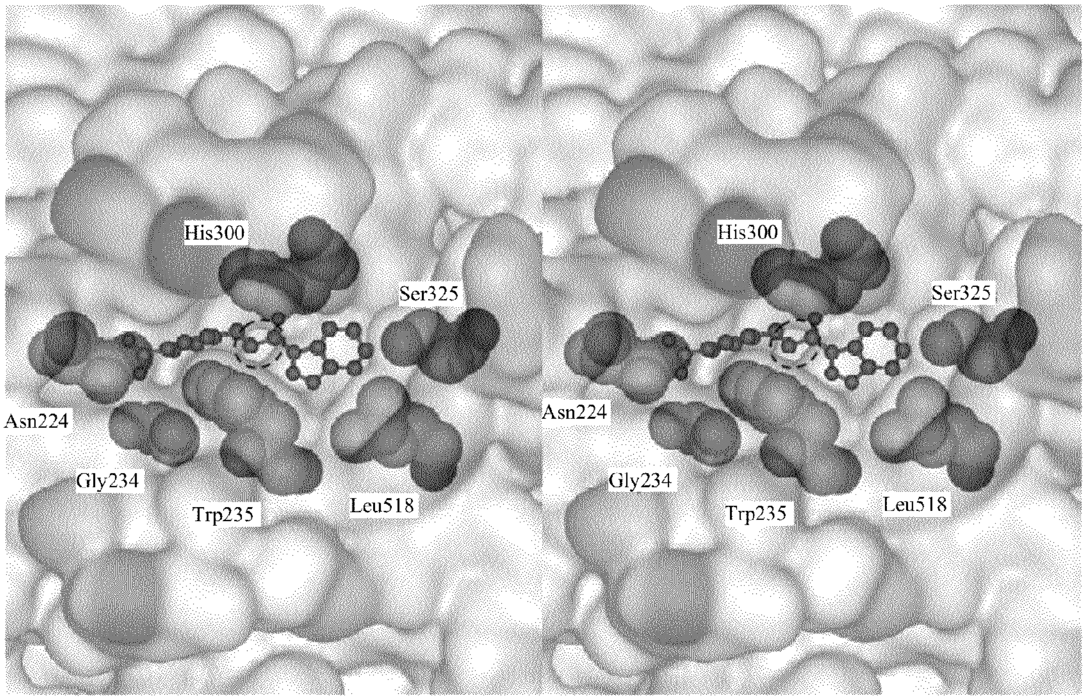
FIG. 4 is an illustration of a hypothetical inhibitor binding model.

Very few X-ray structures of TG2 have been published (Bishop, P. D. et al *J. Biol. Chem.* 1990, 265 (23), 13888; Yee, V. C. et al *Proc. Natl. Acad. Sci. USA* 1994, 91, 7296; Hilgenfeld, R. et al *FEBS* 1990, 265, 110; Weiss, M. S. et al. *Acta Cryst. Section D* 1999, D55, 1858; Fox, B. A. et al *J. Biol. Chem.* 1999, 274 (8), 4917; Kim, H.-C. et al *J. Struct. Biol.* 2001, 135, 73; Nogushi, K. et al *J. Biol. Chem.* 2001, 276, 12055) and none has featured a bound ligand. Interpretation of structure-function information has thus been facilitated by computational analysis. For example, the high structural homology between guinea pig liver TGase and red sea bream TGase, for which crystallographic data exist, has aided modelling studies to predict the binding of substrate-derived analogs. In light of their ability to compete with substrate, the cinnamoyl inhibitors may simply be considered to interact with the acyl-donor substrate binding site. Using the coordinates of the structure of the highly homologous red sea bream TG2, cinnamoyl inhibitor 15a was docked into the putative acyl-donor binding site (Chica, R. A. et al *Protein Science* 2004, 13, 979) using MGL Tools 2.3. This simulation demonstrated that binding in the hydrophobic groove of TG2 was possible such that the entrance to the active site was blocked (FIG. 4). The residues shown in FIG. 4 are all strictly conserved in the guinea pig liver TG2 used in this study and in human TG2. The exception is Leu518, which is replaced by a homologous Val residue in the guinea pig liver enzyme and an isomeric Ile residue in the human enzyme. These residues were highlighted since they form close contacts to the inhibitor in our hypothetical binding model that are consistent with the observed structure-function relationships revealed by our inhibition studies. For example, the $sp^2$ hybridized oxygen of the nitro group in the para position of the cinnamoyl ring of 15a is within a couple angstroms of Asn224 and the Gly224 backbone as potential hydrogen bond donors. The phenyl ring of the cinnamoyl group appears to form an orthogonal π-dipole interaction with indole NH of Trp236. This residue also appears to impose a steric restriction with His300. The planar double bond of the cinnamyl residue can be inserted into this narrow cleft, but the flexibility and volume of the corresponding linkers of 32a and 33a may prevent their insertion. The indole ring of Trp236 may also be able to form a π-dipole interaction with the triazole nitrogens of 15a—an interaction inaccessible to the poorest inhibitors of Table 4. Finally, the phenyl ring of the benzotriazole group is seated in the hydrophobic binding groove and partly surrounded by Leu518 (or the corresponding Val residue in the guinea pig liver enzyme) and Ser325. The restricted and hydrophobic nature of this pocket may explain why voluminous non-planar rings do not appear to be accommodated at this position (e.g. 29a) and why longer rigid compounds (e.g. 37a and 38a) would incur unfavourable steric hindrance.

TABLE 4

Alkyl azides prepared from alkyl bromides and 1.1 equiv. of $NaN_3$ in DMSO at room temperature.

| | Alkyl Bromide 1 | Product 2 | Isolated Yield (%) |
|---|---|---|---|
| a | 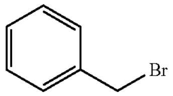 | 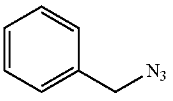 | 97 |
| b | 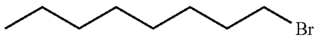 | 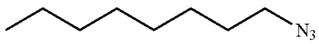 | 82 |
| c | 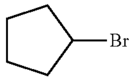 | 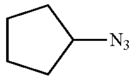 | 66 |
| d | 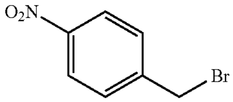 | 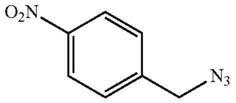 [SMILES: [N-]=[N+]=NCc1ccc([N+](=O)[O-])cc1] | 99 |
| e | 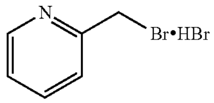 | 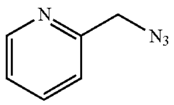 | 95 |

TABLE 4-continued

Alkyl azides prepared from alkyl bromides and 1.1 equiv. of $NaN_3$ in DMSO at room temperature.

| | Alkyl Bromide 1 | Product 2 | Isolated Yield (%) |
|---|---|---|---|
| f | 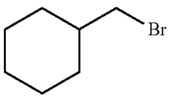 | 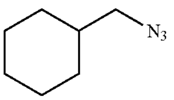 | 98 |
| g | 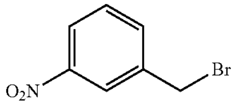 | 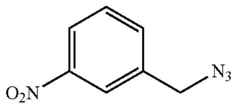 | 88 |
| h | 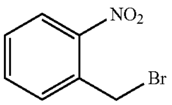 [SMILES: O=[N+]([O-])c1ccccc1CBr] | 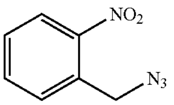 [SMILES: [N-]=[N+]=NCc1ccccc1[N+](=O)[O-]] | 88 |
| i | 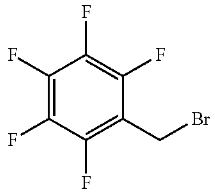 | 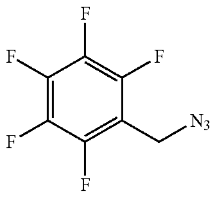 [SMILES: [N-]=[N+]=NCc1c(F)c(F)c(F)c(F)c1F] | 89 |
| j | 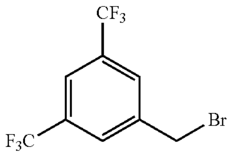 [SMILES: FC(F)(F)c1cc(CBr)cc(C(F)(F)F)c1] | 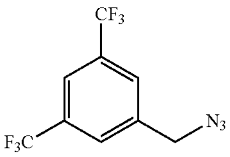 [SMILES: [N-]=[N+]=NCc1cc(C(F)(F)F)cc(C(F)(F)F)c1] | 80 |
| k | 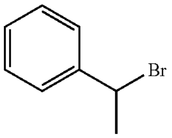 | 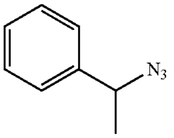 | 99 |
| l | 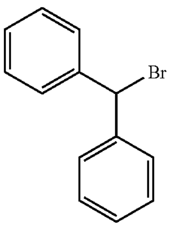 | 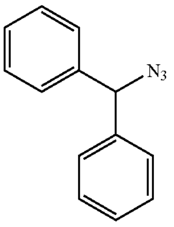 [SMILES: [N-]=[N+]=NC(c1ccccc1)c1ccccc1] | 99 |

To examine the enzyme selectivity of this new family of TG2 inhibitors, several representative compounds (14a, 15p, 18a, 28a and 30a) were further tested as inhibitors of related enzymes. For these studies, Factor XIIIa was chosen because it is a member of the family of transglutaminase enzymes and its inhibition in vivo may lead to compromised coagulation and toxicity. Caspase 3 was also chosen because as a cysteine protease, its acyl transfer mechanism is phenomenologically similar to that of TGase. At concentrations approaching the limits of their solubility, most of those compounds had no discernable effect on the activities of either of these enzymes (data not shown). Only the coumarin derivative 28a was found to display slight inhibitory activity toward caspase 3—namely, 28% inhibition at 6 μM of 48c. This selectivity bodes well for in vivo application.

ENZYME INHIBITION BY COMPOUNDS 4a-4o: The yields obtained for compounds 4a-4o are indicated in Table 5. For the ensuing enzymatic tests, recombinant guinea pig liver TGase was expressed in *E. Coli* and effectively purified. Kinetic evaluation of the compounds 4a-4o inhibitors was carried out using direct continuous colorimetric assays (Leblanc, A. et al *Biochemistry* 2001, 40, 8335).

TABLE 5
Huisgen [3 + 2] cycloaddition between 5-(4'-nitrophenyl)pent-4-(E)-en-1-yn-3-one and alkyl azides.
| | Alkyl azide 2 | Triazolyl derivative 4 | Isolated Yield (%) |
|---|---|---|---|
| a | 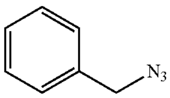 | 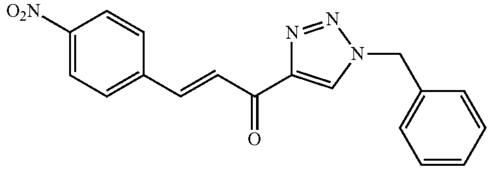 [SMILES: O=C(/C=C/c1ccc([N+](=O)[O-])cc1)c1cn(Cc2ccccc2)nn1] | 23 |
| m | 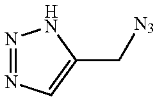 | 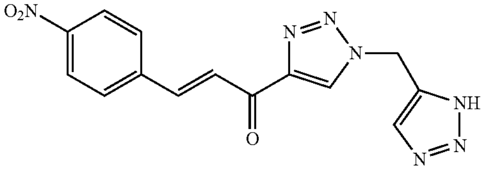 [SMILES: O=C(/C=C/c1ccc([N+](=O)[O-])cc1)c1cn(Cc2cnn[nH]2)nn1] | 23 |
| b | 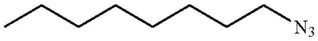 | 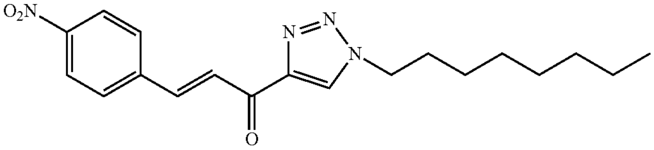 [SMILES: CCCCCCCCn1cc(C(=O)/C=C/c2ccc([N+](=O)[O-])cc2)nn1] | 20 |
| c | 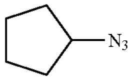 | 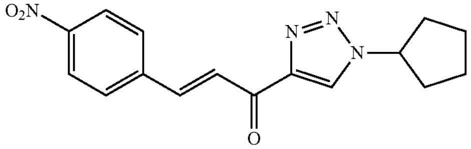 [SMILES: O=C(/C=C/c1ccc([N+](=O)[O-])cc1)c1cn(C2CCCC2)nn1] | 38 |
| d | 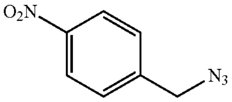 [SMILES: [N-]=[N+]=NCc1ccc([N+](=O)[O-])cc1] | 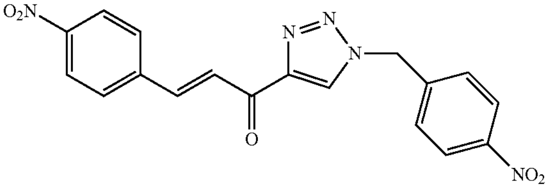 [SMILES: O=C(/C=C/c1ccc([N+](=O)[O-])cc1)c1cn(Cc2ccc([N+](=O)[O-])cc2)nn1] | 19 |
| n | 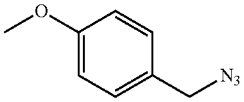 | 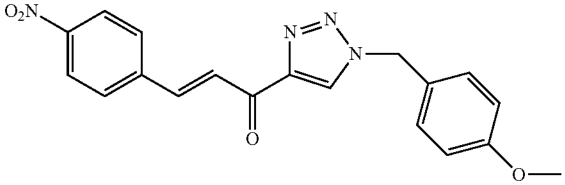 [SMILES: COc1ccc(Cn2cc(C(=O)/C=C/c3ccc([N+](=O)[O-])cc3)nn2)cc1] | 23 |
| e | 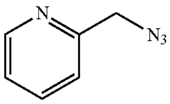 | 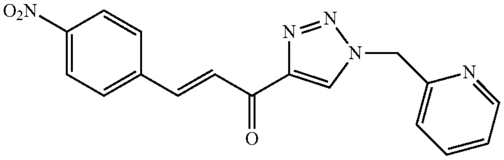 [SMILES: O=C(/C=C/c1ccc([N+](=O)[O-])cc1)c1cn(Cc2ccccn2)nn1] | 30 |
| f | 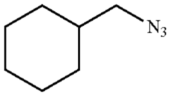 | 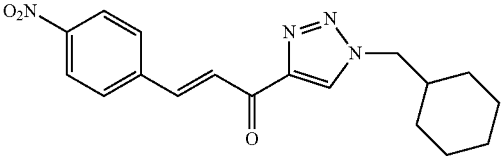 [SMILES: O=C(/C=C/c1ccc([N+](=O)[O-])cc1)c1cn(CC2CCCCC2)nn1] | 32 |

TABLE 5-continued

Huisgen [3 + 2] cycloaddition between 5-(4'-nitrophenyl)pent-4-(E)-en-1-yn-3-one and alkyl azides.

Figure 5:
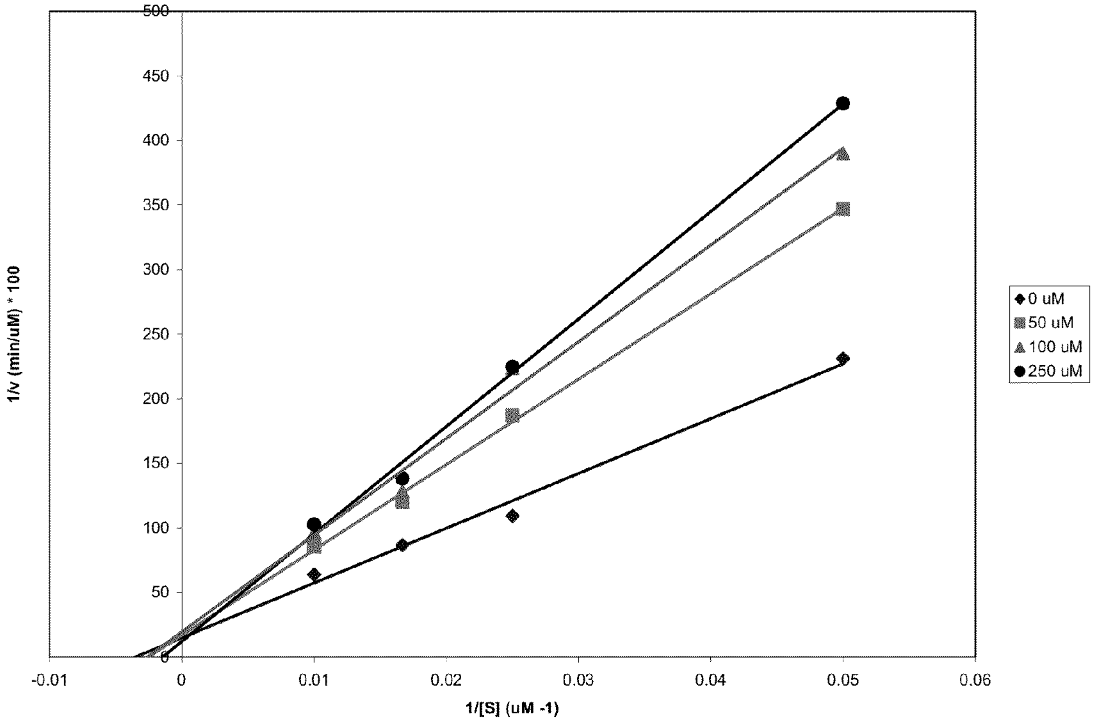
FIG. 5 is an illustration of a Lineweaver-Burk plot showing competitive inhibition by inhibitor 4d.

| | Alkyl azide 2 | Triazolyl derivative 4 | Isolated Yield (%) |
|---|---|---|---|
| g | 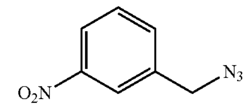 [SMILES: [N-]=[N+]=NCc1cccc([N+](=O)[O-])c1] | 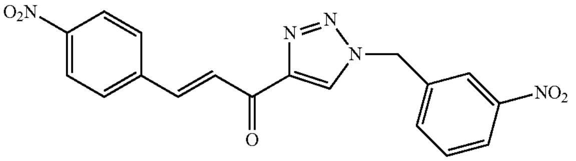 [SMILES: O=C(/C=C/c1ccc([N+](=O)[O-])cc1)c1cn(Cc2cccc([N+](=O)[O-])c2)nn1] | 19 |
| h | 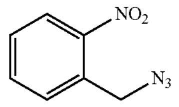 [SMILES: [N-]=[N+]=NCc1ccccc1[N+](=O)[O-]] | 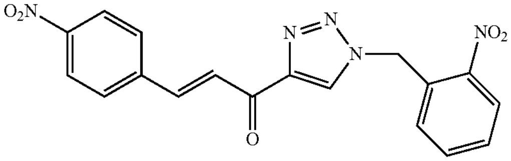 [SMILES: O=C(/C=C/c1ccc([N+](=O)[O-])cc1)c1cn(Cc2ccccc2[N+](=O)[O-])nn1] | 24 |
| i | 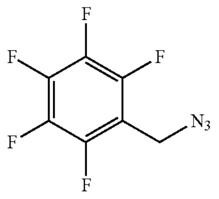 [SMILES: [N-]=[N+]=NCc1c(F)c(F)c(F)c(F)c1F] | 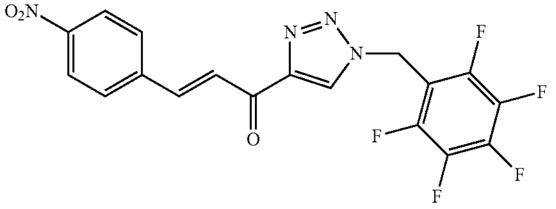 [SMILES: O=C(/C=C/c1ccc([N+](=O)[O-])cc1)c1cn(Cc2c(F)c(F)c(F)c(F)c2F)nn1] | 33 |
| j | 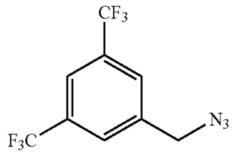 | 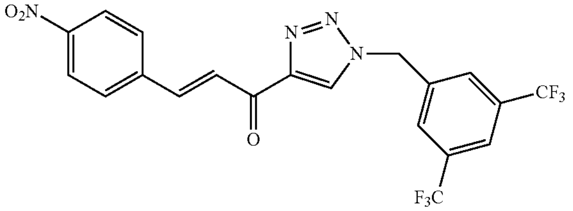 [SMILES: O=C(/C=C/c1ccc([N+](=O)[O-])cc1)c1cn(Cc2cc(C(F)(F)F)cc(C(F)(F)F)c2)nn1] | 52 |
| k | 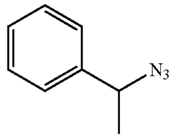 | 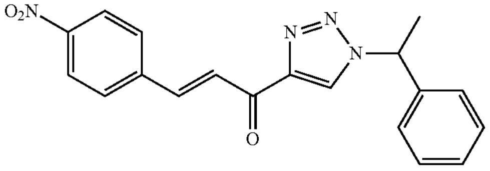 [SMILES: CC(c1ccccc1)n1cc(C(=O)/C=C/c2ccc([N+](=O)[O-])cc2)nn1] | 48 |
| l | 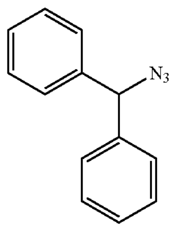 [SMILES: [N-]=[N+]=NC(c1ccccc1)c1ccccc1] | 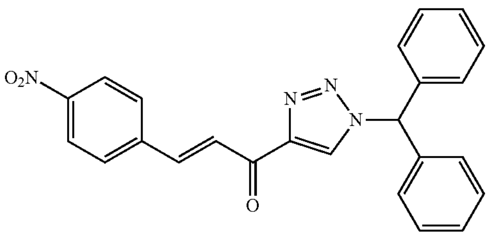 [SMILES: O=C(/C=C/c1ccc([N+](=O)[O-])cc1)c1cn(C(c2ccccc2)c2ccccc2)nn1] | 39 |

p-Nitrocinnamoyltriazoles 4a-b, 4d-h, 4k and 4m-o exhibited activity as reversible and competitive TGase inhibitors with $IC_{50}$ values varying between 2.1 μM and 45 μM typically in the range of 10 μM (Table 6). Their mode of inhibition was confirmed to be competitive through detailed evaluation of representative triazole 4d. Upon variation of the concentration of substrate at different concentrations of inhibitor, the resulting Lineweaver-Burk plot (FIG. 5) showed intersecting lines that cross on the y-axis, indicative of competitive inhibition.

TABLE 6

$IC_{50}$ of the Huisgen [3 + 2]cycloaddition products.

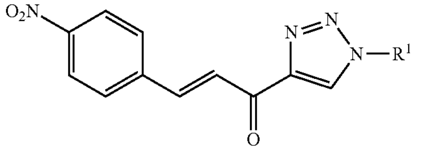

| Enone | $R^1$ | $IC_{50}$ (μM) |
| --- | --- | --- |
| 4a | 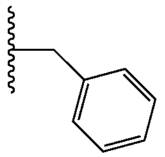 [SMILES: *Cc1ccccc1] | A (4.3 ± 0.3) |
| 4m | 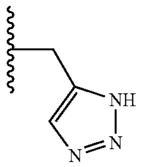 [SMILES: *Cc1cnn[nH]1] | B (33.0 ± 5.4) |
| 4b | 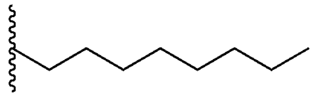 [SMILES: *CCCCCCCC] | B (28.5 ± 2.4) |
| 4c | 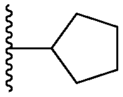 [SMILES: *C1CCCC1] | C (>100) |
| 4d | 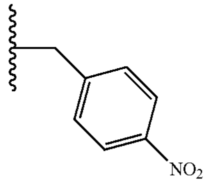 [SMILES: *Cc1ccc([N+](=O)[O-])cc1] | A (2.1 ± 0.3) |
| 4n | 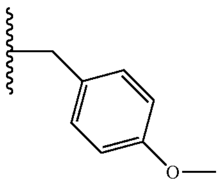 [SMILES: *Cc1ccc(OC)cc1] | A (14.0 ± 2.1) |
| 4o | H | B (45.0 ± 0.5) |
| 4e | 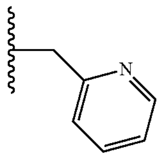 [SMILES: *Cc1ccccn1] | A (18.0 ± 1.7) |
| 4f | 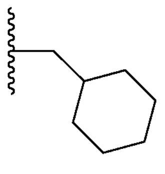 [SMILES: *CC1CCCCC1] | A (11.0 ± 1.5) |

TABLE 6-continued $IC_{50}$ of the Huisgen [3 + 2]cycloaddition products.

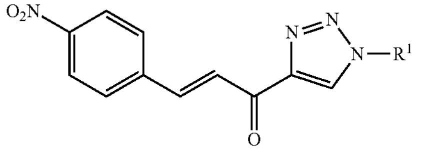

| Enone | $R^1$ | $IC_{50}$ (μM) |
| --- | --- | --- |
| 4g | 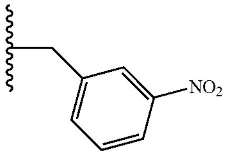 [SMILES: *Cc1cccc([N+](=O)[O-])c1] | A (9.4 ± 2.6) |
| 4h | 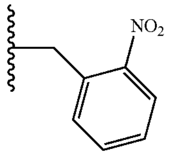 [SMILES: *Cc1ccccc1[N+](=O)[O-]] | A (10.7 ± 1.1) |
| 4i | 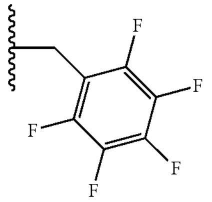 [SMILES: *Cc1c(F)c(F)c(F)c(F)c1F] | C (>100) |
| 4j | 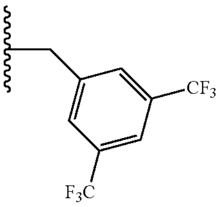 [SMILES: *Cc1cc(C(F)(F)F)cc(C(F)(F)F)c1] | C (>100) |
| 4k | 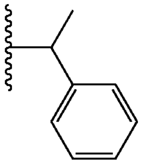 [SMILES: *C(C)c1ccccc1] | A (17.0 ± 1.5) |
| 4l | 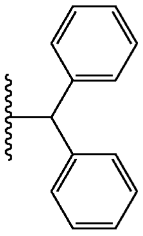 [SMILES: *C(c1ccccc1)c1ccccc1] | C (>100) |

Legend: $IC_{50}$ A = <20 μM; B = >20 μM < 50μM; and C >50 μM.

The triazole N-alkyl group was shown to be important for inhibition activity by the relatively high $IC_{50}$ value (45.0 μM) of the parent 4-cinnamoyltriazole 4o without nitrogen substituent. Similarly, 1-triazolemethyl 4-cinnamoyltriazole 4m possessing the least hydrophobic N-alkyl group in the series, exhibited a relatively higher $IC_{50}$ value. The presence of a 1-alkyl substituent increases the hydrophobicity of the 4-cinnamoyltriazole analog and may thereby improve affinity for the hydrophobic cleft leading to the TGase active site (Chica, R. A.; Gagnon, P.; Keillor, J. W.; Pelletier, J. N., *Protein Science* 2004, 13, 979). 1-Cyclopentyl and 1-diphenylmethyl 4-cinnamoyltriazoles 4c and 4l also exhibited relatively poor activity likely due to unfavourable steric interactions of the 1-position substituent.

1-Benzyl 4-p-nitrocinnamoyltriazoles exhibited potent inhibitor activity as demonstrated by the 4.3 μM $IC_{50}$ value for the parent 4a that was only slightly bettered by 1-p-nitrobenzyl 4-p-nitrocinnamoyltriazole 4d (2.1 μM). Removal of the aromatic system in cyclohexylmethyl analog 4f resulted in a 2.5 fold loss in potency relative to the 1-benzyl analog 4a. Similarly, alkyl branching at the benzylic position with α-methylbenzyl analog 4k caused a 4-fold reduction in potency versus 4a. Replacement of the 4-nitro substituent as well as moving the nitro group to the in meta (4g) or ortho (4h) positions, caused 4-7 fold reductions in potency versus the p-nitrobenzyl analog 4d. Although the influence of the p-nitro group on the benzyl substituent may be inductive, the loss of activity of pentafluorobenzyl analog 4i and the lower potency of 2-pyridylmethyl analog 4e suggest that the nitro group may directly interact with the receptor.

For compounds 4o-4m, the enones obtained showing an activity were reversible and competitive inhibitors of TGase. Their $IC_{50}$ varied between 2.1 μM and 45 μM but most of the enones were in the range of 10 μM. An N-alkyl group on the triazole moiety seemed important for inhibition activity. Enone 4o with a hydrogen on the triazole ring had a relatively high $IC_{50}$. The presence of an alkyl group on the triazole moiety can increase the hydrophobic character of the molecules and may thereby improve affinity for the hydrophobic cleft leading to the active site. Enone 4m with the relatively hydrophillic N-triazolyl methyl group also had a high $IC_{50}$. Enones 4c and 4l may indicate the importance of steric effects for limiting inhibition. A benzyl group for the N-alkyl group on the triazole ring gave the most potent inhibitors (4a, 4d, 4n, 4g and 4h). Enones 4a, 4d and 4n may exhibit a i-stacking interaction with residues in TGase. Enone 4d is the most efficient inhibitors in the series and moving the position of the nitro group to meta or ortho reduce efficacy, indicating that the nito group may interact with the receptor. Finally, activity was lost when more than one substituent was placed on the N-benzyl group on the triazole moiety in examples 4i and 4j.

The efficiency to obtain reversible and competitive inhibitors of TGase using Huisgen [2+3] cycloaddition between an ynone and an azide has opened the door to combinatorial chemistry for furnishing compound libraries for biological screening. 4-p-Nitrocinnamoyltriazoles have been demonstrated to be a new potent reversible and competitive class of TGase inhibitors. In particular, 1-benzyl and 1-p-nitrobenzyl 4-p-nitrocinnamoyltriazoles 4a and 4d have exhibited 4.3 μM and 2.1 μM $IC_{50}$ values respectively. Considering their potency and the ease of analog generation by the [3+2]-cycloaddition of various ynones and azides, the cinnamoyltriazole motif represents a promising scaffold for building novel inhibitors for exploring the pharmacology of tissue transglutaminase.

Figure 6:
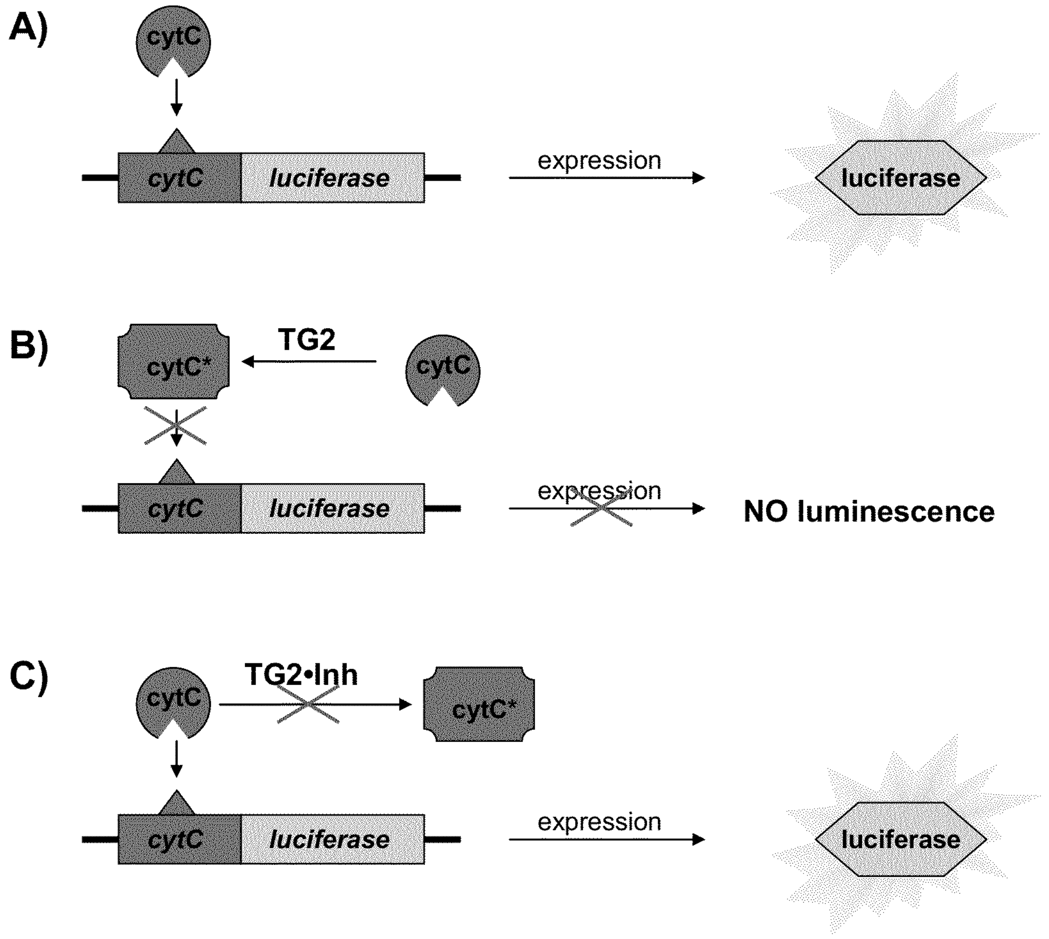

IN VITRO STUDIES FOR COMPOUND 15a: A cytochrome c (cytC) promoter/luciferase reporter assay (illustrated in FIG. 6) was used to assess tissue transglutaminase (TG2) activity for compound 15a. In the absence of TG2, transcription factors bind to the cytC promoter region of the luciferase gene, and the level of expressed luciferase is detected from the luminescence of the Chinese Hamster Ovary (CHO) cell lysate (A). The level of effective cytC promoter is sensitive to endogenous TG2 co-expressed in CHO cells. High TG2 expression results in low promoter activity, presumably because the transcription factors that bind to the cytC promoter have Gln-rich sequences that are modified by TG2-mediated hydrolysis or transamidation (B). In the presence of TG2 inhibitors, TG2-induced silencing of the promoter is repressed and luciferase is detected in the lysate once more (C). In this assay, CHO cells are incubated in the presence of the inhibitor compound for 12 hours, after which the luminescence of cell lysate is measured, as an indication of the level of TG2 inhibition. It was found that incubation in the presence of 100 μM of compound 15a resulted in complete inhibition of TG2-mediated silencing. Therefore, this shows permeability of the compounds of the present invention to a mammalian cell.

Materials

The different benzaldehydes, the different cinnamic acids, 1-hydroxy-1-azabenzotriazole, 1-hydroxybenzotriazole, benzotriazole, KHMDS, (tert-butoxycarbonylmethyl)triphenylphosphonium bromide, benzotriazole, HOBt, DIC, DMAP, di-tert-butyl dicarbonate, 9-fluorenylmethoxycarbonyl chloride, p-nitrophenylchloroformate, p-nitrobenzylchloroformate, aniline, benzylamine, dibenzylamine, benzyl alcohol, indoline, piperidine, N-methylbenzylamine, imidazole, 3-acetylpyridine, p-nitrocinnamaldehyde, potassium carbonate formaldehyde, 3-aminopropanol and 3-(bromoacetyl)coumarin were all obtained from Sigma-Aldrich. Buffer salts, Colorimetric Caspase 3 assay kit, N-α-acetyl-L-lysine methyl ester hydrochloride, α-ketoglutaric acid sodium salt, β-nicotinamide adenine dinucleotide, reduced form (β-NADH) and bovine liver glutamic dehydrogenase (GDH) were from Sigma Chemical Co. Factor XIIIa was purchased from Haemotologic Technologies Inc. One unit of Factor XIIIa is equal to its activity in 1 mL of normal plasma. Triethylamine and DMF were obtained from ACP. Potassium hydroxide was obtained from BDH. Bulk solvents were obtained from EMD. The substrate N-Cbz-Glu(γ-p-nitrophenyl ester)Gly was synthesized in our laboratory according to a published procedure (Bromides, $NaN_3$, $CuSO_4$ and L-ascorbic acid sodium salt were obtained from Aldrich. DMF and tert-butanol ($^t$BuOH) were obtained from ACP. DMSO, $Et_2O$, EtOAc and hexanes were obtained from EMD. N-Cbz-Glu(γ-p-nitrophenyl ester)Gly (Keillor, J. W. *Chem. Biol.* 2005, 12(4), 410) was synthesized in the inventors' laboratory according to published procedure.

$^1$H and $^{13}$C NMR spectra were recorded on a Bruker spectrometer respectively at 300 and 75 MHz in the indicated solvent. Chemical shifts are reported in ppm with internal reference to TMS. High-resolution mass spectra (HRMS) were recorded on a LC-MSD-T of instrument from Agilent technologies in positive electrospray mode in general. Either protoned molecular ions $(M+H)^+$ or sodium adducts $(M+Na)^+$ were used for empirical formula confirmation.

Kinetic Methods

Kinetic runs were recorded on a Cary 100 BIO UV-Visible spectrophotometer at 405 nm and 25° C., in a buffer composed of 50 mM $CaCl_2$, 50 μM EDTA and 0.1 M MOPS (pH 7.0). All aqueous solutions were prepared using de-ionized water purified from the Millipore BioCell system. All kinetic assays were carried out using 900 μL of buffer, 50 μL of 0.15 mg/mL TGase and 25 μL of a 2.2 mM stock solution of substrate N-Cbz-Glu(γ-p-nitrophenyl ester)Gly, in the presence of 0-25 μL (contingent on solubility) of an anhydrous DMF stock solution of the inhibitor. Final inhibitor concentrations ranged thus from 1.8 μM to the solubility limit of each compound. Factor XIIIa activity was measured using a coupled-enzyme assay (Day, N.; Keillor, J. W. *Anal. Biochem.* 1999, 274, 141). Factor XIIIa, was added to a final concentration of 0.89 μg/mL to a pH 8.5 solution (0.1 M Tris-HCl, 5 mM $CaCl_2$ and 10 mM DDT) of 0.5 mM β-NADH, 3.3 mM Na-acetyl-L-lysine methyl ester, 10 mM α-ketoglutaric acid sodium salt and 297 μg/mL glutamate dehydrogenase (GDH).

The subsequent absorbance decrease was followed at 340 nm at 37° C. Caspase 3 activity was measured by monitoring the release of p-nitroaniline (pNA) ($\lambda_{abs}$=405 nm) from the peptidic substrate Ac-Asp-Glu-Val-Asp-pNA (20 μM) catalyzed by human caspase 3 (Sigma, 250 ng/mL) at pH 7.4 (18.6 mM HEPES, 1.9 mM EDTA, 0.09% CHAPS and 4.7 mM DTT).

Enzyme Preparation

Recombinant guinea pig liver TGase was over-expressed in *E. coli* and subsequently purified according to a published protocol (Norlund, M. A.; Lee, J. M.; Zainelli, G. M.; Muma, N. A. *Brain Res.* 1999, 851, 154). For kinetics runs, the chromogenic substrate Cbz-Glu(γ-p-nitrophenyl ester)Gly (Mastroberardino, P. G. et al *Cell Death Differ.* 2002, 9, 873) was used, at concentrations corresponding to $2\times K_M$ (55 μM) in the presence of 0.74-77 μM of each inhibitor contingent on the inhibitor's solubility. Stock solutions of all inhibitors were prepared in DMF such that the final concentration of this co-solvent was constant at 5% v/v.

General Procedure A: Synthesis of trans-cinnamoyl benzotriazolyl amides:trans-cinnamic acid (0.1 mmol) was dissolved in 2 mL of DMF, treated with DIC (0.25 mmol) and benzotriazole (0.25 mmol) and stirred overnight. In the case of 13b, 19b, 22b, 24b, 26d, 28d and 27d, the product precipitated and was collected by filtration and washed with 20 mL of diethyl ether. For 16b, 17b, 18b, 20b, 21b, 25b and 29c, the reaction mixture was diluted with 30 mL of EtOAc and washed with 3×5 mL of 1N HCl, 3×5 mL of 1N NaOH and 1×10 mL of brine. The organic layer was dried with $MgSO_4$, filtered and evaporated. The solid was recrystallized from EtOH (16b and 25b) or purified by flash chromatography (17b, 18b, 20b and 21b).

General Procedure B: Synthesis of substituted trans-cinnamic acids: In 3 mL of THF, (tert-butoxycarbonylmethyl) triphenylphosphonium bromide (0.33 mmol) and KHMDS (0.297 mmol) were dissolved and treated dropwise with a solution of the substituted benzaldehyde (0.165 mmol) in 1 mL THF. After stirring for 1 h, the reaction mixture was washed twice with 2 mL of saturated $NH_4Cl$, dried with $MgSO_4$ and evaporated to a residue that was passed through a short silica gel column (10 cm), eluting with EtOAc. The collected fractions were evaporated and the residue was dissolved in a minimum volume of DCM, cooled to 0° C. and treated with a 2-mL aliquot of TFA. After stirring for 4 h at 0° C., the volatiles were removed by azeotropic evaporation from a mixture of cyclohexane and acetone. The solid product thus obtained was triturated with ether and filtered.

General Procedure C: Aldol condensation: 3-Acetylpyridine (0.5 mmol) was dissolved in a 1:1 $H_2O$/MeOH solution (4 mL), treated with the substituted benzaldehyde (1.5 mmol) and KOH (1.5 mmol), stirred for 30 min. and filtered. The precipitated product, which was collected by filtration, was washed with a minimum amount of ethanol.

General Procedure D: Nitro group reduction with tin(II) chloride: The nitro aromatic analog (1 mmol) was dissolved in 5 mL of absolute ethanol, treated with $SnCl_2.2H_2O$ (5 mmol) heated to 70° C., stirred 30 minutes under $N_2$, treated with 30 mL of water and neutralized with a solution of 5% $NaHCO_3$. The aqueous phase was extracted with 3×20 mL of EtOAc. The combined organic phase was dried, filtered and evaporated to a residue that was purified by chromatography on silica gel with EtOAc as eluant.

General Procedure E: Synthesis of amides and esters of p-nitrocinnamic acid: p-Nitrocinnamoyl p-nitrophenyl ester (46, 0.16 mmol) was dissolved in 2 mL of $CH_2Cl_2$, treated with the specified alcohol or amine (0.18 mmol) using $Et_3N$ (0.48 mmol) as base. After stirring overnight at room temperature, the volatiles were removed and the resulting mixture was diluted with 30 mL of EtOAc. The organic phase was washed with 3×6 mL of 0.1N HCl, 8×6 mL of 1N NaOH and 2×5 mL of brine, dried with $MgSO_4$, filtered, and evaporated to a residue that was triturated with diethyl ether to give a solid.

General Procedure F: Azides 2a-l (Farmer, P. M.; Peck, A.; Terry, R. D. *J. Neuropathol. Exp. Neurol.* 1976, 35, 367). A stock solution of 0.5 M $NaN_3$ in DMSO was prepared after stirring for 24 h at room temperature. A 50 mL round-bottom flask equipped with a magnetic stir bar, was charged with a 0.5 M solution of $NaN_3$ (0.358 g, 5.5 mmol) in DMSO (11 mL) followed by the respective bromide (10 mmol). The mixture was stirred overnight at room temperature, treated with $H_2O$ (25 mL) [slightly exothermic] and stirred until it cooled to room temperature. The mixture was extracted with $Et_2O$ (3×15 mL). The $Et_2O$ extracts were combined, washed with $H_2O$ (2×15 mL) and once with brine (15 mL), dried over $MgSO_4$, filtered and evaporated under reduced pressure to afford the azide 2 suitably pure for the next step.

General Procedure G: 4-p-Nitrocinnamoyltriazoles 4a-n. A 5 mL round-bottom flask equipped with a magnetic stir bar, was charged with 5-(4'-nitrophenyl)pent-4-(E)-en-1-yn-3-one (3) (50 mg, 0.25 mmol), which was dissolved in 2.4 mL of a $H_2O/^tBuOH$ (1:1, v/v) solution. The ynone solution was then treated with azide 2 (0.25 mmol), followed by solutions of $CuSO_4$ (0.62 mg, 0.0025 mmol) in 10 μL of $H_2O$ and L-ascorbic acid sodium salt (5 mg, 0.025 mmol) in 25 μL of $H_2O$. The mixture was stirred overnight at 75° C., cooled to room temperature, treated with 40 mL of $H_2O$ and extracted with EtOAc (3×10 mL). The EtOAc extracts were combined, washed with brine (2×10 mL), dried over $MgSO_4$, filtered and evaporated under reduced pressure to a residue that was purified by chromatography on silica gel as described below to give cinnamoyltriazole 4.

p-Nitrocinnamoyl benzotriazolyl amide (15a): Amide 15a was prepared from p-nitrocinnamic acid using general procedure A, and isolated as a pale yellow solid (70% yield). mp 213-215° C. $^1$H NMR ($d_6$-DMSO) δ 8.27 (m, 8H), 7.81 (t, 1H, J=7.2 Hz), 7.64 (t, 1H, J=7.2 Hz). $^{13}$C NMR ($d_6$-DMSO) δ 168.09, 148.96, 142.38, 141.77, 139.67, 131.27, 130.35, 130.23, 126.43, 125.19, 124.98, 124.66, 115.93. HRMS (FAB) calcd for $C_{15}K_1N_4O_3$ ([M+H]$^+$): 295.0826. found 295.0816.

p-Nitrocinnamoyl oxybenzotriazolyl amide (14a): Amide 14a was prepared from p-nitrocinnamic acid using general procedure A, and isolated as a pale yellow solid (55% yield). mp 212-214° C. (dec.). $^1$H NMR ($d_6$-DMSO) δ 8.28 (d, 2H, J=8.8 Hz), 8.02 (d, 3H, J=8.6 Hz), 7.75 (d, 1H, J=8.3 Hz), 7.68 (d, 1H, J=16.1 Hz), 7.58 (t, 1H, J=6.9 Hz), 7.46 (t, 1H, J=8.2 Hz), 6.78 (d, 1H, J=16.1 Hz). $C_{15}H_{10}N_4O_4$ calc. C, 58.07; H, 3.25; N, 18.06. found C, 59.23; H, 3.35; N, 19.16. The structure of trifluoroacetate salt of 14a, which was crystallized in TFA, was solved at the Université de Montréal X-ray facility using direct methods (SHELXS 97) and refined with SHELXL 97: $C_{15}H_{10}N_4O_4.C_2HF_3O_2$; $M_r$=424.30; triclinic, colorless crystal; space group P1; unit cell dimension (Å) a=7.7137(2), b=9.7911(2), c=12.1711(2), α=96.2560 (10)°, β=107.4280(10)°, γ=96.4560(10)°; volume of unit cell (Å$^3$)=861.55(3); Z=2.

m-Nitrocinnamic acid (13b): Acid 13b was prepared from m-nitrobenzaldehyde using general procedure B, and isolated as a pale yellow solid (74% yield). mp 200-202° C. $^1$H NMR ($d_6$-DMSO) δ 8.50 (s, 1H), 8.21 (dd, 1H, J=8.2 Hz, 1.7 Hz), 8.17 (d, 1H, J=8.0 Hz), 7.69 (m, 2H), 6.73 (d, 1H, J=15.8 Hz). $^{13}$C NMR ($d_6$-DMSO) δ 158.01, 140.61, 134.36, 129.43, 127.48, 124.07, 118.61, 117.17, 116.65. HRMS (FAB) calcd for $C_9H_6NO_4$ ([M−H]$^-$): 192.0302. found 192.0310.

m-Nitrocinnamoyl oxybenzotriazolyl amide (14b): Amide 14b was prepared from acid 13b using general procedure A, and isolated as a pale yellow solid (52% yield). mp=184 to 186° C. $^1$H NMR ($CDCl_3$) δ 8.55 (d, 1H, J=7.5 Hz), 8.54 (s, 1H), 8.34 (d, 1H, J=8.2 Hz), 8.12 (d, 1H, J=15.8 Hz), 8.06 (m, 2H), 7.85 (m, 2H), 7.69 (m, 2H). HRMS (FAB) calcd for $C_{15}H_{11}N_4O_4$ ([M+H]$^+$): 311.0775. found 311.0769. $C_{15}H_{10}N_4O_4$ calcd C, 58.07; H, 3.25; N, 18.06. found C, 58.47; H, 3.83; N, 19.23.

o-Nitrocinnamic acid (13c): Acid 13c was prepared from o-nitrobenzaldehyde using general procedure B, and isolated as a pale yellow solid (58% yield). mp 243-245° C. $^1$H NMR ($d_6$-DMSO) 8.05 (dd, 1H, J=8.1 Hz, 1.2 Hz), 7.92 (dd, 1H, J=7.6 Hz, 1.1 Hz) 7.83 (d, 1H, J=15.8 Hz), 7.75 (t, 1H, J=7.4 Hz), 7.65 (t, 1H, J=8.1 Hz), 6.52 (d, 1H, J=15.8 Hz). $^{13}$C NMR ($d_6$-DMSO) δ 157.74, 140.59, 131.93, 127.33, 124.52, 123.19, 123.08, 118.87, 118.09. HRMS (FAB) calcd for $C_9H_6NO_4$ ([M−H]$^-$): 192.0302. found 192.0305.

o-Nitrocinnamoyl oxybenzotriazolyl amide (14c): This amide was prepared using general procedure A from acid 13c to give a pale yellow solid (53% yield). mp 182-184° C. $^1$H NMR ($CDCl_3$) δ 8.58 (d, 1H, J=13.6 Hz), 8.56 (d, 1H, J=9.4 Hz), 8.14 (dd, 1H, J=8.1 Hz, 1.1 Hz), 8.06 (d, 1H, J=8.3 Hz), 7.84 (m, 2H), 7.76 (t, 1H, J=6.5 Hz), 7.63 (m, 3H). $^{13}$C NMR ($d_6$-DMSO) δ 167.9, 149.23, 139.85, 134.82, 131.76, 130.36, 130.21, 128.81, 128.32, 126.02, 125.64, 125.48, 124.82, 120.12, 110.57. HRMS (FAB) calcd for $C_{15}H_{11}N_4O_4$ ([M+H]$^+$): 311.0775. found 311.0774.

p-Methoxycinnamoyl benzotriazolyl amide (15d): Amide 15d was prepared from p-methoxycinnamic acid using general procedure A, and isolated by crystallization from ethanol as a white solid (45% yield). mp 157-159° C. $^1$H NMR ($CDCl_3$) δ 8.43 (d, 1H, J=8.3 Hz), 8.14 (m, 2H), 8.01 (d, 1H, J=15.8 Hz), 7.72 (m, 3H), 7.53 (t, 1H, J=8.1 Hz), 6.99 (d, 2H, J=8.8 Hz) 3.89 (s, 3H). $^{13}$C NMR ($CDCl_3$) δ 164.55, 162.77, 148.92, 146.65, 131.86, 131.28, 130.49, 127.32, 126.42, 120.44, 115.19, 114.90, 113.63, 55.84. HRMS (FAB) calcd for $C_{16}H_{14}N_3O_2$ ([M+H]$^+$): 280.1081. found 280.1081.

m-Methoxycinnamic acid (13e): Acid 13e was prepared from m-methoxybenzaldehyde, using general procedure B, and isolated as a pale yellow solid (47% yield). mp 117-119° C. $^1$H NMR ($CDCl_3$) δ 7.75 (d, 1H, J=16.0 Hz), 7.30 (t, 1H, J=7.9 Hz), 7.13 (d, 1H, J=7.7 Hz), 7.05 (m, 1H), 6.95 (m, 1H), 6.43 (d, 1H, J=16.0 Hz), 3.82 (s, 3H). $^{13}$C NMR ($CDCl_3$) δ 165.42, 153.62, 141.78, 131.02, 126.06, 117.90, 114.69, 113.81, 110.61, 57.32. HRMS (FAB) calcd for $C_{10}H_{11}O_3$ ([M+H]$^+$): 179.0703. found 179.0703.

m-Methoxycinnamoyl benzotriazolyl amide (15e): Amide 15e was prepared from acid 13e using general procedure A, and isolated by a chromatography with EtOAc/Hexane (30:70) as eluant which provided white solid (28% yield). mp 159-161° C. $^1$H NMR ($CDCl_3$) δ 8.43 (d, 1H, J=8.3 Hz), 8.17 (d, 1H, J=8.3 Hz), 8.10 (s, 2H), 7.67 (td, 1H, J=8.0 Hz, 1 Hz), 7.55 (td, 1H, J=8.1 Hz, 1 Hz), 7.38 (m, 2H), 7.24 (m, 1H), 7.03 (m, 1H), 3.89 (s, 3H). $^{13}$C NMR ($CDCl_3$) δ 164.20, 160.32, 149.32, 146.64, 135.71, 131.75, 130.62, 130.41, 126.56, 122.19, 120.49, 117.95, 116.52, 115.13, 113.64, 55.75. HRMS (FAB) calcd for $C_{16}H_{13}N_3O_2Na$ ([M+Na]$^+$): 302.0900. found 302.0905.

o-Methoxycinnamic acid (13f): Acid 13f was prepared from o-methoxybenzaldehyde using general procedure B, and isolated as a pale yellow solid (46% yield). mp 182-184° C. $^1$H NMR ($CDCl_3$) δ 8.09 (d, 1H, J=16.1 Hz), 7.52 (dd, 1H, J=7.7 Hz, 1.6 Hz), 7.36 (td, 1H, J=7.5 Hz, 1.7 Hz), 6.92 (m, 2H), 6.54 (d, 1H, J=16.1 Hz), 3.88 (s, 3H). $^{13}$C NMR ($CDCl_3$) δ 173.41, 158.89, 142.87, 132.33, 129.61, 123.32, 121.06, 118.05, 111.50, 55.83. HRMS (FAB) calcd for $C_{10}H_{11}O_3$ ([M+H]$^+$): 179.0703. found 179.0702.

o-Methoxycinnamoyl benzotriazolyl amide (15f): Amide 15f was prepared from the acid 13f using general procedure A, and isolated by chromatography with EtOAc/hexane (30:70) as eluant as a pale yellow solid (33% yield). mp 159-161° C. $^1$H NMR ($CDCl_3$) δ 8.51 (d, 1H, J=16.0 Hz), 8.44 (dt, 1H, J=8.3 Hz, 0.9 Hz), 8.21 (d, 1H, J=16.0 Hz), 8.15 (dt, 1H, J=8.3 Hz, 0.9 Hz), 7.77 (dd, 1H, J=7.7 Hz, 1.7 Hz), 7.68 (td, 1H, J=7.1 Hz, 1.0 Hz), 7.52 (m, 2H), 7.04 (t, 1H, J=7.5 Hz), 6.98 (d, 1H, J=8.3 Hz), 3.95 (s, 3H). $^{13}$C NMR ($CDCl_3$) δ 164.61, 159.25, 146.46, 144.33, 133.02, 131.71, 130.30, 129.89, 126.25, 123.28, 121.01, 120.25, 116.30, 115.06, 111.48, 55.82. HRMS (FAB) calcd for $C_{16}H_{13}N_3O_2Na$ ([M+Na]$^+$): 302.0900. found 302.0907.

p-Methylcinnamoyl benzotriazolyl amide (15g): Amide 15g was prepared from p-methylcinnamic acid using general procedure A, and isolated as a white solid (22% yield). mp 146-148° C. $^1$H NMR ($CDCl_3$) δ 8.43 (d, 1H, J=8.3 Hz), 8.13 (m, 3H), 7.68 (m, 3H), 7.54 (t, 1H, J=8.2 Hz), 7.29 (d, 2H, J=8.0 Hz), 2.43 (s, 3H). $^{13}$C NMR ($CDCl_3$) δ 164.28, 149.04, 147.04, 142.45, 131.70, 131.67, 130.44, 130.07, 129.29, 126.37, 120.37, 115.08, 115.04, 21.90. HRMS (FAB) calcd for $C_{16}H_{14}N_3O$ ([M+H]$^+$): 264.1131. found 264.1130.

m-Methylcinnamic acid (13h): Acid 13h was prepared from m-methylbenzaldehyde using general procedure B, and isolated as a white solid (73% yield). mp 116-118° C. $^1$H NMR ($CDCl_3$) δ 7.76 (d, 1H, J=16.0 Hz), 7.28 (m, 4H), 6.43 (d, 1H, J=16.0 Hz), 2.37 (s, 3H). $^{13}$C NMR ($CDCl_3$) δ 173.22, 147.62, 138.94, 134.27, 131.92, 129.34, 129.15, 125.91, 117.40, 21.62. HRMS (FAB) calcd for $C_{10}H_{11}O_2$ ([M+H]$^+$): 163.0754. found 163.0747.

m-Methylcinnamoyl benzotriazolyl amide (15h): Amide 15h was prepared from the acid 13h using general procedure A, and isolated by flash chromatography with EtOAc/hexane (30:70) as eluant. Evaporation of the collected fractions gave a white solid (35% yield). mp 132-134° C. $^1$H NMR ($CDCl_3$) δ 8.43 (dt, 1H, J=8.3 Hz, 0.9 Hz), 8.16 (dt, 1H, J=8.3 Hz, 0.9 Hz), 8.13 (s, 3H), 7.69 (td, 1H, J=7.1 Hz, 1 Hz), 7.54 (m, 3H), 7.34 (m, 2H), 2.43 (s, 3H). $^{13}$C NMR ($CDCl_3$) δ 164.13, 19.15, 146.53, 139.03, 134.25, 132.57, 131.66, 130.45, 129.67, 129.19, 126.61, 126.40, 120.37, 115.91, 115.05, 21.57. HRMS (FAB) calcd for $C_{16}H_{14}N_3O$ ([M+H]$^+$): 264.1131. found 264.1131.

o-Methylcinnamic acid (13i): Acid 13i was prepared using general procedure B from o-methylbenzaldehyde and obtained as a salmon-coloured solid (67% yield). mp 174-176° C. $^1$H NMR ($CDCl_3$) δ 8.08 (d, 1H, J=15.9 Hz), 7.57 (d, 1H, J=7.4 Hz), 7.24 (m, 3H), 6.37 (d, 1H, J=15.9 Hz), 2.44 (s, 3H). $^{13}$C NMR ($d_6$-DMSO) δ 168.54, 142.11, 138.11, 133.87, 131.66, 130.92, 127.41, 127.38, 121.13, 20.26. HRMS (FAB) calcd for $C_{10}H_{11}O_2$ ([M+H]$^+$): 163.0754. found 163.0750.

o-Methylcinnamoyl benzotriazolyl amide (15i): Amide 15i was prepared from the acid 13i, using general procedure A, and isolated by flash chromatography using EtOAc/hexane (30:70) as eluant. Evaporation of the collected fractions yielded a white solid (41% yield). mp 127-129° C. $^1$H NMR ($CDCl_3$) δ 8.45 (d, 1H, J=15.8 Hz), 8.40 (d, 1H, J=8.3 Hz), 8.14 (d, 1H, J=8.3 Hz), 8.05 (d, 1H, J=15.8 Hz), 7.67 (td, 1H, J=7.2 Hz, 0.7 Hz), 7.67 (td, 1H, J=8 Hz, 0.8 Hz), 7.31 (m, 3H), 2.54 (s, 3H). $^{13}C$ NMR ($CDCl_3$) δ 164.19, 146.54, 146.36, 138.99, 133.15, 131.68, 131.47, 131.30, 130.49, 127.27, 126.82, 126.42, 120.40, 116.94, 115.01, 20.12. HRMS (FAB) calcd for $C_{16}K_4N_3O$ ($[M+H]^+$): 264.1131. found 264.1123.

p-Chlorocinnamic acid (13k): Acid 13k was prepared using general procedure B from p-chlorobenzaldehyde and obtained as a white solid (49% yield). mp 247-249° C. $^1H$ NMR ($d_6$-DMSO) δ 7.71 (d, 2H, J=8.5 Hz), 7.56 (d, 1H, J=16.1 Hz), 7.45 (d, 2H, J=8.5 Hz), 6.54 (d, 1H, J=16.0 Hz). $^{13}C$ NMR ($d_6$-DMSO) δ 168.45, 143.51, 135.71, 134.19, 130.90, 129.90, 121.05. HRMS (FAB) calcd for $C_9H_6ClO_2$ ($[M-H]^-$): 181.0062. found 181.0057.

p-Chlorocinnamoyl benzotriazolyl amide (15k): Amide 15k was prepared using general procedure A from acid 13k and obtained as a white solid (48% yield). mp 191-193° C. $^1H$ NMR ($CDCl_3$) δ 8.41 (dt, 1H, J=8.3 Hz, 0.9 Hz), 8.16 (dt, 1H, J=8.3 Hz, 0.9 Hz), 8.10 (s, 2H), 7.68 (m, 3H), 7.54 (td, 1H, J=7.2 Hz, 1.1 Hz), 7.44 (m, 2H). $^{13}C$ NMR ($CDCl_3$) δ 164.01, 147.48, 146.65, 137.82, 132.88, 131.70, 130.72, 130.44, 129.75, 126.66, 120.56, 116.85, 115.10. HRMS (FAB) calcd for $C_{15}H_{11}ClN_3O$ ($[M+H]^+$): 284.0585. found 284.0598.

m-Chlorocinnamoyl oxybenzotriazolyl amide (14l): Amide 14l was prepared using general procedure A from m-chlorocinnamic acid and obtained as a white solid (64% yield). mp 210-212° C. (dec.). $^1H$ NMR ($CDCl_3$) δ 8.53 (d, 1H, J=8.4 Hz), 8.05 (d, 1H, J=6.7 Hz), 8.01 (d, 1H, J=14.1 Hz), 7.83 (td, 1H, J=8.3 Hz, 1.1 Hz), 7.67 (m, 4H), 7.44 (m, 2H). $^{13}C$ NMR ($CDCl_3$) δ 161.15, 147.20, 135.47, 135.13, 132.95, 132.86, 132.77, 131.31, 130.26, 128.57, 126.89, 116.32, 116.21, 115.48. HRMS (FAB) calcd for $C_{15}H_{11}ClN_3O_2$ ($[M+H]^+$): 300.0534. found 300.0520.

o-Chlorocinnamic acid (13m): Acid 13m was prepared using general procedure B from o-chlorobenzaldehyde and obtained as a white solid (56% yield). mp 206-208° C. $^1H$ NMR ($d_6$-DMSO) δ 7.91 (dd, 1H, J=7.4 Hz, 1.9 Hz), 7.85 (d, 1H, J=16.0 Hz), 7.52 (dd, 1H, J=8.0 Hz, 1.7 Hz), 7.39 (m, 2H), 6.59 (d, 1H, J=15.9 Hz). $^{13}C$ NMR ($d_6$-DMSO) δ 168.18, 139.68, 134.57, 132.83, 132.63, 130.91, 129.19, 128.72, 123.26. HRMS (FAB) calcd for $C_9H_6ClO_2$ ($[M-H]^-$): 181.0062. found 181.0062.

o-Chlorocinnamoyl benzotriazolyl amide (15m): Amide 15m was prepared using general procedure A from the acid 13m as white solid (37% yield). mp 144-146° C. $^1H$ NMR ($CDCl_3$) δ 8.58 (d, 1H, J=15.9 Hz), 8.40 (d, 1H, J=8.2 Hz), 8.14 (d, 1H, J=8.2 Hz), 8.12 (d, 1H, J=15.9 Hz), 7.91 (dd, 1H, J=6.7 Hz, 2.0 Hz), 7.68 (t, 1H, J=8.1 Hz), 7.53 (m, 2H), 7.37 (m, 2H). $^{13}C$ NMR ($CDCl_3$) δ 163.83, 146.68, 144.63, 136.28, 132.64, 132.50, 131.75, 130.80, 130.75, 128.54, 127.64, 126.72, 120.57, 118.73, 115.14. HRMS (FAB) calcd for $C_{15}H_{11}ClN_3O$ ($[M+H]^+$): 284.0585. found 284.0587.

Cinnamoyl benzotriazolyl amide (15j): Amide 15j was prepared using general procedure A from trans-cinnamic acid followed by recristalization from ethanol, as white solid (23% yield). mp 171-173° C. (dec.). $^1H$ NMR ($CDCl_3$) δ 8.43 (d, 1H, J=7.4 Hz), 8.16 (m, 3H), 7.77 (m, 2H), 7.70 (td, 1H, J=7.1 Hz, 1 Hz), 7.55 (td, 1H, J=7.2 Hz, 1.0 Hz), 7.49 (m, 3H). $^{13}C$ NMR ($CDCl_3$) δ 171.51, 146.38, 137.55, 130.90, 129.43, 129.33, 128.56, 128.37, 128.33, 127.18, 126.65, 120.51, 114.61. HRMS (FAB) calcd for $C_{15}H_{12}N_3O$ ($[M+H]^+$): 250.0975. found 250.0966.

p-Nitrocinnamoyl t-butyl ester (20a): (tert-Butoxycarbonylmethyl)triphenylphosphonium bromide (0.33 mmol) and KHMDS (0.297 mmol) were dissolved in 3 mL of THF. p-Nitrobenzaldehyde (0.165 mmol) was dissolved in 1 mL THF and added dropwise to the ylide suspension. The mixture was stirred for 1 hour. The organic phase was then treated twice with 2 mL of saturated $NH_4Cl$, dried with $MgSO_4$ and the volatiles were removed by rotary evaporation. The product was purified by chromatography with EtOAc/hexane 20:80 as eluant to give a pale yellow solid (75% yield). mp 146-148° C. $^1H$ NMR ($CDCl_3$) δ 8.21 (d, 2H, J=8.9 Hz), 7.63 (d, 2H, J=8.9 Hz), 7.60 (d, 1H, J=16.1 Hz), 6.47 (d, 1H, J=16.0 Hz), 1.52 (s, 9H). $^{13}C$ NMR ($CDCl_3$) δ 165.55, 148.56, 141.13, 140.86, 128.79, 124.80, 124.40, 81.57, 28.38. HRMS (FAB) calcd for $C_{13}H_{15}NO_4Na$ ($[M+Na]^+$): 272.0893. found 272.0895.

p-Aminocinnamic acid (13r): Acid 13r was prepared using general procedure D from the ester 20a to give a product that was diluted in a minimum of $CH_2Cl_2$ and treated with TFA (3 mL) at 0° C. for 4 hours. The volatiles were removed under vacuum and the product triturated with diethyl ether to give an orange solid (64% yield). mp 265-267° C. (dec.). $^1H$ NMR ($CD_3OD$) δ 7.73 (d, 2H, J=8.5 Hz), 7.67 (d, 1H, J=16.1 Hz), 7.40 (d, 2H, J=8.5 Hz), 6.52 (d, 1H, J=16.0 Hz). $^{13}C$ NMR ($CD_3OD$) δ 161.07, 137.51, 130.53, 127.64, 125.14, 119.63, 116.48. HRMS (FAB) calcd for $C_9H_9NO_2$ ($[M+H]^+$): 164.0706. found 164.0709.

p-(tert-Butoxycarbonylamino)cinnamic acid (13n): Acid 13n (0.5 mmol) was dissolved in 5 mL of a dioxane/$H_2O$ (1:1) solution, treated with di-tert-butyl dicarbonate ($(BOC)_2O$) (0.6 mmol) and solid $NaHCO_3$ (5 mmol), stirred overnight at room temperature and evaporated to a residue that was diluted with 40 mL 1N NaOH. The aqueous phase was washed with 3×10 mL of $CH_2Cl_2$, and neutralized with 1N HCl. The acid was extracted with 3×10 mL of EtOAc. The combined organic phase was dried with $MgSO_4$ and filtered. The volatiles were removed and the product was obtained without further purification as a white solid (45% yield). mp 195-197° C. (dec.). $^1H$ NMR ($CD_3OD$) δ 7.61 (d, 1H, J=16.0 Hz), 7.47 (d, 4H, J=5.4 Hz), 6.35 (d, 1H, J=15.9 Hz), 1.51 (s, 9H). $^{13}C$ NMR ($CD_3OD$) δ 171.63, 155.66, 147.02, 143.71, 130.89, 130.67, 120.32, 117.84, 82.04, 29.49. HRMS (FAB) calcd for $C_{14}H_{17}NO_4Na$ ($[M+Na]^+$): 286.1050. found 286.1045.

p-(tert-Butoxycarbonylamino)cinnamoyl benzotriazolyl amide (15n): Amide 15n was prepared using general procedure A from acid 13n, as a pale yellow solid (61% yield). mp 227-229° C. $^1H$ NMR ($d_6$-DMSO) δ 9.77 (s, 1H), 8.33 (d, 1H, J=8.2 Hz), 8.27 (d, 1H, J=8.2 Hz), 8.07 (d, 1H, J=15.8 Hz), 7.93 (d, 1H, J=15.9 Hz), 7.82 (m, 3H), 7.60 (m, 3H), 1.48 (s, 9H). $^{13}C$ NMR ($d_6$-DMSO) δ 164.58, 153.45, 149.27, 146.60, 143.94, 131.90, 131.58, 131.35, 128.43, 127.42, 121.03, 118.93, 115.32, 114.11, 80.65, 29.00. HRMS (FAB) calcd for $C_{20}H_{20}N_4O_3Na$ ($[M+Na]^+$): 387.1428. found 387.1425.

m-(tert-Butoxycarbonylamino)cinnamoyl benzotriazolyl amide (15o): Amide 15o was prepared according to the same method as described for amide 15n to give a white solid (15% yield). mp 195-197° C. (dec.). $^1H$ NMR ($CDCl_3$) δ 8.40 (d, 1H, J=8.2 Hz), 8.13 (d, 1H, J=8.3 Hz), 8.09 (s, 2H), 7.76 (s, 1H), 7.67 (t, 1H, J=8.0 Hz), 7.51 (m, 4H), 6.56 (s, 1H), 1.51 (s, 9H). $^{13}C$ NMR ($CDCl_3$) δ 164.17, 152.96, 148.89, 146.63, 139.54, 135.20, 131.75, 130.62, 130.02, 126.56, 123.90, 121.75, 120.49, 118.90, 116.69, 115.14, 81.31, 28.65. HRMS (FAB) calcd for $C_{20}H_{21}N_4O_3$ ($[M+H]^+$): 365.1608. found 365.1607.

p-(9-Fluorenylmethoxycarbonylamino)cinnamic acid (13p): Acid 13r (0.5 mmol) was dissolved in 5 mL of a dioxane/$H_2O$ (1:1) solution, treated with 9-fluorenylmethoxycarbonyl chloride (Fmoc-C1) (0.6 mmol) using $NaHCO_3$ (5 mmol) as base. The mixture was stirred overnight at room temperature. Then the solvent was reduced and the residue was diluted in 40 mL of water. The aqueous phase was acidified with 6N HCl. The acid was extracted with 3×10 mL of EtOAc. The organic phase was dried with $MgSO_4$ and filtered. The solvent was removed and the product obtained after trituration with diethyl ether as an orange solid (37% yield). mp 270-272° C. (dec.). $^1$H NMR ($d_6$-DMSO) δ 9.92 (s, 1H), 7.90 (d, 2H, J=7.3 Hz), 7.73 (d, 2H, J=7.4 Hz), 7.45 (m, 9H), 6.37 (d, 1H, J=16.0 Hz), 4.50 (d, 2H, J=6.4 Hz), 4.30 (t, 1H, J=6.4 Hz). $^{13}$C NMR ($d_6$-DMSO) δ 158.59, 145.21, 136.41, 136.36, 133.90, 133.75, 122.95, 122.28, 121.67, 121.15, 119.28, 114.76, 112.86, 111.88, 64.60, 47.00. HRMS (FAB) calcd for $C_{24}H_{20}NO_4$ ([M+H]$^+$): 386.1387. found 386.1383.

p-(9-Fluorenylmethoxycarbonylamino)cinnamoyl benzotriazolyl amide (15p): Amide 15p was prepared using general procedure A from the acid 13p as a yellow solid (12% yield). mp 219-221° C. (dec.). $^1$H NMR ($d_6$-DMSO) 810.09 (s, 1H), 8.33 (d, 1H, J=8.2 Hz), 8.27 (d, 1H, J=8.1 Hz), 7.84 (m, 9H), 7.59 (m, 3H), 7.35 (m, 4H), 4.52 (d, 2H, J=6.1 Hz), 4.32 (t, 1H, J=6.5 Hz). HRMS (FAB) calcd for $C_{30}H_{22}N_4O_3Na$ ([M+Na]$^+$): 509.1584. found 509.1581. $C_{30}H_{22}N_4O_3$ calcd C, 74.06; H, 4.56; N, 11.52. found C, 73.44; H, 4.68; N, 11.85.

p-(Methoxycarbonyl)benzaldehyde (40q): 4-Carboxybenzaldehyde (2 mmol) was diluted in 6 mL of anhydrous MeOH. The mixture under $N_2$ was placed in an ice bath and acetyl chloride (10 mmol) was added dropwise. The ice bath was removed and the mixture was stirred overnight at room temperature. The methanol was removed under reduced pressure and the mixture was diluted in 35 mL of EtOAc. The organic phase was washed with 5×10 mL of 1N NaOH and 3×10 mL of brine, dried with $MgSO_4$ and filtered. The volatiles were removed and the product was obtained as a pale yellow solid (96% yield). mp 142-144° C. $^1$H RMN ($CDCl_3$) δ10.04 (s, 1H), 8.13 (d, 2H, J=8.2 Hz), 7.89 (d, 2H, J=8.1 Hz), 3.90 (s, 3H). $^{13}$C NMR ($CDCl_3$) δ 191.91, 166.26, 139.35, 135.27, 130.40, 129.74, 52.81. HRMS (FAB) calcd for $C_9H_9O_3$ ([M+H]$^+$): 165.0546. found 165.0543.

p-(Methoxycarbonyl)cinnamic acid (13q): Acid 13q was prepared using general procedure B, from the aldehyde 40q as white solid (40% yield). mp 245-247° C. $^1$H NMR ($d_6$-DMSO) δ 7.94 (d, 2H, J=8.4 Hz), 7.81 (d, 2H, J=8.4 Hz), 7.62 (d, 1H, J=16.1 Hz), 6.64 (d, 1H, J=16.1 Hz), 3.84 (s, 3H). $^{13}$C NMR ($d_6$-DMSO) δ 168.54, 166.72, 143.43, 139.73, 131.53, 130.56, 129.38, 122.87, 53.24. HRMS (FAB) calcd for $C_{11}H_9O_4$ ([M−H]$^-$): 205.0506. found 205.0504.

p-(Methoxycarbonyl)cinnamoyl benzotriazolyl amide (15q): Amide 15q was prepared using general procedure A, from the acid, 13q to give a white solid (39% yield). mp 224-226° C. $^1$H NMR ($d_6$-DMSO) δ 8.32 (d, 1H, J=8.2 Hz), 8.27 (d, 1H, J=8.3 Hz), 8.16 (s, 2H), 8.05 (m, 4H), 7.80 (td, 1H, J=7.2 Hz, 1.0 Hz), 7.63 (td, 1H, J=7.2 Hz, 1.0 Hz), 3.86 (s, 3H). $^{13}$C NMR ($d_6$-DMSO) δ 176.52, 164.24, 163.33, 147.27, 132.57, 131.90, 130.81, 130.36, 121.20, 115.35, 53.41. HRMS (FAB) calcd for $C_{12}H_{14}N_3O_3$ ([M+H]$^+$): 308.1030. found 308.1028.

p-Nitrobenzyloxycarbonylbenzotriazole (32a): p-Nitrobenzyl chloroformate (0.5 mmol) was dissolved in 5 mL of $CH_2Cl_2$ and treated with benzotriazole (0.5 mmol) using $Et_3N$ (2 mmol) as base. The mixture was stirred overnight at room temperature, diluted with $CH_2Cl_2$ (20 mL) and washed with 3×5 mL of 1N HCl, 2×5 mL of 1N NaOH and 1×5 mL of brine. The organic phase was dried and filtered. The volatiles were removed and the product was triturated with diethyl ether to provide a pale yellow solid (59% yield). mp 160-162° C. $^1$H NMR ($CDCl_3$) δ 8.27 (d, 1H, J=8.9 Hz), 8.17 (m, 3H), 7.72 (d, 1H, J=8.9 Hz), 7.65 (td, 1H, J=8.3 Hz, 1.1 Hz), 7.53 (m, 2H), 5.26 (s, 2H). $^{13}$C NMR ($CDCl_3$) δ 154.84, 146.17, 142.27, 141.30, 132.01, 130.82, 128.78, 126.37, 124.16, 120.86, 113.58, 68.66. HRMS (FAB) calcd for $C_{14}H_{11}N_4O_4$ ([M+H]$^+$): 299.0775. found 297.0775.

p-Nitrohydrocinnamoyl benzotriazolylamide (33a): Amide 33a was prepared using general procedure A, from p-nitrohydrocinnamic acid.[64] Chromatography with EtOAc/hexane (30:70) as eluant gave a pale yellow solid (60% yield). mp 134-136° C. $^1$H NMR ($CDCl_3$) δ 8.27 (d, 1H, J=8.2 Hz), 8.19 (d, 2H, J=8.7 Hz), 8.13 (d, 1H, J=8.3 Hz), 7.67 (t, 1H, J=8.2 Hz), 7.52 (m, 3H), 3.83 (t, 2H, J=7.4 Hz), 3.35 (t, 2H, J=7.4 Hz). $^{13}$C NMR ($CDCl_3$) δ 171.15, 147.83, 146.48, 130.96, 130.83, 129.76, 126.69, 125.47, 124.22, 120.59, 114.60, 36.62, 30.14. HRMS (FAB) calcd for $C_{15}H_{13}N_4O_3$ ([M+H]$^+$): 297.0982. found 297.0977.

p-Nitrobenzoyl benzotriazolyl amide (34a): p-Nitrobenzoyl chloride (0.5 mmol) was dissolved in 5 mL of $CH_2Cl_2$ and treated with benzotriazole (0.5 mmol) and $Et_3N$ (2 mmol). The mixture was stirred overnight at room temperature, diluted with $CH_2Cl_2$ (20 mL) and washed with 3×5 mL of 1N HCl, 2×5 mL of 1N NaOH and 1×5 mL of brine, dried over $MgSO_4$ and filtered. The volatiles were removed under reduced pressure and the product was triturated with diethyl ether to give a white solid (49% yield). mp 194-196° C. $^1$H NMR ($CDCl_3$) δ 8.39 (m, 5H), 8.19 (dt, 1H, J=8.3 Hz, 0.9 Hz), 7.75 (td, 1H, J=8.2 Hz, 1.0 Hz), 7.60 (td, 1H, J=8.2 Hz, 1.0 Hz). $^{13}$C NMR ($CDCl_3$) δ 165.33, 150.78, 146.19, 137.22, 132.98, 132.27, 131.38, 127.31, 123.81, 120.85, 115.08. HRMS (FAB) calcd for $C_{13}H_9N_4O_3$ ([M+H]$^+$): 269.0669. found 269.0676.

p-Nitrocinnamoyl oxyazabenzotriazolyl amide (16a): Amide 16a was prepared using general procedure A, from 1-hydroxy-1-azabenzotriazole and obtained as a white solid (58% yield). mp 195-197° C. (dec.). $^1$H NMR ($d_6$-DMSO) δ 8.81 (d, 1H, J=4.4 Hz), 8.58 (d, 1H, J=8.4 Hz), 8.28 (d, 2H, J=8.7 Hz), 8.03 (d, 2H, J=8.7 Hz), 7.74 (d, 1H, J=16.1 Hz), 7.56 (dd, 1H, J=8.4 Hz, 4.4 Hz), 6.79 (d, 1H, J=16.1 Hz). $C_{14}H_9N_5O_4$ calcd C, 54.02; H, 2.91; N, 22.50. found C, 55.34; H, 3.16; N, 23.46.

p-Nitrocinnamoyl imidazolyl amide (18a): Amide 18a was prepared using general procedure E, from imidazole in acetone to give a white solid (68% yield). mp 178-179° C. (dec.). $^1$H NMR ($d_6$-DMSO) δ 8.82 (s, 1H), 8.32 (d, 2H, J=8.9 Hz), 8.20 (d, 2H, J=8.9 Hz), 8.09 (d, 1H, J=15.6 Hz), 7.96 (t, 1H, J=1.31 Hz), 7.85 (d, 1H, J=15.5 Hz), 7.17 (t, 1H, J=0.9 Hz). $^{13}$C NMR ($d_6$-DMSO) δ 157.96, 140.26, 134.05, 133.72, 128.50, 124.02, 123.11, 118.25, 118.19, 118.12. HRMS (FAB) calcd for $C_{12}H_{10}N_3O_3$ ([M+H]$^+$): 244.0717. found 244.0727.

p-Nitrocinnamoyl benzyl ester (19a): Ester 19a was prepared using general procedure E from benzyl alcohol and purified by chromatography using EtOAc/Hexane 30:70 as eluant to give a yellow solid (80% yield). mp 112-114° C. $^1$H NMR ($CDCl_3$) δ 8.22 (d, 2H, J=8.8 Hz), 7.72 (d, 1H, J=16.1 Hz), 7.64 (d, 2H, J=8.8 Hz), 7.38 (m, 5H), 6.58 (d, 1H, J=16.1 Hz), 5.25 (s, 2H). $^{13}$C NMR ($CDCl_3$) δ 166.13, 148.79, 142.47, 140.70, 135.90, 128.97, 128.77, 128.69, 124.47 (2C), 122.46, 67.12. HRMS (FAB) calcd for $C_{16}K_4NO_4$ ([M+H]$^+$): 284.0917. found 284.0931 p-Nitrocinnamoyl benzyl amide (21a): Amide 21a was prepared using general procedure E from benzyl amine as pale yellow solid (63% yield). mp 188-190° C. $^1$H NMR ($d_6$-DMSO) δ 8.76 (t, 1H, J=5.8 Hz), 8.24 (d, 2H, J=8.8 Hz), 7.82 (d, 2H, J=8.8 Hz), 7.57 (d. 1H, J=15.8 Hz), 7.30 (m, 5H), 6.86 (d, 1H, J=15.9 Hz), 4.40 (d, 2H, J=5.9 Hz). $^{13}$C NMR ($d_6$-DMSO) δ 155.32, 139.88, 134.37, 132.17, 129.93, 122.49, 122.28, 121.40, 120.95, 120.36, 118.36, 43.15. HRMS (FAB) calcd for $C_{16}H_{15}N_2O_3$ ([M+H]$^+$): 283.1077. found 283.1076.

p-Nitrocinnamoyl phenyl amide (22a): Amide 22a was prepared using general procedure E from aniline and purified by chromatography with EtOAc/hexane 40:60 as eluant to give a yellow solid (61% yield). mp 209-211° C. $^1$H NMR ($d_6$-DMSO) δ 10.35 (s, 1H), 8.28 (d, 2H, J=8.7 Hz), 7.87 (d, 2H, J=8.6 Hz), 7.69 (d, 2H, J=9.4 Hz), 7.68 (d, 1H, J=15.0 Hz), 7.33 (t, 2H, J=7.5 Hz), 7.07 (t, 1H, J=7.2 Hz), 7.00 (d, 1H, J=15.7 Hz). $^{13}$C NMR ($d_6$-DMSO) δ 163.77, 148.58, 142.26, 139.99, 138.66, 129.83, 129.71, 127.53, 125.14, 124.62, 120.26. HRMS (FAB) calcd for $C_{15}H_{13}N_2O_3$ ([M+H]$^+$): 269.0921. found 269.0915.

p-Nitrocinnamoyl naphtalenyl amide (23a): Amide 23a was prepared using general procedure E from 1-aminonaphtalene and obtained as a yellow solid (61% yield). mp 278-280° C. (dec.). $^1$H NMR ($d_6$-DMSO) δ 10.28 (s, 1H), 8.31 (d, 2H, J=8.6 Hz), 8.14 (d, 1H, J=9.2 Hz), 7.93 (m, 4H), 7.78 (d, 1H, J=7.8 Hz), 7.74 (d, 1H, J=15.6 Hz), 7.55 (m, 3H), 7.33 (d, 1H, J=15.7 Hz). $^{13}$C NMR ($d_6$-DMSO) δ 164.61, 148.59, 142.43, 138.82, 134.69, 134.28, 129.74, 129.25, 128.13, 127.60, 127.10, 126.94, 126.61, 126.29, 125.15, 123.45, 121.92. HRMS (FAB) calcd for $C_{19}H_{15}N_2O_3$ ([M+H]$^+$): 319.1077. found 319.1066.

p-Nitrocinnamoyl piperidinyl amide (24a): Amide 24a was prepared using general procedure E from piperidine and obtained as a pale yellow solid (95% yield). mp 170-172° C. $^1$H NMR δ 8.21 (d, 2H, J=8.8 Hz), 7.65 (d, 2H, J=8.8 Hz), 7.64 (d, 1H, J=15.4 Hz), 7.05 (d, 1H, J=15.6 Hz), 3.66 (m, 2H), 3.60 (m, 2H), 1.63 (m, 6H). $^{13}$C NMR δ 164.6, 148.2, 142.1, 139.6, 128.5, 124.4, 122.5, 47.4, 43.7, 27.0, 25.9, 24.8. HRMS (FAB) calcd for $C_{14}H_{17}N_2O_3$ ([M+H]$^+$): 261.1234. found 261.1224.

p-Nitrocinnamoyl indolinyl amide (25a): Amide 25a was prepared using general procedure E from indoline and obtained as a yellow solid (42% yield). mp 290-292° C. (dec.). $^1$H NMR ($CDCl_3$) δ 8.35 (d, 1H, J=7.8 Hz), 8.27 (d, 2H, J=8.8 Hz), 7.86 (d, 1H, J=15.3 Hz), 7.72 (d, 2H, J=8.8 Hz), 7.26 (m, 2H), 7.08 (t, 1H, J=7.4 Hz), 7.00 (d, 1H, J=15.3 Hz), 4.32 (t, 2H, J=8.4 Hz), 3.29 (t, 2H, J=7.8 Hz). $^{13}$C NMR ($CDCl_3$) δ 163.47, 148.56, 141.61, 140.87, 140.78, 132.38, 128.89, 128.05, 124.75, 124.62, 124.52, 123.45, 118.05, 48.51, 28.35. HRMS (FAB) calcd for $C_{17}H_{15}N_2O_3$ ([M+H]$^+$): 295.1077. found 295.1067.

p-Nitrocinnamoyl dibenzyl amide (26a): Amide 26a was prepared using general procedure E from dibenzylamine and obtained as a yellow solid (64% yield). mp 142-144° C. $^1$H NMR ($CDCl_3$) δ 8.17 (d, 2H, J=8.8 Hz), 7.84 (d, 1H, J=15.4 Hz), 7.56 (d, 2H, J=8.8 Hz), 7.29 (m, 10H), 6.98 (d, 1H, J=15.4 Hz), 4.71 (s, 2H), 4.60 (s, 2H). $^{13}$C NMR ($CDCl_3$) δ 166.11, 147.99, 141.23, 140.84, 136.81, 136.23, 129.01, 128.59, 128.30, 127.81, 127.51, 126.33, 123.96, 121.52, 50.04, 48.95. HRMS (FAB) calcd for $C_{23}H_{21}N_2O_3$ ([M+H]$^+$): 373.1547. found 373.1534.

p-Nitrocinnamoyl methylbenzyl amide (27a): Amide 27a was prepared using general procedure E from N-methylbenzylamine and obtained as a yellow crystalline solid (73% yield). mp 129-131° C. The NMR spectra showed mixtures of amide isomers (1:1). $^1$H NMR ($CDCl_3$) δ 8.28 (d, 2H, J=8.6 Hz), 8.23 (d, 2H, J=8.6 Hz), 7.85 (d, 1H, J=5.9 Hz), 7.80 (d, 1H, J=5.9 Hz), 7.72 (d, 2H, J=8.7 Hz), 7.63 (d, 2H, J=8.6 Hz), 7.35 (m, 10H), 7.12 (d, 1H, J=15.5 Hz), 7.03 (d, 1H, J=15.4 Hz), 4.77 (s, 2H), 4.76 (s, 2H), 3.16 (s, 3H), 3.14 (s, 3H). $^{13}$C NMR ($CDCl_3$) δ 166.72, 165.81, 148.39, 141.82, 140.64, 137.20, 129.42, 129.02, 128.72, 128.44, 128.26, 127.89, 126.67, 124.45, 124.40, 121.97, 53.88, 51.75, 35.36, 34.92. HRMS (FAB) calcd for $C_{17}H_{17}N_2O_3$ ([M+H]$^+$): 297.1234. found 297.1244.

(E)-3-(4-nitrophenyl)-1-(pyridin-3-yl)prop-2-en-1-one (30a): Ketone 30a was prepared using general procedure C from p-nitrobenzaldehyde and obtained as a pale yellow solid (75% yield). mp 182-184° C. $^1$H NMR ($CDCl_3$) δ 9.23 (s, 1H), 8.82 (d, 1H, J=3.7 Hz), 8.29 (m, 3H), 7.80 (m, 3H), 7.58 (d, 1H, J=15.7 Hz), 7.48 (m, 1H). $^{13}$C NMR ($CDCl_3$) δ 188.69, 153.99, 150.09, 149.10, 142.97, 140.80, 136.33, 133.22, 129.48, 125.17, 124.63, 124.21. HRMS (FAB) calcd for $C_{14}K_1N_2O_3$ ([M+H]$^+$): 255.0764. found 255.0769.

(E)-3-(4-nitrophenyl)-1-phenylprop-2-en-1-one (31a): Ketone 31a was prepared using general procedure C, from p-nitrobenzaldehyde and acetophenone, and obtained as pale yellow solid (89% yield). mp 162-164° C. $^1$H NMR ($CDCl_3$) δ 8.25 (d, 2H, J=8.8 Hz), 8.02 (d, 2H, J=8.6 Hz), 7.78 (m, 3H), 7.61 (m, 4H). $^{13}$C NMR ($CDCl_3$) δ 189.91, 148.82, 141.80, 141.32, 137.79, 133.69, 129.25, 129.12, 128.89, 125.96, 124.51. HRMS (FAB) calcd for $C_{15}H_{12}NO_3$ ([M+H]$^+$): 254.0812. found 254.0809.

(E)-3-(4-aminophenyl)-1-(pyridin-3-yl)prop-2-en-1-one (30r): Ketone 30r was prepared using general procedure D from azachalcone 30a and obtained as pale orange solid (57% yield). mp 167-169° C. $^1$H NMR ($CDCl_3$) δ 9.18 (d, 1H, J=1.6 Hz), 8.76 (dd, 1H, J=4.8 Hz, 1.6 Hz), 8.25 (dt, 1H, J=8.0 Hz, 1.9 Hz), 7.77 (d, 1H, J=15.5 Hz), 7.46 (m, 3H), 7.28 (d, 1H, J=15.5 Hz), 6.67 (d, 2H, J=8.6 Hz), 4.07 (s, 2H). $^{13}$C NMR ($CDCl_3$) δ 180.49, 146.89, 144.29, 144.04, 141.53, 131.49, 129.90, 126.89, 120.98, 120.22, 114.08, 112.11. HRMS (FAB) calcd for $C_{14}H_{13}N_2O$ ([M+H]$^+$): 225.1022. found 250.1027.

(E)-3-(4-acetylaminophenyl)-1-(pyridin-3-yl)prop-2-en-1-one (30t): Ketone 30t was prepared from aniline 30r (0.045 mmol.), treated with 500 μL of a solution 40% anhydrous acetic in pyridine at room temperature for 2 hours. The solvent was removed and the product was precipitated with 1N NaOH. The solid was washed with water and obtained as a yellow solid (77% yield). mp 191-193° C. $^1$H NMR ($CDCl_3$) δ 9.21 (s, 1H), 8.79 (s, 1H), 8.27 (dt, 1H, J=7.9 Hz, 1.8 Hz), 7.78 (d, 1H, J=15.7 Hz), 7.59 (s, 4H), 7.39 (m, 3H), 2.19 (s, 3H). $^{13}$C NMR ($CDCl_3$) δ 189.42, 169.02, 153.39, 149.99, 145.83, 140.87, 136.29, 133.97, 130.08, 124.07, 120.50, 120.03, 25.11. HRMS (FAB) calcd for $C_{16}H_{15}N_2O_2$ ([M+H]$^+$): 267.1128. found 267.1141.

p-Nitrocinnamoyl p-nitrophenyl ester (17a): Ester 17a was prepared by treating p-nitrocinnamic acid (1 mmol) in acetonitrile (6 mL) with $Et_3N$ (1 mmol) and DMAP (0.1 mmol) at room temperature for 5 minutes, followed by p-nitrophenyl chloroformate (1.1 mmol) and stirring 1 hour. The precipitate was filtered and washed with 5 mL of acetonitrile which gave a pale yellow solid (94% yield). mp 181-183° C. $^1$H NMR ($CDCl_3$) δ 8.32 (d, 2H, J=9.1 Hz), 8.27 (d, 2H, J=8.8 Hz), 8.10 (d, 2H, J=8.9 Hz), 8.02 (d, 1H, J=16.1 Hz), 7.54 (d, 2H, J=9.1 Hz), 7.13 (d, 1H, J=16.1 Hz). $^{13}$C NMR ($d_6$-DMSO) δ 164.70, 156.18, 149.34, 146.07, 145.53, 140.97, 130.84, 126.31, 124.97, 124.17, 121.84. HRMS (FAB) calcd for $C_{15}H_{10}O_6N_2O_6Ag$ ([M+Ag]$^+$): 420.9584. found 420.9589.

3-(Triphenylphosphinylacetyl)coumarin bromide (35): Bromide 35 was synthesized from 3-(bromoacetyl)coumarin (2 mmol) in 5 mL of $CH_2Cl_2$ and triphénylphosphine (2 mmol). The mixture was stirred 1.5 h at room temperature. The volatiles were removed under reduced pressure. The crude product was tritured with diethyl ether, filtered and washed again with diethyl ether to obtain a yellow crystalline solid (100% yield). mp 127-129° C. (dec.). $^1$H NMR ($CDCl_3$) δ 9.24 (s, 1H), 7.83 (m, 6H), 7.60 (m, 11H), 7.23 (m, 2H), 6.35 (d, 2H, J=12.2 Hz). $^{13}$C NMR δ 189.2, 158.3, 155.4, 151.4, 135.1, 134.3, 133.8, 132.5, 131.5, 130.5, 130.2, 129.1, 125.4, 119.2, 118.0. HRMS (FAB) calcd for $C_{29}H_{22}O_3P$ ([M]$^+$): 449.1379. found 449.1313.

3-(Triphenylphosphinylacetenyl)coumarin (36): Bromide 35 (1 mmol) was dissolved in 4 mL of EtOH, treated dropwise with and potassium carbonate (2 mmol) in 2 mL of $H_2O$, stirred 1.5 h at room temperature, diluted with 40 mL of $H_2O$ and extracted with 4×10 mL of EtOAc. The combined organic phases were dried on $MgSO_4$, filtered and evaporated under reduced pressure to give a yellow crystalline solid (95% yield). mp 114-116° C. (dec.). $^1H$ NMR ($CDCl_3$) δ 8.66 (s, 1H), 7.68 (m, 6H), 7.40 (m, 11H), 7.23 (d, 1H, J=8.2 Hz), 7.14 (d, 1H, J=7.4 Hz), 5.55 (d, 1H, J=27.3 Hz). $^{13}C$ NMR ($CDCl_3$) δ 168.4, 168.3, 154.1, 148.2, 138.0, 128.9, 128.0, 127.8, 127.7, 125.0, 123.0, 121.9, 120.6, 116.2, 113.0. HRMS (FAB) calcd for $C_{29}H_{22}O_3P$ ([M+H]$^+$): 449.1301. found 449.1302.

3-((E)-3-(4-Nitrophenyl)acryloyl)-2H-chromen-2-one (28a): Coumarin 36 (1 mmol) was dissolved in 10 mL of toluene, treated dropwise with p-nitrobenzaldehyde (0.67 mmol) in 5 mL of toluene, stirred overnight at room temperature, when a precipitate formed, that was filtered and washed with toluene to give a yellow solid (36% yield). mp 272-274° C. $^1H$ NMR ($d_6$-DMSO) δ 8.73 (s, 1H), 8.30 (d, 2H, J=8.8 Hz), 8.03 (d, 2H, J=8.7 Hz), 7.97 (d, 1H, J=6.7 Hz), 7.84 (s, 2H), 7.78 (t, 1H, J=8.4 Hz), 7.51 (d, 1H, J=8.4 Hz), 7.45 (t, 1H, J=7.5 Hz). HRMS (FAB) calcd for $C_{18}H_{12}NO_5$ ([M+H]$^+$): 322.0710. found 322.0716.

(E)-3-(4-Nitrophenyl)-1-(1,3-oxazinan-3-yl)prop-2-en-1-one (29a): Amide 29a was synthesized from 1,3 oxazinane (41) following the general procedure E. The pure product was obtained by flash chromatography (100% EtOAc) as a pale yellow solid (88% yield). mp 162-164° C. $^1H$ NMR ($CDCl_3$) δ 8.21 (d, 2H, J=8.7 Hz), 7.67 (d, 1H, J=15.4 Hz), 7.65 (d, 2H, J=8.5 Hz), 7.00 (d, 1H, J=15.5 Hz), 5.09 (s, 2H), 3.93 (t, 2H, J=5.1 Hz), 3.85 (t, 2H, J=5.1 Hz), 1.79 (qu, 2H, J=5.2 Hz). $^{13}C$ NMR ($CDCl_3$) δ 164.8, 148.4, 141.6, 140.7, 128.7, 124.4, 121.4, 78.2, 68.6, 42.0, 26.3. HRMS (FAB) calcd for $C_{13}H_{15}N_2O_4$ ([M+H]$^+$): 263.1036. found 263.1030.

(2E,4E)-5-(4-Nitrophenyl)penta-2,4-dienoic acid (42a): Acid 42a was prepared using general procedure B from p-nitrocinnamaldehyde and obtained as a yellow solid (82% yield). mp 291-293° C. (dec.). $^1H$ NMR ($d_6$-DMSO) δ 8.25 (d, 2H, J=8.7 Hz), 7.82 (d, 2H, J=8.7 Hz), 7.36 (m, 2H), 7.19 (d, 1H, J=14.7 Hz), 6.15 (d, 1H, J=14.1 Hz), 7.13 (d, 1H, J=16.1 Hz). $^{13}C$ NMR ($d_6$-DMSO) δ 168.2, 147.9, 144.3, 143.6, 138.1, 132.0, 129.0, 125.8, 125.0. HRMS (FAB) calcd for $C_{11}H_8NO_4$ ([M−H]$^-$): 218.0380. found 218.0451.

(2E,4E)-5-(4-Nitrophenyl)penta-2-4-dienoyl benzotriazolyl amide (37a): This amide was prepared using general procedure A from acid 42a and obtained as a yellow solid (48% yield). mp 265-267° C. $^1H$ NMR ($d_6$-DMSO) δ 8.32 (d, 2H, J=8.4 Hz), 8.24 (m, 2H), 7.96 (d, 2H, J=8.4 Hz), 7.80 (m, 3H), 7.67 (dd, 1H, J=15.3 Hz, 8.2 Hz), 7.53 (d, 1H, J=15.8 Hz), 6.87 (d, 1H, J=15.8 Hz. HRMS (FAB) calcd for $C_{17}H_{12}N_4O_3Ag$ ([M+Ag]$^+$): 428.0032. found 427.9783. $C_{17}H_{12}N_4O_3$ calcd C, 63.75; H, 3.76; N, 17.49. found C, 64.59; H, 3.86; N, 18.00.

(2E,4E)-5-(4-Nitrophenyl)-1-(pyridine-3-yl)penta-2,4-dien-1-one (38a): Enone 38a was prepared using the general procedure C. The green solid formed was filtered and purified by flash chromatography (100% EtOAc) to obtain a yellow-orange solid (33% yield). mp 212-214° C. (dec.). $^1H$ NMR ($CDCl_3$) δ 9.17 (s, 1H), 8.78 (d, 1H, J=3.4 Hz), 8.24 (d, 1H, J=9.8 Hz), 8.21 (d, 2H, J=8.8 Hz), 7.62 (d, 2H, J=8.6 Hz), 7.58 (d, 1H, J=13.3 Hz), 7.44 (m, 1H), 7.12 (m, 3H). $^{13}C$ NMR δ 180.1, 147.5, 144.1, 142.5, 139.2, 137.2, 134.9, 131.6, 126.7, 124.1, 123.2 (2 carbones), 120.8, 120.4. HRMS (FAB) calcd for $C_{16}H_{13}N_2O_3$ ([M+H]$^+$): 281.0921. found 281.0930.

1,3-Oxazinane (41): 3-amino propanol (15 mmol) and formaldehyde (15 mmol) were diluted in 20 mL of anhydrous EtOH. The mixture was stirred under $N_2$ overnight at room temperature. EtOH was removed under reduced pressure and the product was distilled (37-39° C., 1.2 mmHg) to give the pure product as a colorless liquid (57% yield). $^1H$ NMR ($CDCl_3$) δ 4.29 (s, 2H), 3.79 (t, 2H, J=5.3 Hz), 2.91 (t, 2H, J=5.5 Hz), 1.50 (qu, 2H, J=5.4 Hz). $^{13}C$ NMR ($CDCl_3$) δ 80.1, 67.7, 44.1, 28.2. HRMS (FAB) calcd for $C_4H_{10}N0$ ([M+H]$^+$): 88.0756. found 88.0760.

Benzyl azide (2a). Azide 2a was prepared using general procedure F from benzylbromide to give the desired product as a colorless oil in 97% isolated yield. IR (neat) 2094 cm$^{-1}$ ($\nu_{as}$, C—$N_3$). $^1H$ NMR (300 MHz, $CDCl_3$) δ 7.36 (m, 5H), 4.35 (s, 2H). $^{13}C$ NMR (75 MHz, $CDCl_3$) δ 135.4, 128.9, 128.4, 128.3, 54.8.

Azidooctane (2b). Azide 2b was prepared using general procedure F from 1-bromooctane to give the desired product as a colorless oil in 82% isolated yield. IR (neat) 2096 cm$^{-1}$ ($\nu_{as}$, C—$N_3$). $^1H$ NMR (300 MHz, $CDCl_3$) δ 3.25 (t, 2H, J=6.9 Hz), 1.60 (qu, 2H, J=6.8 Hz), 1.36 (m, 10H), 0.89 (t, 3H, J=6.9 Hz). $^{13}C$ NMR (75 MHz, $CDCl_3$) δ 55.8, 35.7, 33.3, 33.0, 31.0, 27.3, 19.4.

Azidocyclopentane (2c). Azide 2c was prepared using general procedure F from cyclopentyl bromide to give the desired product as a pale yellow translucide oil in 66% isolated yield. IR (neat) 2098 cm$^{-1}$ ($\nu_{as}$, C—$N_3$). $^1H$ NMR (300 MHz, $CDCl_3$) δ 3.91 (m, 1H), 1.68 (m, 8H). $^{13}C$ NMR (75 MHz, $CDCl_3$) δ 64.3, 35.9, 28.0.

4-nitrobenzyl azide (2d). Azide 2d was prepared using general procedure F from 4-nitrobenzyl bromide to give the desired product as a yellow oil in 99% isolated yield. IR (neat) 2105 cm$^{-1}$ ($\nu_{as}$, C—$N_3$). $^1H$ NMR (300 MHz, $CDCl_3$) δ 8.23 (d, 2H, J=8.8 Hz), 7.50 (d, 2H, J=8.9 Hz), 4.51 (s, 2H). $^{13}C$ NMR (75 MHz, $CDCl_3$) δ 142.4, 137.8, 124.8, 120.6, 55.8.

2-(azidomethyl)pyridine (2e). Azide 2e was prepared using general procedure F from 2-(bromomethyl)pyridine to give the desired product as a pale yellow oil in 95% isolated yield. IR (neat) 2101 cm$^{-1}$ ($\nu_{as}$, C—$N_3$). $^1H$ NMR (300 MHz, $CDCl_3$) δ 8.57 (d, 1H, J=4.3 Hz), 7.70 (td, 1H, J=7.7 Hz, 1.8 Hz), 7.32 (d, 1H, J=7.8 Hz), 7.23 (dd, 1H, J=4.9 Hz, 5.7 Hz), 4.46 (s, 2H). $^{13}C$ NMR (75 MHz, $CDCl_3$) δ 149.7, 144.1, 132.6, 119.6, 118.7, 57.6. HRMS (FAB) calcd for $C_6H_7N_4$ ([M+H]$^+$): 135.0665. found 135.0671.

(Azidomethyl)cyclohexane (2f). Azide 2f was prepared using general procedure F from 4-nitrobenzyl bromide to give the desired product as a colorless oil in 98% isolated yield. IR (neat) 2098 cm$^{-1}$ ($\nu_{as}$, C—$N_3$). $^1H$ NMR (300 MHz, $CDCl_3$) δ 3.10 (d, 2H, J=6.6 Hz), 1.72 (m, 5H), 1.53 (m, 1H), 1.21 (m, 3H), 0.97 (m, 2H). $^{13}C$ NMR (75 MHz, $CDCl_3$) δ 59.8, 41.5, 34.6, 30.6, 30.1.

3-nitrobenzyl azide (2g). Azide 2g was prepared using general procedure F from 3-nitrobenzyl bromide to give the desired product as a pale yellow oil in 88% isolated yield. IR (neat) 2104 cm$^{-1}$ ($\nu_{as}$, C—$N_3$). $^1H$ NMR (300 MHz, $CDCl_3$) δ 8.19 (m, 2H), 7.67 (m, 1H), 7.57 (m, 1H), 4.48 (s, 2H). $^{13}C$ NMR (75 MHz, $CDCl_3$) δ 137.9, 134.2, 130.2, 123.5, 123.1, 54.0.

2-nitrobenzyl azide (2h). Azide 2h was prepared using general procedure F from 2-nitrobenzyl bromide to give the desired product as a yellow oil in 88% isolated yield. IR (neat) 2102 cm$^{-1}$ ($\nu_{as}$, C—$N_3$). $^1H$ NMR (300 MHz, $CDCl_3$) δ 8.12 (d, 1H, J=8.7 Hz), 7.67 (m, 2H), 7.52 (m, 1H), 4.85 (s, 2H). $^{13}C$ NMR (75 MHz, $CDCl_3$) δ 134.3, 131.9, 130.4, 129.3, 125.6, 52.3.

2,3,4,5,6-penta fluorobenzyl azide (2i). Azide 2i was prepared using general procedure F from 2,3,4,5,6-pentafluorobenzyl bromide to give the desired product as a pale yellow oil in 89% isolated yield. IR (neat) 2110 cm$^{-1}$ ($\nu_{as}$, C—$N_3$).

$^1H$ NMR (300 MHz, $CDCl_3$) δ 4.47 (s, 2H). $^{13}C$ NMR (75 MHz, $CDCl_3$) δ 147.4 (m), 144.1 (m), 140.2 (m), 1439.6 (m), 136.3 (m), 109.6 (m), 41.9.

3,5-bis(trifluoromethyl)benzyl azide (2j). Azide 2j was prepared using general procedure F from 3,5-bis(trifluoromethyl)benzyl bromide to give the desired product as a colorless oil in 80% isolated yield. IR (neat) 2106 $cm^{-1}$ ($\nu_{as}$, C—$N_3$). $^1H$ NMR (300 MHz, $CDCl_3$) δ 7.86 (s, 1H), 7.79 (s, 2H), 4.56 (s, 2H). $^{13}C$ NMR (75 MHz, $CDCl_3$) δ 138.6, 132.5 (q, J=33.6 Hz), 128.2, 125.2, 122.5 (m), 121.6, 53.8.

(1-azidoethyl)-benzene (2k). Azide 2k was prepared using general procedure F from (1-bromoethyl)-benzene to give the desired product as a pale yellow oil in 99% isolated yield. IR (neat) 2105 $cm^{-1}$ ($\nu_{as}$, C—$N_3$). $^1H$ NMR (300 MHz, $CDCl_3$) δ 7.40 (m, 5H), 4.65 (q, 1H, J=6.8 Hz), 1.57 (d, 3H, J=6.8 Hz). $^{13}C$ NMR (75 MHz, $CDCl_3$) δ 141.1, 129.1, 128.4, 126.7, 61.4, 21.9.

Azidodiphenylmethane (2l). Azide 2l was prepared using general procedure F from bromodiphenylmethane to give the desired product as a pale yellow oil in 99% isolated yield. IR (neat) 2098 $cm^{-1}$ ($\nu_{as}$, C—$N_3$). $^1H$ NMR (300 MHz, $CDCl_3$) δ 7.36 (m, 10h), 5.74 (s, 1H). $^{13}C$ NMR (75 MHz, $CDCl_3$) δ 139.9, 129.0, 128.4, 127.7, 68.8.

(E)-1-(1-benzyl-1H-1,2,3-triazol-4-yl)-3-(4-nitrophenyl) prop-2-en-1-one (4a). Enone 4a was prepared using general procedure G from the alkyl azyde 2a to give the desired product, purified by chromatography (30:70 EtOAc/Hex), as a golden solid in 23% isolated yield. mp 196-198° C. $^1H$ NMR (300 MHz, $CDCl_3$) δ 8.28 (d, 2H, J=8.7 Hz), 8.10 (s, 1H), 8.04 (d, 1H, J=16.1 Hz), 7.94 (d, 1H, J=16.1 Hz), 7.84 (d, 2H, J=8.8 Hz), 7.40 (m, 3H), 7.34 (m, 2H), 5.61 (s, 2H). $^{13}C$ NMR (75 MHz, $CDCl_3$) δ. HRMS (FAB) calcd for $C_{18}H_{15}N_4O_3$ ($[M+H]^+$): 335.1139. found 335.1135.

(E)-1-(1-((3H-1,2,3-triazol-4-yl)methyl)-1H-1,2,3-triazol-4-yl)-3-(4-nitrophenyl)prop-2-en-1-one (4m). Enone 4m was prepared using general procedure G from the alkyl azyde 2m to give the desired product, purified by chromatography (50:50 EtOAc/Hex), as a pale yellow solid in 23% isolated yield. mp 186-188° C. (dec.). $^1H$ NMR (300 MHz, $d_6$-DMSO) δ 9.16 (s, 1H), 8.41 (d, 2H, J=8.3 Hz), 8.31 (b, 1H), 8.24 (d, 2H, J=8.1 Hz), 8.09 (m, 3H), 5.98 (s, 2H). $^{13}C$ NMR (75 MHz, $CDCl_3$) δ. HRMS (FAB) calcd for $C_{14}H_{12}N_7O_3$ ($[M+H]^+$): 326.0996. found 326.0996.

(E)-3-(4-nitrophenyl)-1-(1-octyl-1H-1,2,3-triazol-4-yl) prop-2-en-1-one (4b). Enone 4b was prepared using general procedure G from the alkyl azyde 2b to give the desired product, purified by chromatography (30:70 EtOAc/Hex), as a pale yellow solid in 20% isolated yield. mp 149-151° C. $^1H$ NMR (300 MHz, $CDCl_3$) δ 8.28 (d, 2H, J=8.8 Hz), 8.20 (s, 1H), 8.06 (d, 1H, J=16.0 Hz), 7.96 (d, 1H, J=16.1 Hz), 7.85 (d, 2H, J=8.8 Hz), 4.45 (t, 2H, J=7.2 Hz), 1.96 (m, 2H), 1.30 (m, 10H), 0.87 (t, 3H, J=6.5 Hz). $^{13}C$ NMR (75 MHz, $CDCl_3$) δ. HRMS (FAB) calcd for $C_{19}H_{25}N_4O_3$ ($[M+H]^+$): 357.1921. found 357.1934.

(E)-1-(1-cyclopentyl-1H-1,2,3-triazol-4-yl)-3-(4-nitrophenyl)prop-2-en-1-one (4c). Enone 4c was prepared using general procedure G from the alkyl azyde 2c to give the desired product, purified by chromatography (30:70 EtOAc/Hex), as a golden solid in 38% isolated yield. mp 172-174° C. $^1H$ NMR (300 MHz, $CDCl_3$) δ 8.28 (d, 2H, J=8.8 Hz), 8.22 (s, 1H), 8.05 (d, 1H, J=16.1 Hz), 7.96 (d, 1H, J=16.1 Hz), 7.84 (d, 2H, J=8.8 Hz), 5.03 (qu, 1H, J=6.7 Hz), 2.32 (m, 2H), 2.10 (m, 2H), 1.94 (m, 2H), 1.84 (m, 2H). $^{13}C$ NMR (75 MHz, $CDCl_3$) δ. HRMS (FAB) calcd for $C_{16}H_{17}N_4O_3$ ($[M+H]^+$): 313.1295. found 313.1297.

(E)-1-(1-(4-nitrobenzyl)-1H-1,2,3-triazol-4-yl)-3-(4-nitrophenyl)prop-2-en-1-one (4d). Enone 4d was prepared using general procedure G from the alkyl azyde 2d to give the desired product, purified by chromatography (30:70 EtOAc/Hex), as a pale yellow solid in 19% isolated yield. mp 208-210° C. (dec.). $^1H$ NMR (300 MHz, $CDCl_3$) δ 8.30 (d, 2H, J=8.8 Hz), 8.28 (d, 2H, J=8.8 Hz), 8.21 (s, 1H), 8.04 (d, 1H, J=16.1 Hz), 7.97 (d, 1H, J=16.1 Hz), 7.85 (d, 2H, J=8.8 Hz), 7.48 (d, 2H, J=8.5 Hz), 5.74 (s, 2H). $^{13}C$ NMR (75 MHz, $CDCl_3$) δ. HRMS (FAB) calcd for $C_{18}H_{14}N_5O_5$ ($[M+H]^+$): 380.0990. found 380.0994.

(E)-1-(1-(4-methoxybenzyl)-1H-1,2,3-triazol-4-yl)-3-(4-nitrophenyl)prop-2-en-1-one (4n). Enone 4n was prepared using general procedure G from the alkyl azyde 2n to give the desired product, purified by chromatography (50:50 EtOAc/Hex), as a yellow solid in 23% isolated yield. mp 196-198° C. (dec.). $^1H$ NMR (300 MHz, $CDCl_3$) δ 8.28 (d, 2H, J=8.8 Hz), 8.06 (s, 1H), 8.03 (d, 1H, J=15.9 Hz), 7.94 (d, 1H, J=16.1 Hz), 7.84 (d, 2H, J=8.8 Hz), 7.28 (d, 2H, J=8.7 Hz), 6.93 (d, 2H, J=8.7 Hz), 5.54 (s, 2H), 3.82 (s, 3H). $^{13}C$ NMR (75 MHz, $CDCl_3$) δ. HRMS (FAB) calcd for $C_{19}H_{17}N_4O_4$ ($[M+H]^+$): 365.1244. found 365.1249.

(E)-3-(4-nitrophenyl)-1-(1H-1,2,3-triazol-4-yl)prop-2-en-1-one (4o). To a 5 mL round-bottom flask equipped with a magnetic stir bar, was added enone 4n (27 μmol) in TFA (1 mL). The mixture was stirred 7 hours at 65° C. Then, the TFA was removed under reduced pressure and the crude was purified by chromatography (100% AcOEt) to give the pure product, as a white solid in 45% isolated. m.p. $^1H$ NMR (300 MHz, $d_6$-DMSO) δ 8.83 (s, 1H), 8.34 (d, 2H, J=8.9 Hz), 8.17 (d, 2H, J=8.8 Hz), 8.05 (d, 1H, J=16.1 Hz), 7.97 (d, 1H, J=15.9 Hz). $^{13}C$ NMR (75 MHz, $CDCl_3$) δ. HRMS (FAB) calcd for $C_{18}H_{15}N_4O_3$ ($[M+H]^+$). found.

(E)-3-(4-nitrophenyl)-1-(1-((pyridin-2-yl)methyl)-1H-1,2,3-triazol-4-yl)prop-2-en-1-one (4e). Enone 4e was prepared using general procedure G from the alkyl azyde 2e to give the desired product, purified by chromatography (100% EtOAc), as a yellow solid in 30% isolated yield. mp 220-222° C. $^1H$ NMR (300 MHz, $CDCl_3$) δ 8.63 (d, 2H, J=4.3 Hz), 8.41 (s, 1H), 8.28 (d, 2H, J=8.8 Hz), 8.05 (d, 1H, J=16.0 Hz), 7.95 (d, 1H, J=16.1 Hz), 7.84 (d, 2H, J=8.9 Hz), 7.74 (td, 1H, J=7.7 Hz, 1.7 Hz), 7.32 (m, 2H), 5.74 (s, 2H). $^{13}C$ NMR (75 MHz, $CDCl_3$) δ. HRMS (FAB) calcd for $C_{17}H_{14}N_5O_3$ ($[M+H]^+$): 336.1091. found 336.1099.

(E)-1-(1-(cyclohexylmethyl)-1H-1,2,3-triazol-4-yl)-3-(4-nitrophenyl)prop-2-en-1-one (4f). Enone 4f was prepared using general procedure G from the alkyl azyde 2f to give the desired product, purified by chromatography (30:70 EtOAc/Hex), as a yellow solid in 32% isolated yield. mp 193-195° C. $^1H$ NMR (300 MHz, $CDCl_3$) δ 8.28 (d, 2H, J=8.8 Hz), 8.16 (s, 1H), 8.06 (d, 1H, J=16.1 Hz), 7.96 (d, 1H, J=16.1 Hz), 7.85 (d, 2H, J=8.7 Hz), 4.28 (d, 2H, J=7.2 Hz), 1.94 (m, 1H), 1.67 (m, 5H), 1.27 (m, 3H), 1.04 (m, 2H). $^{13}C$ NMR (75 MHz, $CDCl_3$) δ. HRMS (FAB) calcd for $C_{18}H_{21}N_4O_3$ ($[M+H]^+$): 341.1608, found 341.1624.

(E)-1-(1-(3-nitrobenzyl)-1H-1,2,3-triazol-4-yl)-3-(4-nitrophenyl)prop-2-en-1-one (4g). Enone 4g was prepared using general procedure G from the alkyl azyde 2g to give the desired product, purified by chromatography (50:50 EtOAc/Hex), as a yellow solid in 19% isolated yield. mp 203-205° C. (dec.). $^1H$ NMR (300 MHz, $CDCl_3$) δ 8.29 (d, 4H, J=8.7 Hz), 8.22 (s, 1H), 8.04 (d, 1H, J=16.0 Hz), 7.97 (d, 1H, J=16.0 Hz), 7.85 (d, 2H, J=8.8 Hz), 7.65 (m, 2H), 5.74 (s, 2H). $^{13}C$ NMR (75 MHz, $CDCl_3$) δ. HRMS (FAB) calcd for $C_{18}H_{14}N_5O_5$ ($[M+H]^+$): 380.0990. found 380.0993.

(E)-1-(1-(2-nitrobenzyl)-1H-1,2,3-triazol-4-yl)-3-(4-nitrophenyl)prop-2-en-1-one (4h). Enone 4h was prepared using general procedure G from the alkyl azyde 2h to give the desired product, purified by chromatography (50:50 EtOAc/

Hex), as a yellow solid in 24% isolated yield. mp 211-213° C. (dec.). $^1H$ NMR (300 MHz, $CDCl_3$) δ 8.38 (s, 1H), 8.28 (d, 2H, J=8.8 Hz), 8.20 (dd, 1H, J=8.1 Hz, 1.3 Hz), 8.05 (d, 1H, J=16.0 Hz), 7.97 (d, 1H, J=16.1 Hz), 7.85 (d, 2H, J=8.9 Hz), 7.69 (td, 1H, J=7.5 Hz, 1.4 Hz), 7.60 (td, 1H, J=8.1 Hz, 1.5 Hz), 7.27 (dd, 1H, J=6.8 Hz, 0.8 Hz), 6.02 (s, 2H). $^{13}C$ NMR (75 MHz, $CDCl_3$) δ. HRMS (FAB) calcd for $C_{18}H_{14}N_5O_5$ ($[M+H]^+$): 380.0990. found 380.0991.

(E)-3-(4-nitrophenyl)-1-(1-(perfluorobenzyl)-1H-1,2,3-triazol-4-yl)prop-2-en-1-one (4i). Enone 4i was prepared using general procedure G from the alkyl azyde 2i to give the desired product, purified by chromatography (40:60 EtOAc/Hex), as a pale yellow solid in 33% isolated yield. mp 185-187 (dec.). $^1H$ NMR (300 MHz, $CDCl_3$) δ 8.29 (s, 1H), 8.28 (d, 2H, J=8.8 Hz), 7.98 (s, 2H), 7.83 (d, 2H, J=8.9 Hz), 5.74 (s, 2H). $^{13}C$ NMR (75 MHz, $CDCl_3$) δ. HRMS (FAB) calcd for $C_{18}H_{10}F_5N_4O_3$ ($[M+H]^+$): 425.0668. found 425.0666.

(E)-1-(1-(3,5-bis(trifluoromethyl)benzyl)-1H-1,2,3-triazol-4-yl)-3-(4-nitrophenyl)prop-2-en-1-one (4j). Enone 4j was prepared using general procedure G from the alkyl azyde 2j to give the desired product, purified by chromatography (40:60 EtOAc/Hex), as a pale yellow solid in 52% isolated yield. mp 182-184° C. $^1H$ NMR (300 MHz, $CDCl_3$) δ 8.28 (d, 2H, J=8.8 Hz), 8.25 (s, 1H), 8.04 (d, 1H, J=16.1 Hz), 7.97 (d, 1H, J=16.2 Hz), 7.93 (s, 1H), 7.85 (d, 2H, J=8.8 Hz), 7.79 (s, 2H), 5.76 (s, 2H). $^{13}C$ NMR (75 MHz, $CDCl_3$) δ. HRMS (FAB) calcd for $C_{20}H_{13}F_6N_4O_3$ ($[M+H]^+$): 471.0886. found 471.0886.

(E)-3-(4-nitrophenyl)-1-(1-(1-phenylethyl)-1H-1,2,3-triazol-4-yl)prop-2-en-1-one (4k). Enone 4k was prepared using general procedure G from the alkyl azyde 2k to give the desired product, purified by chromatography (30:70 EtOAc/Hex), as a yellow solid in 48% isolated yield. mp 153-155° C. $^1H$ NMR (300 MHz, $CDCl_3$) δ 8.28 (d, 2H, J=8.9 Hz), 8.10 (s, 1H), 8.04 (d, 1H, J=16.1 Hz), 7.94 (d, 1H, J=16.1 Hz), 7.83 (d, 2H, J=8.9 Hz), 7.39 (m, 5H), 5.91 (q, 1H, J=7.1 Hz), 2.05 (d, 3H, J=7.1 Hz). $^{13}C$ NMR (75 MHz, $CDCl_3$) δ. HRMS (FAB) calcd for $C_{19}H_{17}N_4O_3$ ($[M+H]^+$): 349.1295. found 349.1289.

(E)-1-(1-benzhydryl-1H-1,2,3-triazol-4-yl)-3-(4-nitrophenyl)prop-2-en-1-one (4l). Enone 4l was prepared using general procedure G from the alkyl azyde 2l to give the desired product, purified by chromatography (30:70 EtOAc/Hex), as a yellow solid in 39% isolated yield. mp. $^1H$ NMR (300 MHz, $CDCl_3$) δ 8.28 (d, 2H, J=8.8 Hz), 8.08 (d, 1H, J=16.0 Hz), 8.01 (d, 1H, J=16.1 Hz), 7.84 (d, 2H, J=8.8 Hz), 7.40 (m, 6H), 7.19 (s, 1H), 7.12 (m, 4H). $^{13}C$ NMR (75 MHz, $CDCl_3$) δ. HRMS (FAB) calcd for $C_{24}H_{18}N_4O_3Na$ ($[M+Na]^+$): 433.1271. found 433.1270.

All literature, patents, published patent applications cited herein are hereby incorporated by reference.

One or more currently preferred embodiments have been described by way of example. It will be apparent to persons skilled in the art that a number of variations and modifications can be made without departing from the scope of the invention as defined in the claims.

The invention claimed is:

1. A compound of Formula II:

II

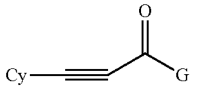

wherein (I) G is (1)

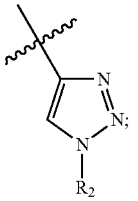

or, (3)

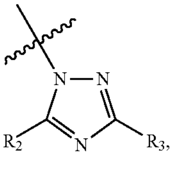

and, Cy is aryl or heteroaryl, said aryl or heteroaryl being optionally substituted with one or more $R^1$ substituents, or, (II) G is (2)

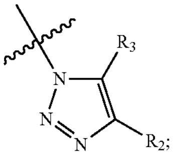

or (4)

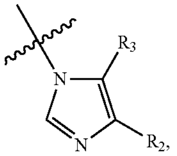

and, Cy is a) a six-membered carbocyclic aromatic ring substituted with one or more $R^1$ substituents;

b) a six-membered carbocyclic aromatic ring fused to a saturated or aromatic five-membered carbocyclic ring, wherein said fused rings are optionally substituted with one or more $R^1$ substituents;

c) a six-membered carbocyclic aromatic ring fused to a saturated, unsaturated, or aromatic six-membered carbocyclic ring, wherein said fused rings are optionally substituted with one or more $R^1$ substituents; or, d) heteroaryl that is optionally substituted with one or more $R^1$ substituents;

$R^1$ is halogen, $NO_2$,

CN, $C_1$-$C_6$ alkyl, $NR^5R^6$, $COR^4$, $C(O)OR^4$, $S(O)_2R^4$, $(CONR^5R^6)_{1-3}$, or $S(O)_2NR^5R^6$, wherein alkyl is optionally substituted with one or more $R^7$ substituents;

wherein when G is (1), $R^2$ is
H,
halogen,
$NO_2$,
CN,
$C_1$-$C_6$ alkyl,
$NR^5R^6$,
$COR^4$;
$C(O)OR^4$;
$S(O)_2R^4$;
$(CONR^5R^6)_{1-3}$, or
$S(O)_2NR^5R^6$,
wherein alkyl is optionally substituted with one or more $R^7$ substituents;
wherein when G is (2) or (4), $R^2$ and $R^3$ are each independently
H,
halogen,
$NO_2$,
CN,
$C_1$-$C_6$ alkyl,
$NR^5R^6$,
$COR^4$;
$C(O)OR^4$;
$S(O)_2R^4$;
$(CONR^5R^6)_{1-3}$, or
$S(O)_2NR^5R^6$,
or, $R^2$ and $R^3$ together with the carbon atoms to which they are attached form a benzene ring,
wherein alkyl is optionally substituted with one or more $R^7$ substituents;
wherein when G is (3),
$R^2$ is
H,
halogen,
CN,
$C_1$-$C_6$ alkyl,
$COR^4$;
$C(O)OR^4$;
$S(O)_2R^4$;
$(CONR^5R^6)_{1-3}$, or
$S(O)_2NR^5R^6$,
wherein alkyl is optionally substituted with one or more $R^7$ substituents, and,
$R^3$ is
H,
halogen,
$NO_2$,
CN,
$C_1$-$C_6$ alkyl,
$NR^5R^6$,
$COR^4$;
$C(O)OR^4$;
$S(O)_2R^4$;
$(CONR^5R^6)_{1-3}$, or
$S(O)_2NR^5R^6$,
wherein alkyl is optionally substituted with one or more $R^7$ substituents;
$R^4$ is
1) $C_1$-$C_6$ alkyl,
2) aryl, or
3) heteroaryl,
$R^5$ and $R^6$ are independently
1) H, or
2) $C_1$-$C_6$ alkyl,
or,
$R^5$ and $R^6$ together with the nitrogen atom to which they are bonded form a five or six membered heterocyclic ring;
wherein alkyl is optionally substituted with one or more $R^7$ substituents;
and,
$R^7$ is
1) halogen,
2) $NO_2$,
3) CN,
4) $C_1$-$C_6$ alkyl,
5) haloalkyl,
6) $OR^4$,
7) $NH_2$, $N(C_1$-$C_6$ alkyl$)_2$ or $NH(C_1$-$C_6$ alkyl),
8) $SR^4$,
9) $COR^4$,
10) $C(O)OR^4$,
11) $S(O)_2R^4$,
12) $CONH_2$, CON ($C_1$-$C_6$ alkyl$)_2$ or CONH($C_1$-$C_6$ alkyl), or
13) $S(O)_2NH_2$ $S(O)_2N(C_1$-$C_6$alkyl$)_2$ or S(O)NH ($C_1$-$C_6$ alkyl).

2. A compound of formula III:

III

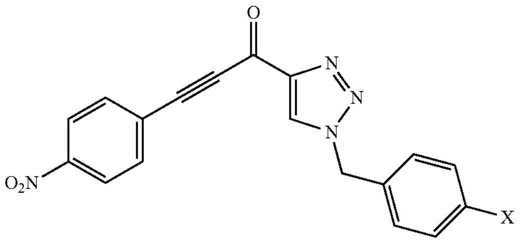

wherein X is H or $NO_2$.

3. The compound of claim 2, wherein X is H.

4. The compound of claim 2, wherein X is $NO_2$.

* * * * *